United States Patent
Nazarenko et al.

(10) Patent No.: US 7,537,886 B1
(45) Date of Patent: May 26, 2009

(54) PRIMERS AND METHODS FOR THE DETECTION AND DISCRIMINATION OF NUCLEIC ACIDS

(75) Inventors: Irina Nazarenko, Gaithersburg, MD (US); Ayoub Rashtchian, Gaithersburg, MD (US)

(73) Assignee: Life Technologies Corporation, Carlsbad, CA (US)

( * ) Notice: Subject to any disclaimer, the term of this patent is extended or adjusted under 35 U.S.C. 154(b) by 0 days.

(21) Appl. No.: 09/599,594

(22) Filed: Jun. 22, 2000

Related U.S. Application Data

(60) Provisional application No. 60/175,959, filed on Jan. 13, 2000, provisional application No. 60/139,890, filed on Jun. 22, 1999.

(51) Int. Cl.
 *C12Q 1/68* (2006.01)
(52) U.S. Cl. .......................................................... 435/6
(58) Field of Classification Search .................... 435/6, 435/91.2; 536/23.1, 24.3, 24.31
See application file for complete search history.

(56) References Cited

U.S. PATENT DOCUMENTS

| | | | |
|---|---|---|---|
| 4,358,535 A | 11/1982 | Falkow et al. .................. 435/5 |
| 4,446,237 A | 5/1984 | Berninger .................. 436/504 |
| 4,563,417 A | 1/1986 | Albarella et al. ............... 435/6 |
| 4,581,333 A | 4/1986 | Kourilsky et al. .............. 436/6 |
| 4,582,788 A | 4/1986 | Erlich ........................... 435/6 |
| 4,582,789 A | 4/1986 | Sheldon, III et al. ........... 435/6 |
| 4,683,194 A | 7/1987 | Saiki et al. ..................... 435/6 |
| 4,683,202 A | 7/1987 | Mullis ......................... 435/91 |
| 4,889,818 A | 12/1989 | Gelfand et al. ............. 435/194 |
| 4,965,188 A | 10/1990 | Mullis et al. ................... 435/6 |
| 5,047,342 A | 9/1991 | Chatterjee ................... 435/194 |
| 5,079,352 A | 1/1992 | Gelfand et al. ............... 536/27 |
| 5,118,801 A | 6/1992 | Lizardi et al. ................ 536/27 |
| 5,137,814 A | 8/1992 | Rashtchian et al. .......... 435/91 |
| 5,143,854 A | 9/1992 | Pirrung et al. ............... 436/518 |
| 5,194,370 A | 3/1993 | Berninger et al. ........... 436/501 |
| 5,200,314 A | 4/1993 | Urdea |
| 5,244,797 A | 9/1993 | Kotewicz et al. ............ 435/194 |
| 5,252,743 A | 10/1993 | Barrett et al. ............. 548/303.7 |
| 5,270,179 A | 12/1993 | Chatterjee .................. 435/69.1 |
| 5,312,728 A | 5/1994 | Lizardi et al. .................. 435/6 |
| 5,334,515 A | 8/1994 | Rashtchian et al. ........ 435/91.2 |
| 5,338,671 A | 8/1994 | Scalice et al. .............. 435/91.2 |
| 5,348,853 A | 9/1994 | Wang et al. ..................... 435/6 |
| 5,374,553 A | 12/1994 | Gelfand et al. ........... 435/252.3 |
| 5,436,149 A | 7/1995 | Barnes ....................... 435/194 |
| 5,436,327 A | 7/1995 | Southern et al. ......... 536/25.34 |
| 5,445,934 A | 8/1995 | Fodor et al. ..................... 435/6 |
| 5,449,603 A | 9/1995 | Nielson et al. .................. 435/6 |
| 5,455,166 A | 10/1995 | Walker ....................... 435/91.2 |
| 5,487,972 A | 1/1996 | Gelfand et al. ................. 435/6 |
| 5,503,979 A | 4/1996 | Kramer et al. .................. 435/6 |
| 5,512,462 A | 4/1996 | Cheng ........................ 435/91.2 |
| 5,538,848 A | 7/1996 | Livak et al. ..................... 435/5 |
| 5,565,322 A * | 10/1996 | Heller ............................ 435/6 |
| 5,578,467 A | 11/1996 | Schuster et al. ............. 435/91.2 |
| 5,587,287 A | 12/1996 | Scalice et al. .................. 435/6 |
| 5,593,840 A | 1/1997 | Bhatnagar et al. .............. 435/6 |
| 5,594,138 A | 1/1997 | Dykstra et al. .............. 540/596 |
| 5,594,183 A | 1/1997 | Colin ....................... 73/864.52 |
| 5,595,890 A | 1/1997 | Newton et al. ............. 435/91.2 |
| 5,599,695 A | 2/1997 | Pease et al. ................. 435/91.1 |
| 5,605,824 A | 2/1997 | Nielson et al. .............. 435/194 |
| 5,614,365 A | 3/1997 | Tabor et al. ..................... 435/6 |
| 5,639,611 A | 6/1997 | Wallace et al. .................. 435/6 |
| 5,646,019 A | 7/1997 | Nielson et al. ............. 435/91.5 |
| 5,668,005 A | 9/1997 | Kotewicz et al. ............ 435/194 |
| 5,714,331 A | 2/1998 | Buchardt et al. ................ 435/6 |
| 5,728,526 A | 3/1998 | George, Jr. et al. ............. 435/6 |
| 5,736,336 A | 4/1998 | Buchardt et al. ................ 435/6 |
| 5,763,170 A | 6/1998 | Raybuck ........................ 435/6 |
| 5,773,257 A | 6/1998 | Nielson et al. ............. 435/91.1 |
| 5,800,992 A | 9/1998 | Fodor et al. ..................... 435/6 |
| 5,837,832 A | 11/1998 | Chee et al. .................. 536/22.1 |
| 5,846,729 A | 12/1998 | Wu et al. ........................ 435/6 |
| 5,866,336 A | 2/1999 | Nazarenko et al. ............. 435/6 |
| 5,869,251 A | 2/1999 | Schuster et al. ................ 435/6 |
| 5,876,930 A | 3/1999 | Livak et al. ..................... 435/6 |
| 5,925,517 A | 7/1999 | Tyagi et al. ..................... 435/6 |
| 5,945,526 A * | 8/1999 | Lee et al. .................... 536/26.6 |
| 5,948,899 A | 9/1999 | Arnold, Jr. et al. .......... 536/24.3 |
| 5,952,172 A | 9/1999 | Mende et al. ................... 435/6 |
| 6,037,130 A * | 3/2000 | Tyagi et al. ..................... 435/6 |
| 6,048,690 A | 4/2000 | Heller et al. .................... 435/6 |
| 6,090,552 A | 7/2000 | Nazarenko et al. ............. 435/6 |
| 6,117,635 A | 9/2000 | Nazarenko et al. ............. 435/6 |
| 6,117,986 A | 9/2000 | Nardone et al. ............. 534/727 |

(Continued)

FOREIGN PATENT DOCUMENTS

EP 0 50424 9/1981

(Continued)

OTHER PUBLICATIONS

Abe, T., et al., "Specific inhibition of influenza virus RNA polymerase and nucleoprotein gene expression by circular dumbbell RNA/DNA chimeric oligonucleotides containing antisense phosphodiester oligonucleotides," *FEBS Lett.* 425:91-96, Elsevier Science Publishers B.V., Amsterdam, Netherlands (1998).

(Continued)

*Primary Examiner*—Kenneth R. Horlick
*Assistant Examiner*—Mark Staples
(74) *Attorney, Agent, or Firm*—Bernadette M. Perfect; Life Technologies Corporation

(57) ABSTRACT

The present invention provides novel primers and methods for the detection of specific nucleic acid sequences. The primers and methods of the invention are useful in a wide variety of molecular biology applications and are particularly useful in allele specific PCR.

13 Claims, 19 Drawing Sheets

U.S. PATENT DOCUMENTS

| | | | | |
|---|---|---|---|---|
| 6,150,097 | A | * | 11/2000 | Tyagi et al. ..................... 435/6 |
| 6,248,526 | B1 | | 6/2001 | Weimer ......................... 435/6 |
| 6,277,607 | B1 | | 8/2001 | Tyagi et al. ................ 435/91.2 |
| 6,465,175 | B2 | * | 10/2002 | Horn et al. ..................... 435/6 |

FOREIGN PATENT DOCUMENTS

| | | |
|---|---|---|
| EP | 0 84796 | 1/1983 |
| EP | 0 119 448 | 2/1984 |
| EP | 0 144 914 | 11/1984 |
| EP | 0 201 184 | 3/1986 |
| EP | 0 237 362 | 3/1987 |
| EP | 0 258 017 | 8/1987 |
| EP | 0 329 822 | 8/1988 |
| EP | 0 684 315 | 3/1995 |
| EP | 0 436 644 B1 | 4/1996 |
| EP | 0 709 466 A2 | 5/1996 |
| EP | 0 774 516 A2 | 5/1997 |
| EP | 0 795 612 A2 | 9/1997 |
| EP | 0 881 302 A2 | 12/1998 |
| EP | 0 795 612 A3 | 3/1999 |
| EP | 1 087 020 A2 | 3/2001 |
| WO | WO 88/10315 | 12/1988 |
| WO | WO 89/06700 | 7/1989 |
| WO | WO 90/03446 | 4/1990 |
| WO | WO 92/06188 | 4/1992 |
| WO | WO 92/06200 | 4/1992 |
| WO | WO 92/14845 | 9/1992 |
| WO | WO 96/10640 | 4/1996 |
| WO | WO 96/15270 * | 5/1996 |
| WO | WO 97/39008 | 10/1997 |
| WO | WO 98/02449 | 1/1998 |
| WO | WO 98/35060 | 8/1998 |
| WO | WO 98/47921 | 10/1998 |
| WO | WO 99/10366 | 3/1999 |
| WO | WO 00/56916 | 9/2000 |

OTHER PUBLICATIONS

Austermann, S., et al., "Inhibition of Human Immunodeficiency Virus Type 1 Reverse Transcriptase by 3'-Blocked Oligonuclecotide Primers," *Biochem. Pharmacol.* 43:2581-2589, Elsevier Science, Oxford, England (1992).

Barnes, W.M., "The fidelity of *Taq* polymerase catalyzing PCR is improved by an N-terminal deletion," *Gene* 112:29-35, Elsevier Science Publishers B.V., Amsterdam, Netherlands (1992).

Bonnet, G., et al., "Thermodynamic basis of the enhanced specificity of structured DNA probes," *Proc. Natl. Acad. Sci. USA* 96:6171-6176, National Academy of Sciences of the USA, Washington, D.C. (May 1999).

Cardullo et al, "Detection of nucleic acid hybridization by non radiative fluorescence resonance energy transfer," *Proc. Natl. Acad. Sci. USA* 85:8790-8794, National Academy of Sciences of the USA, Washington, D.C. (1988).

Chedin, F., et al., "Novel homology of replication protein A in archaea: implications for the evolution of ssDNA-binding proteins," *TIBS* 23:273-277, International Union of Biochemistry and Elsevier Trends Journal, Cambridge, England (1998).

Clegg, R.M., et al., "Fluorescence Resonance Energy Transfer Analysis of the Structure of the Four-Way DNA Junction," *Biochem.* 31:4846-4856, American Chemical Society, Washington D.C. (1992).

Clegg, R.M., "Fluorescence Resonance Energy Transfer and Nucleic Acids," *Methods Enzymol.* 211:353-388, Academic Press Inc., New York, NY (1992).

Clegg, R.M., et al., "Observing the helical geometry of double-stranded DNA in solution by fluorescence resonance energy transfer," *Proc. Natl. Acad. Sci. USA* 90:2994-2998, National Academy of Sciences of the USA, Washington, D.C. (1993).

Flaman, J.-M., et al., "A rapid PCR fidelity assay," *Nucl. Acids Res.* 22:3259-3260, Oxford University Press, Oxford, England (1994).

Forster, Z., "Experimentelle und theoretische Untersuchung des zwischenmolekularen Übergangs von Elektronenanregungsenergie," *Z. Naturforsh 4A*:321-327, Verlag der Zeitschrift für Naturforschung, Tübingen, Germany (1949).

Gerard, G.F., et al., "cDNA Synthesis by Moloney Murine Leukemia Virus Rnase H-Minus Reverse Transcriptase Possessing Full DNA Polymerase Activity," *Focus* 14:91-93, Life Technologies, Inc., Gaithersburg, MD (1992).

Holland, P.M., et al., "Detection of specific polymerase chain reaction product by utilizing the 5'→3' exonuclease activity of *Thermus aquaticus* DNA polymerase," *Proc. Natl. Acad. Sci. USA* 88:7276-7280, National Academy of Sciences of the USA, Washington, D.C. (1991).

Houts, G.E., et al., "Reverse Transcriptase from *Avian myeloblastosis* Virus," *J. Virol.* 29:517-522, American Society for Microbiology, Baltimore, MD (1979).

Idriss, H., and Stammers, D.K., "Inhibition of HIV-1 Reverse Transcriptance by Defined Template/Primer DNA Oligonucleotides: Effect of Template Length and Binding Characteristics," *J. Enzyme Inhib.* 8: 91-112, Harwood Academic, Chur, New York (1994).

Jendis, J., et al., "Inhibition of Replication of Fresh HIV Type 1 Patient Isolates by a Polypurine Tract-Specific Self-Complementary Oligodeoxynucleotide," *AIDS Res. Human Retrov.* 12:1161-1168, Mary Ann Leibert, Inc., Publishers, Larchmont, NY (1996).

Ju, J., et al., "Fluorescence energy transfer dye-labeled primers for DNA sequencing and analysis," *Proc. Natl. Acad. Sci. USA* 92:4347-4351, National Academy of Sciences of the USA, Washington, D.C. (1995).

Kainz, A.P., et al., "Specificity-Enhanced Hot-Start PCR: Addition of Double-Stranded DNA Fragments Adapted to the Annealing Temperature," *BioTechniques* 28:278-282, Eaton Publishing Company, Natick, MA (Feb. 2000).

Kelly, T. J., et al., "Identification and characterization of a single-stranded DNA-binding protein from the archaeon *Methanococcus jannaschii,*" *Proc. Natl. Acad. Sci. USA* 95:14634-14639, National Academy of Sciences of the USA, Washington, D.C. (1998).

Kleppe, K., et al., "Studies on Polynucleotides. XCVI. Repair Replications of Short Synthetic DNA's as Catalyzed by DNA Polymerases," *J. Mol. Biol.* 56:341-361, Academic Press, Inc., New York, NY (1971).

Kotewicz, M.L., et al., "Isolation of cloned Moloney murine leukemia virus reverse transcriptase lacking ribonuclease H activity," *Nucl. Acids Res.* 16:265-277, Oxford University Press, Oxford, England (1988).

Kuwasaki, T., et al., "Hairpin Antisense Oligonucleotides Containing 2'-Methoxynucleosides with Base-Pairing in the Stem Region at the 3'-end: Penetration, Localization, and Anti-HIV Activity," *Biochem. Biophys. Res. Commun.* 228:623-631, Academic Press, Inc., Orlando, FL (1996).

Kwoh, D.Y., et al., "Transcription-based amplification system and detection of amplified human immunodeficiency virus type 1 with a bead-based sandwich hybridization format," *Proc. Natl. Acad. Sci. USA* 86:1173-1177, National Academy of Sciences of the USA, Washington, D.C. (1989).

Lawyer, F.C., et al., "High-Level Expression, Purification, and Enzymatic Characterization of Full-Length *Thermus aquaticus* DNA Polymerase and a Truncated Form Deficient in 5' to 3' Exonuclease Activity," *PCR Meth. Appl.* 2:275-287, Cold Spring Harbor Laboratory Press, Cold Spring Harbor, NY (1993).

Lee, L.G., et al., "Allelic discrimination by nick-translation PCR with fluorogenic probes," *Nucl. Acids Res.* 21:3761-3766, Oxford University Press, Oxford, England (1993).

Luo, G., et al., "Inhibition of influenza viral polymerases by minimal viral RNA decoys," *J. Gen. Virol.* 78:2329-2333, Society for General Microbiology, London, England (1997).

Lyamichev, V., et al., "Structure-Specific Endonucleolytic Cleavage of Nucleic Acids by Eubacterial DNA Polymerases," *Science* 260:778-783, Association for the Advancement of Science, Washington D.C. (1993).

Maury, G., et al., "Template. Phosphorothioate Oligonucleotides Duplexes As Inhibitors of HIV-1 Reverse Transcriptase," *Biochem. Biophys. Res. Commun.* 186:1249-1256, Academic Press, Inc., Orlando, FL (1992).

Mullis, K., et al., "Specific Enzymatic Amplification of DNA In Vitro: The Polymerase Chain Reaction," *Cold Spring Harbor Symp. Quant. Biol. 51*:263-273, Cold Spring Harbor Laboratory Of Quantitative Biology, Cold Spring Harbor NY, (1986).

Nakaya, T., et al., "Decoy Approach Using RNA-DNA Chimera Oligonucleotides To Inhibit the Regulatory Function of Human Immunodeficiency Virus Type 1 Rev Protein," *Antimicrobiol. Agents Chemother. 41*:319-325, American Society For Microbiology Washington D.C. (1997).

Nazarenko, I.A., et al., "A closed tube format for amplification and detection of DNA based on energy transfer," *Nucl. Acids Res. 25*:2516-2521, Oxford University Press, Oxford, England (1997).

Ozaki, H., and McLaughlin, L.W., "The estimation of distances between specific backbone-labeled sites in DNA using fluoroscence resonance energy transfer," *Nucl. Acids Res. 20*:5205-5214, Oxford University Press, Oxford, England (1992).

Panet, A., and Khorana, H.G., "Studies on Polynucleotides. The Linkage of Deoxyribopolynucleotide Templates to Cellulose and its Use in Their Replication," *J. Biol. Chem. 249*:5213-5221, American Society for Biochemistry and Molecular Biology, Inc., Baltimore, MD (1974).

Paris, P.L., et al., "Probing DNA sequences in solution with a monomer-excimer fluorescence color change," *Nucl. Acids Res. 26*:3789-3793, Oxford University Press, Oxford, England (1998).

Saiki, R.K., et al., "Primer-Directed Enzymatic Amplification of DNA with a Thermostable DNA Polymerase," *Science 239*:487-491, Association for the Advancement of Science, Washington D.C. (1988).

Sarin, P.S., et al., "Inhibition of acquired immunodeficiency syndrome virus by oligodeoxynucleoside methylphosphonates," *Proc. Natl. Acad. Sci. USA 85*:7448-7451, National Academy of Sciences of the USA, Washington, D.C. (1988).

Schneider, D.J., et al., "High Affinity ssDNA Inhibitors of the Reverse Transcriptase of Type 1 Human Immunodeficiency Virus," *Biochem. 34*:9599-9610, American Chemical Society, Washington D.C. (1995).

Selvin, P.R., "Fluorescence Resonance Energy Transfer," *Methods Enzymol. 246*:300-334, Academic Press Inc., New York, NY (1995).

Selvin, P.R., and Hearst, J.E., "Luminescence energy transfer using a terbium chelate: Improvements on fluorescence energy transfer," *Proc. Natl. Acad. Sci. USA 91*:10024-10028, National Academy of Sciences of the USA, Washington, D.C. (1994).

Soltis, D.A., and Skalka, A.M., "The α and β chains of avian retrovirus reverse transcriptase independently expressed in *Escherichia coli*: Characterization of enzymatic activities," *Proc. Natl. Acad. Sci. USA 85*:3372-3376, National Academy of Sciences of the USA, Washington, D.C. (1988).

Stein, C.A., et al., "Physicochemical properties of phosphorothioate oligodeoxynucleotides," *Nucl. Acids Res. 16*:3209-3221, Oxford University Press, Oxford, England (1988).

Tyagi, S., and Kramer, F.R., "Molecular Beacons: Probes that Fluoresce Upon Hybridization," *Nature Biotechnol. 14*:303-309, Nature Publishing Co., New York, NY (1996).

Wang, Y., et al., "Rapid Sizing of Short Tandem Repeat Alleles Using Capillary Array Electrophoresis and Energy-Transfer Fluorescent Primers," *Anal. Chem. 67*:1197-1203, American Chemical Society, Washington D.C. (1995).

Wu, D.Y., et al., "Allele-specific enzymatic amplification of β-globin genomic DNA for diagnosis of sickle cell anemia," *Proc. Natl. Acad. Sci. USA 86*:2757-2760, National Academy of Sciences of the USA, Washington, D.C. (1989).

Wu, D.Y., et al., "The Ligation Amplification Reaction (LAR)-Amplification of Specific DNA Sequences Using Sequential Rounds of Template-Dependent Ligation," *Genomics 4*:560-569, Academic Press, San Diego, CA (1989).

Xu, D., et al., "Melting and Premelting Transitions of an Oligomer Measured by DNA Base Fluorescence and Absorption," *Biochem. 33*:9592-9599, American Chemical Society, Washington D.C. (1994).

Yamana, K. et al., "Flourescent-labeled Oligonucleotides that Exhibit a Measurable Signal in the Presence of Complementary DNA," *Nucl. Acids Symp. Ser. 27*:135-136, London Information Retrieval, London, England (1992).

"Amplifuor™ Universal Amplification & Detection System," Intergen Company Catalog, 4 pages, Purchase, NY (1999).

Rye, H.S., et al., "Stable fluorescent complexes of double-stranded DNA with bis-intercalating asymmetric cyanine dyes: properties and applications," *Nucl. Acids Res. 20*:2803-2812, Oxford University Press (1992).

Varani, G., "Exceptionally Stable Nucleic Acid Hairpins," *Annu. Rev. Biophys. Biomol. Struct. 24*:379-404, Annual Reviews Inc. (1995).

Walder, R.Y., et al., "Use of PCR primers containing a 3'-terminal ribose residue to prevent cross-contamination of amplified sequences," *Nucl. Acids Res. 21*:4339-4343, Oxford University Press (1993).

Wang, G.T., et al., "Design and Synthesis of Neew Fluorogenic HIV Protease Substrates Based on Resonance Energy Transfer," *Tetrahedron Lett. 31*:6493-6496, Pergamon Press PLC (1990).

Yamamoto, N. and Okamoto, T., "A rapid detection of PCR amplification product using a new fluorescent intercalator; the pyrylium dye, P2," *Nucl. Acids Res. 23*:1445-1446, Oxford University Press (1995).

International Search Report of International Application No. PCT/US00/17085, mailed May 23, 2001.

Blok, H.J. and Kramer, F.R., "Amplifiable hybridization probes containing a molecular switch," *Mol. Cell. Probes 11*:187-194, Academic Press, Ltd. (1997).

Giesendorf, B.A.J., et al., "Molecular beacons: a new approach for semiautomated mutation analysis," *Clin. Chem. 44*: 482-486, American Association for Clinical Chemistry (Mar. 1998).

Haas, S., et al., "Primer design for large scale sequencing," *Nucl. Acids Res. 26*:3006-3012, Oxford University Press (Jun. 1998).

Kostrikis, L.G., et al., "Spectral Genotyping of Human Alleles," *Science 279*:1228-1229, American Association for the Advancement of Science (Feb. 1998).

Kramer, F.R. and Lizardi, P.M., "Replicatable RNA reporters," *Nature 339*:401-402, Macmillan Journals Ltd. (1989).

Lengauer, C., et al., "Genetic instabilities in human cancers," *Nature 396*:643-649, Macmillan Journals Ltd. (Dec. 1998).

Leone, G., et al., "Molecular beacon probes combined with amplification by NASBA enable homogeneous, real-time detection of RNA," *Nucl. Acids Res. 26*:2150-2155, Oxford University Press (May 1998).

Marras, S.A.E., et al., "Multiplex detection of single-nucleotide variations using molecular beacons," *Genetic Analysis: Biomolecular Engineering 14*:151-156, Elsevier Science B.V. (Feb. 1999).

Monia, B.P., et al., "Selective Inhibition of Mutant Ha-ras mRNA Expression by Antisense Oligonucleotides," *J. Biol. Chem. 267*:19954-19962, American Society for Biochemistry and Molecular Biology, Inc. (1992).

Moran, S., et al., "Non-hydrogen bonding 'terminator' nucleosides increase the 3'-end homogeneity of enzymatic RNA and DNA synthesis," *Nucl. Acids Res. 24*:2044-2052, Oxford University Press (1996).

Newton, C.R., et al., "Analysis of any point mutation in DNA. The amplification refractory mutation system (ARMS)," *Nucl. Acids Res. 17*:2503-2516, IRL Press (1989).

Serra, M.J. and Turner, D.H., "Predicting Thermodynamic Properties of RNA," *Meth. Enzymol. 259*:242-261, Academic Press, Inc. (1995).

Tyagi, S., et al., "Extremely sensitive, background-free gene detection using binary probes and Qβ replicase," *Proc. Natl. Acad. Sci. USA 93*:5395-5400, National Academy of Sciences (1996).

Tyagi, S., et al., "Multicolor molecular beacons for allele discrimination," *Nat. Biotechnol. 16*:49-53, Nature Publishing Group (Jan. 1998).

Vet, J.A.M., et al., "Multiplex detection of four pathogenic retroviruses using molecular beacons," *Proc. Natl. Acad. Sci. USA 96*:6394-6399, National Academy of Sciences (May 1999).

Whitcombe, D., et al., "Detection of PCR products using self-probing amplicons and fluorescence," *Nat. Biotechnol. 17*:804-807, Nature Publishing Group (Aug. 1999).

Wittwer, C.T., et al., "Continuous Fluorescence Monitoring of Rapid Cycle DNA Amplification," *BioTechniques 22*:130-131,134-138, Eaton Publishing Co. (1997).

Zubritsky, E., "Pinning Down PCR," *Analytical Chemistry News & Features 71*:191A-195A, American Chemical Society (Mar. 1999).

Ailenberg, M. and M. Silverman, "Controlled Hot Start and Improved Specificity in Carrying Out PCR Utilizing Touch-Up and Loop Incorporated Primers (TULIPS)," *BioTechniques* 29(5): 1018-1024 (minus advertisement pages) (Nov. 2000) (publisher: Eaton Publishing Co.).

Ehlen, T. and L. Dubeau, "Detection of *Ras* Point Mutations By Polymerase Chain Reaction Using Mutation-Specific, Inosine-Containing Oligonucleotide Primers," *Biochemical and Biophysical Research Communications* 160(2): 441-447 (Apr. 1989) (publisher: Academic Press, Inc.).

Kaboev, O.K. et al., "PCR hot start using primers with the structure of molecular beacons (hairpin-like structure)," *Nucleic Acids Research* 28(21): e94 (two pages) (Nov. 2000) (publisher: Oxford University Press).

* cited by examiner

Primer linear    hairpin

IL4 cDNA 1, 5 - $10^6$ copies
2, 6 - $10^4$ copies
3, 7 - $10^2$ copies
4, 8 - 0 copies ← PCR product
← Primer-dimer 1 2 3 4 5 6 7 8

1 - 297 WT
2 - 300 WT
3 - 297 C→T Mut
4 - 300 G→T Mut
M - 100 bp marker

```
                         SEQUENCE LISTING

<160> NUMBER OF SEQ ID NOS:  43

<210> SEQ ID NO 1
<211> LENGTH: 23
<212> TYPE: DNA
<213> ORGANISM: Artificial Sequence
<220> FEATURE:
<223> OTHER INFORMATION: Description of Artificial Sequence:
      Oligonucleotide
<221> NAME/KEY: protein_bind
<222> LOCATION: (18)
<223> OTHER INFORMATION: fluorescein labeled

<400> SEQUENCE: 1
ccttctcatg gtggctgtag aac                                              23

<210> SEQ ID NO 2
<211> LENGTH: 23
<212> TYPE: DNA
<213> ORGANISM: Artificial Sequence
<220> FEATURE:
<223> OTHER INFORMATION: Description of Artificial Sequence:
      Oligonucleotide
<221> NAME/KEY: protein_bind
<222> LOCATION: (1)
<223> OTHER INFORMATION: fluorescein labeled

<400> SEQUENCE: 2
ccttctcatg gtggctgtag aac                                              23

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 3
gttctacagc caccatgaga agg                                              23

<210> SEQ ID NO 4
<211> LENGTH: 23
<212> TYPE: DNA
<213> ORGANISM: Artificial Sequence
<220> FEATURE:
```

```
<223> OTHER INFORMATION: Description of Artificial Sequence:
      Oligonucleotide
<221> NAME/KEY: protein_bind
<222> LOCATION: (23)
<223> OTHER INFORMATION: TAMRA labeled

<400> SEQUENCE: 4
ggggctgcga ctgtgctccg gca                                            23

<210> SEQ ID NO 5
<211> LENGTH: 23
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 5
tgccggagca cagtcgcagc ccc                                            23

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide
<221> NAME/KEY: protein_bind
<222> LOCATION: (1)
<223> OTHER INFORMATION: fluorescein labeled

<400> SEQUENCE: 6
aataatagga tgaggcagga                                                20

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide
<221> NAME/KEY: protein_bind
<222> LOCATION: (1)
<223> OTHER INFORMATION: BODIPY 530/550 labeled

<400> SEQUENCE: 7
aataatagga tgaggcagga                                                20

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 8
tcctgcctca tcctattatt                                                20

<210> SEQ ID NO 9
<211> LENGTH: 23
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 9
```

-continued

```
gagttgaccg taacagacat ctt                                            23
```

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence:
      Oligonucleotide
<221> NAME/KEY: protein_bind
<222> LOCATION: (17)
<223> OTHER INFORMATION: fluorescein labeled

<400> SEQUENCE: 10

```
ggcattgccg acaggatgta gaag                                           24
```

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 11

```
gggccggact cgtcatac                                                  18
```

<210> SEQ ID NO 12
<211> LENGTH: 28
<212> TYPE: DNA
<213> ORGANISM: Artificial Sequence
<220> FEATURE:
<223> OTHER INFORMATION: Description of Artificial Sequence:
      Oligonucleotide
<221> NAME/KEY: protein_bind
<222> LOCATION: (6)
<223> OTHER INFORMATION: fluorescein labeled

<400> SEQUENCE: 12

```
ggttgtagag cactcagcac aatgaaga                                       28
```

<210> SEQ ID NO 13
<211> LENGTH: 23
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 13

```
gagttgaccg taacagacat ctt                                            23
```

<210> SEQ ID NO 14
<211> LENGTH: 23
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 14

```
ccttctcatg gtggctgtag aac                                            23
```

<210> SEQ ID NO 15
<211> LENGTH: 23
<212> TYPE: DNA
<213> ORGANISM: Artificial Sequence
<220> FEATURE:

```
<223> OTHER INFORMATION: Description of Artificial Sequence:
      Oligonucleotide

<400> SEQUENCE: 15
ccttctcatg gtggctgtag aat                                            23

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 16
gtgtccttct catggtggct gtag                                           24

<210> SEQ ID NO 17
<211> LENGTH: 24
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 17
gtgtccttct catggtggct gtat                                           24

<210> SEQ ID NO 18
<211> LENGTH: 23
<212> TYPE: DNA
<213> ORGANISM: Artificial Sequence
<220> FEATURE:
<223> OTHER INFORMATION: Description of Artificial Sequence:
      Oligonucleotide
<221> NAME/KEY: protein_bind
<222> LOCATION: (18)
<223> OTHER INFORMATION: fluorescein labeled

<400> SEQUENCE: 18
ccttctcatg gtggctgtag aac                                            23

<210> SEQ ID NO 19
<211> LENGTH: 23
<212> TYPE: DNA
<213> ORGANISM: Artificial Sequence
<220> FEATURE:
<223> OTHER INFORMATION: Description of Artificial Sequence:
      Oligonucleotide
<221> NAME/KEY: protein_bind
<222> LOCATION: (18)
<223> OTHER INFORMATION: fluorescein labeled

<400> SEQUENCE: 19
ccttctcatg gtggctgtag aat                                            23

<210> SEQ ID NO 20
<211> LENGTH: 24
<212> TYPE: DNA
<213> ORGANISM: Artificial Sequence
<220> FEATURE:
<223> OTHER INFORMATION: Description of Artificial Sequence:
      Oligonucleotide
<221> NAME/KEY: protein_bind
<222> LOCATION: (22)
<223> OTHER INFORMATION: fluorescein labeled

<400> SEQUENCE: 20
```

-continued

```
gtgtccttct catggtggct gtag                                              24

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence:
      Oligonucleotide
<221> NAME/KEY: protein_bind
<222> LOCATION: (22)
<223> OTHER INFORMATION: fluorescein labeled

<400> SEQUENCE: 21
gtgtccttct catggtggct gtat                                              24

<210> SEQ ID NO 22
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide
<221> NAME/KEY: protein_bind
<222> LOCATION: (23)
<223> OTHER INFORMATION: fluorescein labeled

<400> SEQUENCE: 22
ctaccgggtg tctgtgtctc ggtag                                             25

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 23
cgtacctggc tatctgtgtc                                                   20

<210> SEQ ID NO 24
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 24
cgtacctggc tatctgtgtt                                                   20

<210> SEQ ID NO 25
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 25
gacacctggc tatctgtgtc                                                   20

<210> SEQ ID NO 26
<211> LENGTH: 22
<212> TYPE: DNA
<213> ORGANISM: Artificial Sequence
<220> FEATURE:
```

<223> OTHER INFORMATION: Description of Artificial Sequence:
      Oligonucleotide

<400> SEQUENCE: 26
aacacacctg gctatctgtg tt                                                 22

<210> SEQ ID NO 27
<211> LENGTH: 27
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 27
ctacagtcct tctcatggtg gctgtag                                            27

<210> SEQ ID NO 28
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 28
cttcctgaga gccgaactgt agtga                                              25

<210> SEQ ID NO 29
<211> LENGTH: 26
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 29
acatgtattt gcatggaaaa caactc                                             26

<210> SEQ ID NO 30
<211> LENGTH: 31
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 30
tcactacttc ctgagagccg aactgtagtg a                                       31

<210> SEQ ID NO 31
<211> LENGTH: 33
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 31
gagttgtaca tgtatttgca tggaaaacaa ctc                                     33

<210> SEQ ID NO 32
<211> LENGTH: 24
<212> TYPE: DNA
<213> ORGANISM: Artificial Sequence
<220> FEATURE:
<223> OTHER INFORMATION: Description of Artificial Sequence:

Oligonucleotide

<400> SEQUENCE: 32
gctcagaatg atgtttccac cttc                                                24

<210> SEQ ID NO 33
<211> LENGTH: 25
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 33
aaatcatact agctcaccag caatg                                               25

<210> SEQ ID NO 34
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 34
gaaggtgctc agaatgatgt ttccaccttc                                          30

<210> SEQ ID NO 35
<211> LENGTH: 31
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 35
cattgcaaat catactagct caccagcaat g                                        31

<210> SEQ ID NO 36
<211> LENGTH: 22
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 36
tggcagttga atgccaagta at                                                  22

<210> SEQ ID NO 37
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 37
acagccactg tgcccaggtc                                                     20

<210> SEQ ID NO 38
<211> LENGTH: 28
<212> TYPE: DNA
<213> ORGANISM: Artificial Sequence
<220> FEATURE:
<223> OTHER INFORMATION: Description of Artificial Sequence:
      Oligonucleotide

```
<400> SEQUENCE: 38
attacttggc agttgaatgc caagtaat                                          28

<210> SEQ ID NO 39
<211> LENGTH: 26
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 39
gacctgacag ccactgtgcc caggtc                                            26

<210> SEQ ID NO 40
<211> LENGTH: 23
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 40
atttcatggg ggaaacaaag atg                                               23

<210> SEQ ID NO 41
<211> LENGTH: 20
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 41
atacctgcgc tcaccacagg                                                   20

<210> SEQ ID NO 42
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 42
catctttatt tcatggggga aacaaagatg                                        30

<210> SEQ ID NO 43
<211> LENGTH: 26
<212> TYPE: DNA
<213> ORGANISM: Artificial Sequence
<220> FEATURE:
<223> OTHER INFORMATION: Description of Artificial Sequence:
      Oligonucleotide

<400> SEQUENCE: 43
cctgtgatac ctgcgctcac cacagg                                            26
```

PRIMERS AND METHODS FOR THE DETECTION AND DISCRIMINATION OF NUCLEIC ACIDS

CROSS-REFERENCE TO RELATED APPLICATIONS

The present application is related to U.S. Provisional Patent Application Nos. 60/139,890, filed Jun. 22, 1999, and 60/175,959, filed Jan. 13, 2000, both of which are specifically incorporated herein by reference in their entirety.

BACKGROUND OF THE INVENTION

1. Field of the Invention

The present invention relates to the field of molecular biology. In particular, the present invention relates to novel primers for use in the detection and discrimination of nucleic acids. The novel primers of the present invention will find broad applicability in the field of molecular biology and, in particular, in the detection of products in nucleic acid amplification reactions and in the discrimination between alleles of a given target gene.

2. Related Art

Assays capable of detecting and quantifying the presence of a particular nucleic acid molecule in a sample are of substantial importance in forensics, medicine, epidemiology and public health, and in the prediction and diagnosis of disease. Such assays can be used, for example, to identify the causal agent of an infectious disease, to predict the likelihood that an individual will suffer from a genetic disease, to determine the purity of drinking water or milk, or to identify tissue samples. The desire to increase the utility and applicability of such assays is often frustrated by assay sensitivity. Hence, it would be highly desirable to develop more sensitive detection assays.

Nucleic acid detection assays can be predicated on any characteristic of the nucleic acid molecule, such as its size, sequence and, if DNA, susceptibility to digestion by restriction endonucleases. The sensitivity of such assays may be increased by altering the manner in which detection is reported or signaled to the observer. Thus, for example, assay sensitivity can be increased through the use of detectably labeled reagents. A wide variety of such labels have been used for this purpose. Detectable labels include, for example, radioactive isotopes, fluorescent labels, chemiluminescent labels, bioluminescent labels and enzyme labels. U.S. Pat. No. 4,581,333 describes the use of enzyme labels to increase sensitivity in a detection assay. Radioisotopic labels are disclosed in U.S. Pat. Nos. 4,358,535, and 4,446,237. Fluorescent labels (EP 144,914), chemical labels (U.S. Pat. Nos. 4,582,789 and 4,563,417) and modified bases (EP 119,448) have also been used in an effort to improve the efficiency with which detection can be observed.

Although the use of highly detectable labeled reagents can improve the sensitivity of nucleic acid detection assays, the sensitivity of such assays remains limited by practical problems which are largely related to non-specific reactions which increase the background signal produced in the absence of the nucleic acid the assay is designed to detect. In response to these problems, a variety of detection and quantification methods using DNA amplification have been developed.

Many current methods of identification and quantification of nucleic acids rely on amplification and/or hybridization techniques. While many of these involve a separation step, several that allow detection of nucleic acids without separating the labeled primer or probe from the reaction have been developed. These methods have numerous advantages compared to gel-based methods, such as gel electrophoresis, and dot-blot analysis, for example, and require less time, permit high throughput, prevent carryover contamination and permit quantification through real time detection. Most of these current methods are solution-based fluorescence methods that utilize two chromophores. These methods utilize the phenomena of fluorescence resonance energy transfer (FRET) in which the energy from an excited fluorescent moiety is transferred to an acceptor molecule when the two molecules are in close proximity to each other. This transfer prevents the excited fluorescent moiety from releasing the energy in the form of a photon of light thus quenching the fluorescence of the fluorescent moiety. When the acceptor molecule is not sufficiently close, the transfer does not occur and the excited fluorescent moiety may then fluoresce. The major disadvantages of systems based on FRET are the cost of requiring the presence of two modified nucleotides in a detection oligonucleotide and the possibility that the efficiency of the quenching may not be sufficient to provide a usable difference in signal under a given set of assay conditions. Other known methods which permit detection without separation are: luminescence resonance energy transfer (LRET) where energy transfer occurs between sensitized lanthanide metals and acceptor dyes (Selvin, P. R., and Hearst, J. D., Proc. Natl. Acad. Sci. USA 91:10024-10028 (1994)); and color change from excimer-forming dyes where two adjacent pyrenes can form an excimer (fluorescent dimer) in the presence of the complementary target, resulting in a detectably shifted fluorescence peak (Paris, P. L. et al., Nucleic Acids Research 26:3789-3793 (1998)).

Various methods are known to those skilled in the art for the amplification of nucleic acid molecules. In general, a nucleic acid target molecule is used as a template for extension of an oligonucleotide primer in a reaction catalyzed by polymerase. For example, Panet and Khorana (J. Biol. Chem. 249:5213-5221 (1974)) demonstrate the replication of deoxyribopolynucleotide templates bound to cellulose. Kleppe et al., (J. Mol. Biol. 56:341-361 (1971)) disclose the use of double and single-stranded DNA molecules as templates for the synthesis of complementary DNA.

Other known nucleic acid amplification procedures include transcription based amplification systems (Kwoh, D. et al., Proc. Natl. Acad. Sci. USA 86:1173 (1989); PCT appl. WO 88/10315). Schemes based on ligation ("Ligation Chain Reaction", "LCR") of two (or more) oligonucleotides in the presence of a target nucleic acid having a sequence complementary to the sequence of the product of the ligation reaction have also been used (Wu, D. Y. et al., Genomics 4:560 (1989)). Other suitable methods for amplifying nucleic acid based on ligation of two oligonucleotides after annealing to complementary nucleic acids are known in the art.

PCT appl. WO 89/06700 discloses a nucleic acid sequence amplification scheme based on the hybridization of a promoter/primer sequence to a target single-stranded DNA ("ssDNA") followed by transcription of many RNA copies of the sequence. This scheme is not cyclic; i.e. new templates were not produced from the resultant RNA transcripts.

EP 0 329,822 discloses an alternative amplification procedure termed Nucleic Acid Sequence-Based Amplification (NASBA). NASBA is a nucleic acid amplification process comprising cyclically synthesizing single-stranded RNA ("ssRNA"), ssDNA, and double-stranded DNA (dsDNA). The ssRNA is a first template for a first primer oligonucleotide, which is elongated by reverse transcriptase (RNA dependent DNA polymerase). The RNA is then removed from resulting DNA:RNA duplex by the action of ribonuclease H (RNase H, an RNase specific for RNA in a duplex with either DNA or RNA). The resultant ssDNA is a second template for a second primer. The second primer includes the sequences of an RNA polymerase promoter (exemplified by T7 RNA polymerase) located 5' to the primer sequence which hybridizes to the ssDNA template. This primer is then extended by a DNA polymerase (exemplified by the large "Klenow" fragment of E. coli DNA polymerase I), resulting in the production of a double-stranded DNA ("dsDNA") molecule, having a sequence identical to that of the portion of the original RNA located between the primers and having additionally, at one end, a promoter sequence. This promoter sequence can be used by the appropriate RNA polymerase to make many RNA copies of the DNA. These copies can then re-enter the cycle leading to very swift amplification. With proper choice of enzymes, this amplification can be done isothermally without addition of enzymes at each cycle. Because of the cyclical nature of this process, the starting sequence can be chosen to be in the form of either DNA or RNA.

U.S. Pat. No. 5,455,166 and EP 0 684 315 disclose a method called Strand Displacement Amplification (SDA). This method is performed at a single temperature and uses a combination of a polymerase, an endonuclease and a modified nucleoside triphosphate to amplify single-stranded fragments of the target DNA sequence. A target sequence is fragmented, made single-stranded and hybridized to a primer that contains a recognition site for an endonuclease. The primer:target complex is then extended with a polymerase enzyme using a mixture of nucleoside triphosphates, one of which is modified. The result is a duplex molecule containing the original target sequence and an endonuclease recognition sequence. One of the strands making up the recognition sequence is derived from the primer and the other is a result of the extension reaction. Since the extension reaction was performed using a modified nucleotide, one strand of the recognition site is modified and resistant to endonuclease digestion. The resultant duplex molecule is then contacted with an endonuclease which cleaves the unmodified strand causing a nick. The nicked strand is extended by a polymerase enzyme lacking 5'-3' exonuclease activity resulting in the displacement of the nicked strand and the production of a new duplex molecule. The new duplex molecule can then go through multiple rounds of nicking and extension producing multiple copies of the target sequence.

The most widely used method of nucleic acid amplification is the polymerase chain reaction (PCR). A detailed description of PCR is provided in the following references: Mullis, K. et al., *Cold Spring Harbor Symp. Quant. Biol.* 51:263-273 (1986); European Patent (EP) 50,424; EP 84,796; EP 258, 017; EP 237,362; EP 201,184; U.S. Pat. No. 4,683,202; U.S. Pat. No. 4,582,788; and U.S. Pat. No. 4,683,194. In its simplest form, PCR involves the amplification of a target double-stranded nucleic acid sequence. The double-stranded sequence is denatured and an oligonucleotide primer is annealed to each of the resultant single strands. The sequences of the primers are selected so that they will hybridize in positions flanking the portion of the double-stranded nucleic acid sequence to be amplified. The oligonucleotides are extended in a reaction with a polymerase enzyme, nucleotide triphosphates and the appropriate cofactors resulting in the formation of two double-stranded molecules each containing the target sequence. Each subsequent round of denaturation, annealing and extension reactions results in a doubling of the number of copies of the target sequence as extension products from earlier rounds serve as templates for subsequent replication steps. Thus, PCR provides a method for selectively increasing the concentration of a nucleic acid molecule having a particular sequence even when that molecule has not been previously purified and is present only in a single copy in a particular sample. The method can be used to amplify either single or double-stranded nucleic acids. The essence of the method involves the use of two oligonucleotides to serve as primers for the template dependent, polymerase mediated replication of the desired nucleic acid molecule.

PCR has found numerous applications in the fields of research and diagnostics. One area in which PCR has proven useful is the detection of single nucleotide mutations by allele specific PCR (ASPCR) (see for example, U.S. Pat. Nos. 5,639,611 inventors Wallace, et al. and 5,595,890 inventors Newton, et al.). As originally described by Wu, et al. (*Proceedings of the National Academy of Sciences*, USA, 86:2757-2760, 1989), ASPCR involves the detection of a single nucleotide variation at a specific location in a nucleic acid molecule by comparing the amplification of the target using a primer sequence whose 3'-terminal nucleotide is complementary to a suspected variant nucleotide to the amplification of the target using a primer in which the 3'-terminal nucleotide is complementary to the normal nucleotide. In the case where the variant nucleotide is present in the target, amplification occurs more efficiently with the primer containing the 3'-nucleotide complementary to the variant nucleotide while in the case where the normal nucleotide is present in the target, amplification is more efficient with the primer containing 3'-nucleotide complementary to the normal nucleotide.

While this technology can be used to identify single nucleotide substitutions in a nucleic acid, it nonetheless suffers from some drawbacks in practical applications. The difference in efficiency of amplification between the primers may not be sufficiently large to permit easily distinguishing between the normal nucleotide and the mutant nucleotide. When the mismatched primer is extended with a significant frequency in the earlier rounds of the amplification, there may not be a large difference in the amount of product present in the later rounds. This problem requires careful selection of the number of amplification cycles and reaction conditions. An additional problem with this methodology is presented by the detection step after the amplification. In general, this is accomplished by separating the reaction products by electrophoresis and then visualizing the products. The imposition of a separation step dramatically increases the time and expense required for conducting this type of analysis. In order to obviate the need for a separation step, various FRET based solution phase methods of detection have been used. These methods suffer from the drawbacks discussed above.

Whether detection of a given nucleic acid target sequence is to be done with or without amplification of the nucleic acid sample containing the target sequence, there remains a need in the art for more sensitive and more discriminating methods of detecting a target nucleic acid sequence.

Methods for detecting nucleic acid amplification products commonly use gel electrophoresis, which separates the amplification product from the primers on the basis of a size differential. Alternatively amplification products can be detected by immobilization of the product, which allows one to wash away free primer (for example, in dot-blot analysis) and hybridization of specific probes by traditional solid phase hybridization methods. However, several methods for monitoring the amplification process without prior separation of primer or probes have been described. All of these methods are based on FRET.

One method, described in U.S. Pat. No. 5,348,853 and Wang et al., *Anal. Chem.* 67:1197-1203 (1995), uses an energy transfer system in which energy transfer occurs between two fluorophores on the probe. In this method, detection of the amplified molecule takes place in the amplification reaction vessel, without the need for a separation step. The Wang et al. method uses an "energy-sink" oligonucleotide complementary to the reverse primer. The "energy-sink" and reverse-primer oligonucleotides have donor and acceptor labels, respectively. Prior to amplification, the labeled oligonucleotides form a primer duplex in which energy transfer occurs freely. Then, asymmetric PCR is carried out to its late-log phase before one of the target strands is significantly overproduced.

A second method for detection of amplification product without prior separation of primer and product is the 5' nuclease PCR assay (also referred to as the TAQMAN™ assay) (Holland et al., *Proc. Natl. Acad. Sci. USA* 88:7276-7280 (1991); Lee et al., *Nucleic Acids Res.* 21:3761-3766 (1993)). This assay detects the accumulation of a specific PCR product by hybridization and cleavage of a doubly labeled fluorogenic probe (the "TAQMAN" probe) during the amplification reaction. The fluorogenic probe consists of an oligonucleotide labeled with both a fluorescent reporter dye and a quencher dye. During PCR, this probe is cleaved by the 5'-exonuclease activity of DNA polymerase if it hybridizes to the segment being amplified. Cleavage of the probe generates an increase in the fluorescence intensity of the reporter dye. In the TAQMAN assay, the donor and quencher are preferably located on the 3' and 5'-ends of the probe, because the requirement that 5'-3 hydrolysis be performed between the fluorophore and quencher may be met only when these two moieties are not too close to each other (Lyamichev et al., *Science* 260:778-783 (1993)).

Another method of detecting amplification products (namely MOLECULAR BEACONS) relies on the use of energy transfer using a "beacon probe" described by Tyagi and Kramer (*Nature Biotech.* 14:303-309 (1996)). This method employs oligonucleotide hybridization probes that can form hairpin structures. On one end of the hybridization probe (either the 5' or 3' end) there is a donor fluorophore, and on the other end, an acceptor moiety. In the case of the Tyagi and Kramer method, this acceptor moiety is a quencher, that is, the acceptor absorbs energy released by the donor, but then does not itself fluoresce. Thus when the beacon is in the open conformation, the fluorescence of the donor fluorophore is detectable, whereas when the beacon is in hairpin (closed) conformation, the fluorescence of the donor fluorophore is quenched. When employed in PCR, the beacon probe, which hybridizes to one of the strands of the PCR product, is in "open conformation," and fluorescence is detected, while those that remain unhybridized will not fluoresce. As a result, the amount of fluorescence will increase as the amount of PCR product increases, and thus may be used as a measure of the progress of the PCR.

Another method of detecting amplification products which relies on the use of energy transfer is the SUNRISE PRIMER method of Nazarenko et al. (*Nucleic Acids Research* 25:2516-2521 (1997); U.S. Pat. No. 5,866,336). SUNRISE PRIMERS are based on FRET and other mechanisms of non-fluorescent quenching. SUNRISE PRIMERS consist of a single stranded primer with a hairpin structure at its 5'end. The hairpin stem is labeled with a donor/quencher pair. The signal is generated upon the unfolding and replication of the hairpin sequence by polymerase.

While there is a body of literature on use of fluorescent labeled nucleic acids in a variety of applications involving nucleic acid hybridization or nucleic acid amplification, the majority of applications involve separation of unhybridized probes or unincorporated primers, followed by detection. None of these methodologies, describe or discuss real time detection of probes or primers, or changes in the fluorescence properties of a fluorescently labeled oligonucleotide upon hybridization or incorporation into amplified product. The surprising and novel finding of the present invention is based, in part, on the measurement of a change in one or more of the fluorescent properties of labeled probes or primers upon becoming double-stranded.

The present invention thus solves the problem of detecting nucleic acids, in particular amplification and/or synthesis products, by providing methods for detecting such products that are adaptable to many methods for amplification or synthesis of nucleic acid sequences and that greatly decrease the possibility of carryover contamination. The compounds and methods of the invention provide substantial improvements over those of the prior art. First, they permit detection of the amplification or synthesis products without prior separation of unincorporated fluorescent labeled oligonucleotides. Second, they allow detection of the amplification or synthesis product directly, by incorporating the labeled oligonucleotide into the product. Third, they do not require labeling of oligonucleotides with two different compounds (like FRET-based methods), and thus, simplify the production of the labeled oligonucleotides.

SUMMARY OF THE INVENTION

The present invention provides oligonucleotides that may comprise one or more modifications internally, and/or, at or near the 3' and/or 5' termini. Suitable modifications include, but are not limited to, the inclusion of labels, the inclusion of specificity enhancing groups, the inclusion of quenching moieties and the like. The oligonucleotides of the present invention may also comprise one or more sequences complementary to all or a portion of a target or template sequence of interest. In some embodiments, the oligonucleotides of the present invention may be in the form of a hairpin. Hairpin oligonucleotides may be modified or un-modified. Hairpin oligonucleotides of the present invention may contain one or more single stranded regions at or near the stem of the hairpin and may be blunt ended or comprise overhanging sequences on the 3' and/or 5'-ends. The hairpin oligonucleotides of the present invention may also contain any number of stem and loop structures at any location in the oligonucleotide. In some preferred embodiments, the oligonucleotides of the present invention may be used for the detection and/or discrimination of target or template nucleic acid molecules by methods involving primer extension including, but not limited to, nucleic acid synthesis and amplification (e.g. PCR) as well as by other methods involving hybridization of a probe and/or primer. The oligonucleotides of the present invention may be used with any extension reaction known to those skilled in the art. Such extension reactions include, but are not limited to, extension of a primer on a DNA template using a DNA polymerase to produce a complementary DNA strand and extension of a primer on an RNA template using a reverse transcriptase to produce a complementary DNA strand. The oligonucleotides of the present invention may also be used in detection/discrimination of target or template nucleic acid molecules using methods involving hybridization of one or more of the oligonucleotides of the invention to one or more target nucleic acid molecules of interest.

In one aspect, oligonucleotides of the invention may comprise one or multiple labels (e.g. detectable labels), which may be the same or different. In some preferred embodiments, the labels may be fluorescent moieties. Labeled oligonucleotides of the invention may be used to detect the presence or absence of or to quantify the amount of nucleic acid molecules in a sample by, for example, hybridization of such oligonucleotides to such nucleic acid molecules. Optionally, such oligonucleotides may be extended in a synthesis and/or amplification reaction and detection/quantification may be accomplished during or after such reactions. In accordance with one aspect of the invention, such detection/quantification is based on the observation that the labeled oligonucleotides in double-stranded form have a detectable change in one or more properties (preferably a fluorescent property) compared to the oligonucleotides in single-stranded form. In another aspect of the invention, a change in a detectable property (preferably a fluorescent property) upon extension of the oligonucleotide of the invention is used to detect/quantify a target/template nucleic acid. Fluorescent properties in which a change may be detected include, but are not limited to, fluorescent intensity (increase or decrease), fluorescent polarization, fluorescence lifetime and quantum yield of fluorescence. Thus, hybridization and/or extension of the labeled oligonucleotides of the invention to a nucleic acid molecule to be detected/quantified results in a detectable change in one or more of the labels used and, in particular, when using fluorescent labels, a detectable change in one or more fluorescent properties. In this aspect of the invention, multiple different oligonucleotides may be used to detect multiple different target sequences in the same sample (e.g. multiplexing) and such different oligonucleotides may be differentially labeled to allow simultaneous and/or sequential detection of the multiple target sequences.

In another aspect, the present invention provides modified oligonucleotides comprising one or more specificity enhancing groups. In some preferred embodiments, oligonucleotides of the present invention may be provided with one or more specificity enhancing groups that render such oligonucleotides substantially less extendable, for example in a synthesis or amplification reaction, when the 3'-most nucleotide of the oligonucleotide is not base paired with a target or template nucleic acid sequence. In some embodiments, the specificity enhancing group may be placed at or near the 3'-most nucleotide of the oligonucleotide. The specificity enhancing group may be attached to the oligonucleotide using any methodology known to those of skill in the art and may be attached to the oligonucleotide via a linker group. Such linker groups may be of varying length and chemical composition, i.e., hydrophobicity, charge etc. The specificity enhancing groups of the present invention may be attached to any part of the nucleotide to be modified, i.e., base, sugar or phosphate group. Specificity enhancing groups of the present invention may be or include detectable groups, including but not limited to, fluorescent groups, chemiluminescent, radio-labeled groups and the like. In some embodiments, the specificity enhancing groups of the present invention may be fluorescent groups which undergo a detectable change in one or more fluorescent properties upon extension of the oligonucleotide or may be any other detectable label allowing detection of the nucleic acid of interest. Preferably, the label exhibits a detectable change when the oligonucleotide of the invention is extended in a synthesis or amplification reaction.

Oligonucleotides of the present invention may be in the form of a hairpin. The hairpins of the present invention preferably comprise at least one stem structure and at least one loop structure. The sequences which form the stem structure by base pairing may be of any length and preferably contain at least a portion of a sequence complementary to a target or template sequence. For example, the sequence of an oligonucleotide may be selected so as to form a hairpin structure at a temperature below the temperatures used in a synthesis or amplification reaction by first selecting a sequence at least partially complementary to a portion of a nucleic acid target or template sequence and then adding one or more nucleotides to the 5'-end of the oligonucleotide that are complementary to the nucleotides at the 3'-end of the oligonucleotide. At a reduced temperature, the complementary nucleotides at the 3' and 5' ends can base pair forming a stem structure. The number of complementary nucleotides to be added may be selected by determining the desired melting temperature of the stem structure. The melting temperature preferably is high enough that the oligonucleotide is in the hairpin structure when the reaction mixture is being prepared thereby preventing the oligonucleotide from mis-annealing to the target or template nucleic acid molecule but low enough such that all or portion of the oligonucleotides are capable of assuming a linear structure and annealing to the target or template at the appropriate point in the synthesis or amplification reaction. The selection of an appropriate melting temperature for the stem structure is routine for those of ordinary skill in the art.

The oligonucleotides of the present invention may incorporate more than one of the characteristics described above or combinations thereof. For example, an oligonucleotide may comprise one or more labels and/or one or more specificity enhancing groups and/or one or more hairpin structures.

In another aspect, one or more of the oligonucleotides of the present invention may be covalently or non-covalently attached to a support by any means known to those skilled in the art. Such support bound oligonucleotides may be used to carry out the methods of the present invention. For example, the detection or quantification of nucleic acid molecules may be accomplished on a support and/or the synthesis or amplification of nucleic acids may be accomplished on a support. Such a support may be solid or semisolid and may be made of any material known to those skilled in the art.

In one aspect, the present invention provides for reaction mixtures or compositions for use in a process for the synthesis and/or amplification of one or more nucleic acid molecules complementary to all or a portion of one or more nucleic acid target or template molecules of interest. In some preferred embodiments, the reaction mixture may comprise at least a first and preferably a first and a second oligonucleotide primer of the invention which primers may be the same or different and may contain the same or different labels and/or specificity enhancing groups. Such first primer preferably comprises at least one sequence which is at least partially complementary to said target or template nucleic acid and which primes synthesis of a first extension product that is complementary to all or a portion of said target or template nucleic acid. Such second oligonucleotide primer preferably comprise a sequence which is at least partially complementary to all or a portion of said first extension product and primes the synthesis of a second extension product which is at least partially complementary to all or a portion of said first extension product. In some embodiments, the reaction mixture may comprise one or more oligonucleotide primers of the invention, which may be the same or different, and which may contain one or more of the same or different labels and/or specificity enhancing groups. For example, the reaction mixture or composition may comprise more than one oligonucleotide primer, wherein at least one of said primers is in the form of a hairpin and another is not. In another aspect, one primer may be provided with a label that undergoes a detectable change in one or more properties upon hybridization and/or extension while a second primer may be in the form of a hairpin and/or comprise a specificity enhancing group. In another aspect, both the first and the second primer may be in the form of a hairpin and may also comprise labels and/or specificity enhancing groups as described above. Such reaction mixtures or compositions of the present invention may further comprise one or more components selected from a group consisting of one or more nucleotides, one or more DNA polymerases, one or more reverse transcriptases, one or more buffers or buffering salts, one or more target or template molecules and one or more products produced by a synthesis/amplification reaction of the present invention. Thus, the invention relates generally to compositions/reaction mixtures produced to carry out the invention and/or to composition/reaction mixtures resulting from carrying out the invention.

The present invention relates to a method for detecting the presence or absence of a nucleic acid molecule or for quantifying the amount of a nucleic acid molecule in a sample comprising:
(a) contacting a sample thought to contain one or more nucleic acid molecules with one or more oligonucleotides of the invention; and
(b) detecting the presence or absence or quantifying the amount of nucleic acid molecules in said sample.

In some embodiments, the oligonucleotide may be labeled and the detecting step may involve the detection of a change in one or more fluorescent or other detectable properties of a the labeled oligonucleotide of the present invention. In some embodiments, the fluorescent property which undergoes a change is the intensity of fluorescence. In some embodiments, an increase in fluorescence intensity is detected.

Preferably the oligonucleotides of the invention are incubated under conditions sufficient to allow hybridization of such oligonucleotides to the nucleic acid molecules in the sample. In a preferred aspect, the detection or quantification step includes a comparison of a control sample (without nucleic acid molecules present) to the sample containing nucleic acid molecules. Additional control samples containing known amounts of nucleic acid molecules may be used in accordance with the invention as a positive control for comparison purposes to determine the exact or approximate amount of the nucleic acid molecules present in the unknown sample.

In a related aspect, the invention relates to detection or quantification of nucleic acid molecules in a sample during or after nucleic acid synthesis or amplification. Thus, the invention relates to a method for detection or quantification of one or more nucleic acid molecules in a sample comprising:
(a) mixing one or more nucleic acid templates or target nucleic acid molecules of the sample with one or more oligonucleotides for the invention;
(b) incubating said mixture under conditions sufficient to synthesize or amplify one or more nucleic acid molecules complementary to all or a portion of said templates or target molecules, wherein said synthesized or amplified nucleic acid molecules comprise said oligonucleotide; and
(c) detecting or quantifying said synthesized or amplified nucleic acid molecules.

In some embodiments, the oligonucleotide may be labeled and the detecting step may involve the detection of a change in one or more fluorescent or other detectable properties of the labeled oligonucleotide of the present invention. In some embodiments, the fluorescent property which undergoes a change is the intensity of fluorescence. In some embodiments, an increase in fluorescence intensity is detected.

Conditions sufficient to synthesize or amplify one or more nucleic acid molecules complementary to all or a portion of said templates or target molecules preferably comprise incubating the template/oligonucleotide mixture in the presence of one or more nucleotides and one or more polymerases and/or reverse transcriptases (preferably DNA polymerases and most preferably thermostable DNA polymerases). In a most preferred aspect, the amplification process used is polymerase chain reaction (PCR) or RT PCR, although other amplification methods may be used in accordance with the invention. In this aspect of the invention, the detection/quantification step may be accomplished during amplification or synthesis or after synthesis or amplification is complete. For detection during an amplification reaction, a thermocycler capable of real time fluorescence detection may be used. Further, the nucleic acid synthesis or amplification method preferably produces double-stranded nucleic acid molecules (preferably double-stranded DNA/DNA or DNA/RNA molecules) and the presence or absence or amount of such double-stranded molecules may be determined by this method of the invention. In a preferred aspect, using the labeled oligonucleotides of the invention as a primer during synthesis or amplification, the labeled oligonucleotide primer is incorporated into the synthesized or amplified molecule thereby creating a labeled product molecule (which may be single-stranded or double-stranded). In another aspect, the synthesized or amplified nucleic acid molecules produced in accordance with the invention may contain one or more labels, which may be the same or different. In a preferred aspect, the detection or quantification step includes a comparison of a control sample to the sample containing the target/template nucleic acid molecules of interest. Additional control samples containing known amounts of target/template may be used as a positive control for comparison purposes and/or to determine the exact or approximate amount of target/template in an unknown sample.

More specifically, the invention is directed to a method for amplifying a double-stranded nucleic acid target molecule (e.g., DNA/DNA; RNA/RNA; or RNA/DNA), comprising:
(a) providing at least a first and a second primer, wherein said first primer is complementary to a sequence within or at or near the 3'-termini of a first strand of said nucleic molecule and said second primer is complementary to a sequence within or at or near the 3'-termini of the second strand of said nucleic acid molecule;
(b) hybridizing said first primer to said first strand and said second primer to said second strand in the presence of one or more of polymerases or reverse transcriptases, under conditions such that a third nucleic acid molecule complementary to all or a portion of said first strand and a fourth nucleic acid molecule complementary to all or a portion of said second strand are synthesized;
(c) denaturing said first and third strand, and said second and fourth strands; and
(d) repeating steps (a) to (c) one or more times, wherein one or more of said primers are oligonucleotides of the present invention.

In some embodiments, at least one of the primers comprises a label that undergoes a detectable change in one or more fluorescent or other detectable properties upon hybridization and/or extension. In some embodiments, at least one of the primers comprises a specificity enhancing group that renders the primer substantially less extendable when the 3'-nucleotide of the primer is not base paired with the target molecule. In some embodiments, one or more of the primers is in the form of a hairpin. In some embodiments, at least one of the primers is in the form of a hairpin and further comprises a detectable label and/or a specificity enhancing group.

In a further aspect, the present invention provides a method for the direct detection of amplification or synthesis products in which the detection may be performed without opening the reaction tube. This embodiment, the "closed-tube" format, reduces greatly the possibility of carryover contamination with amplification or synthesis products. The closed-tube method also provides for high throughput analysis of samples and may be automated. The closed-tube format significantly simplifies the detection process, eliminating the need for post-amplification or post-synthesis analysis such as gel electrophoresis or dot-blot analysis.

In another aspect, the invention relates to a method for hybridizing or binding one or more of the oligonucleotides of the invention with one or more nucleic acid molecules of interest comprising:
  (a) mixing one or more of said oligonucleotides with one or more of said nucleic acid molecules; and
  (b) incubating said mixture under conditions sufficient to hybridize or bind one or more of said oligonucleotides with one or more of said nucleic acid molecules.

In a preferred aspect, at least one or more of the oligonucleotides used in this method are hairpins and more preferably, the one or more oligonucleotides are hairpin molecules comprising one or more specificity enhancing groups and/or one or more labels.

The invention also relates to methods of synthesis or amplification of one or more nucleic acid molecules comprising:
  (a) mixing one or more templates or target nucleic acid molecules with one or more oligonucleotides of the invention; and
  (b) incubating said mixture under conditions sufficient to synthesize or amplify one or more nucleic acid molecules complementary to all or a portion of said templates or target molecules.

In a preferred aspect, the oligonucleotides are hairpins and more preferably are hairpin molecules comprising one or more specificity enhancing groups and/or one or more labels. Conditions sufficient to synthesize or amplify one or more nucleic acid molecules complementary to all or a portion of said templates or target molecules preferably comprise incubating the templates/oligonucleotide mixture (e.g., the template-oligonucleotide complex) in the presence of one or more nucleotides and one or more polymerases and/or one or more reverse transcriptases (preferably DNA polymerases and most preferably thermostable DNA polymerases). In a most preferred aspect, the amplification process used is polymerase chain reaction (PCR) or RT PCR, although other amplification methods may be used in accordance with the invention. Further, the nucleic acid synthesis or amplification methods preferably produces double stranded nucleic acid molecules (preferably double stranded DNA/DNA or DNA/RNA molecules). Use of the oligonucleotides of the invention allows for more efficient synthesis and/or amplification of nucleic acid molecules.

More specifically, the invention is directed to a method for amplifying a double stranded nucleic acid target molecules comprising:
  (a) providing a first and second primer, wherein said first primer is complementary to a sequence within or at or near the 3'-termini of the first strand of said nucleic acid molecule and said second primer is complementary to a sequence within or at or near the 3' termini of the second strand of said nucleic acid molecule;
  (b) hybriding said first primer to said first strand and said second primer to said second strand in the presence of one or more polymerases or reverse transcriptases, under conditions such that a third nucleic acid molecule complementary to all or a portion of said first strand and a fourth nucleic acid molecule complementary to all or a portion of said second strand are synthesized;
  (c) denaturing said first and third strands, and said second and first strands; and
  (d) repeating steps (a) to (c) one or more times, wherein one or more of said primers are oligonucleotides of the present invention.

In one embodiment, the oligonucleotides of the invention used are hairpins, and preferably are hairpins comprising one or more specificity enhancing groups and/or one or more labels.

The invention also provides the embodiments of the above methods wherein the nucleic acid molecule to be detected/quantified/amplified/synthesized is an RNA or a DNA molecule, and wherein such molecule is either single-stranded or double-stranded.

The invention also provides the embodiments of the above methods wherein one or a number of the primers or oligonucleotides of the present invention comprise at least one nucleotide derivative. Examples of such derivatives include, but are not limited to, a deoxyinosine residue, a thionucleotide, a peptide nucleic acid and the like.

The invention also provides the embodiment of the above methods wherein the nucleic acid target or template molecule is polyadenylated at its 3' end (e.g., poly(A) RNA or mRNA), and/or at least one of the primers or oligonucleotides of the invention contains a poly(T) sequence, and/or at least one of the other of the primers or oligonucleotides of the invention contains at least one deoxyinosine residue. In a related aspect, the template or target nucleic acid is an mRNA molecule, at least one primer/oligonucleotide is labeled and comprises a poly(T) sequence and at least one primer/oligonucleotide comprises at least one deoxyinosine residue.

As will be further appreciated, the labeled oligonucleotide sequences of the invention may be employed in other amplification methods, such as those involving the application of PCR to the amplification of cDNA-ends derived from mRNAs using a single gene specific primer. Thus, labeled oligonucleotides of the invention can be used in methods such as "RT-PCR," "5'-RACE," "anchor PCR" and "one-sided PCR," which facilitate the capture of sequence from 5'-ends of mRNA. The methods of the invention are adaptable to many methods for amplification of nucleic acid sequences, including PCR, LCR, SDA and NASBA, and other amplification systems known to those of ordinary skill in the art.

In another aspect of the invention, the invention is directed to a method for determining the activity or amount of a polymerase in a sample, comprising amplifying a nucleic acid molecule, comprising:
  (a) providing a first and second primer, wherein said first primer is complementary to a sequence within or at or near the 3'-termini of the first strand of said nucleic acid molecule and said second primer is complementary to a sequence within or at or near the 3'-termini of the second strand of said nucleic acid molecule;
  (b) hybridizing said first primer to said first strand and said second primer to said second strand in the presence of said polymerase, under conditions such that a third nucleic acid molecule complementary to all or a portion of said first strand and a fourth nucleic acid molecule complementary to all or a portion of said second strand are synthesized;

(c) denaturing said first and third strand, and said second and fourth strands; and (d) repeating steps (a) to (c) one or more times; and (e) detecting the amplification product, wherein at least one of the primers are oligonucleotides of the present invention, and wherein the amount of the amplification product produced is indicative of the activity or amount of the polymerase.

In some embodiments, the amount of the amplification product produced is determined by detecting a change in one or more fluorescent or other detectable properties of an incorporated detectable label.

Generally, the invention thus relates to a method for determining the activity or the amount of polymerase or reverse transcriptase in a sample comprising:

(a) mixing a sample thought to contain a polymerase or reverse transcriptase with one or more nucleic acid templates and one or more labeled oligonucleotides of the invention;

(b) incubating said mixture under conditions sufficient to allow synthesis or amplification of one or more nucleic acid molecules complementary to all or a portion of said templates, wherein said synthesized or amplified nucleic acid molecules comprise said oligonucleotides; and (c) determining the activity or amount of said polymerase or reverse transcriptase in said sample based on detection of one or more detectable labels.

In another aspect, the invention relates to quenching background fluorescence during detection of nucleic acid molecules or polymerases in accordance with the methods of the invention. In this aspect of the invention, one or more quenching agents which bind one or more labeled single-stranded nucleic acid molecules are used to quench the fluorescence produced by such single-stranded molecules. In a preferred aspect, the quenching agent is specific for single-stranded molecules and will not substantially interact with double-stranded labeled nucleic acid molecules. Thus, fluorescently labeled oligonucleotides of the invention will be quenched or substantially quenched in the presence of such agents. Upon interaction with the target molecule or during amplification or synthesis reactions, the double-stranded nucleic acid molecule formed which comprise the fluorescently labeled oligonucleotides of the invention will not substantially interact with such agents and thus will not be quenched by such agents. This aspect of the invention thus allows for reduced background fluorescence and enhanced detection of target nucleic acid molecules in the methods of the invention. Preferred quenchers for use in the invention include one or more single-stranded binding proteins. In another aspect, such quenching agents may include blocking oligonucleotides which contain one or more quenchers, for example, DABCYL. In another aspect, the quenching moiety may be part of the oligonucleotide of the invention. For example, one or more quenching moieties may be incorporated into one or more stem structures of the hairpin of the invention. Such stem structures may also incorporate one or more labels and in the hairpin configuration, the quenching moieties reduce the level of background activity of the label. Upon denaturation (unfolding) of the stem structure, the quenching of the label is reduced or prevented.

In another embodiment, the invention relates to a composition comprising one or more labeled oligonucleotide of the invention, wherein the label is a detectable label, and wherein the oligonucleotide is selected from the group consisting of DNA and RNA. The labeled oligonucleotides of the invention may be primers and/or probes, depending on the use. The compositions of the invention may further comprise one or more components selected from the group consisting of one or more polymerases, one or more quenching agents, one or more nucleotides, one or more nucleic acid molecules (which may be templates or nucleic acid molecules which may comprise one or more oligonucleotides of the invention), and one or more buffering salts.

In another embodiment of the invention, the label is a member of a FRET pair. In this embodiment, one or more labeled oligonucleotides of the invention containing a single or multiple members of a FRET pair internally, and/or, at or near the 3' and/or 5' end. In a preferred aspect, the labeled moiety is one or more fluorescent moieties whose emission may then be measured to assess the progress of the reaction.

The present invention also relates to kits for the detection or measurement of nucleic acid synthesis or amplification products or for the measurement or detection of nucleic acid molecules of the invention. Such kits may be diagnostic kits where the presence of the nucleic acid being amplified or synthesized is correlated with the presence or absence of a disease or disorder. Kits of the invention may also be used to detect or determine activity or amount of a polymerase in a sample. In addition, kits of the invention may be used to carry out synthesis, amplification or other extension reactions using the oligonucleotides of the invention. Preferred kits of the invention may comprise one or more containers (such as vials, tubes, and the like) configured to contain the reagents used in the methods of the invention and optionally may contain instructions or protocols for using such reagents. The kits of the invention may comprise one or more components selected from the group consisting of one or more oligonucleotides of the invention (including probes and/or primers), one or more DNA polymerases, such as a thermostable polymerase, one or more reverse transcriptases, or any other DNA or RNA polymerase, one or more agents capable of quenching one or more of the labels, one or more buffers or buffering salts, one or more nucleotides, one or more target/template molecules (which may used for determining reaction performance, i.e., control reactions) and other reagents for analysis or further manipulation of the products or intermediates produced by the methods of the invention. Such additional components may include components used for cloning and/or sequencing and components or equipment needed for the detection or quantification of the nucleic acid molecule of interest.

The invention also relates to any of the products or intermediates (e.g, nucleic acid molecules) produced by carrying out the methods of the invention. The invention also relates to vectors or host cells containing such products or intermediates produced by the methods of the invention. Introduction of such vectors into host cells may be accomplished using any of the cloning and transformation techniques known to those skilled in the art.

DETAILED DESCRIPTION OF THE INVENTION

Definitions and Abbreviations

Figure 1:
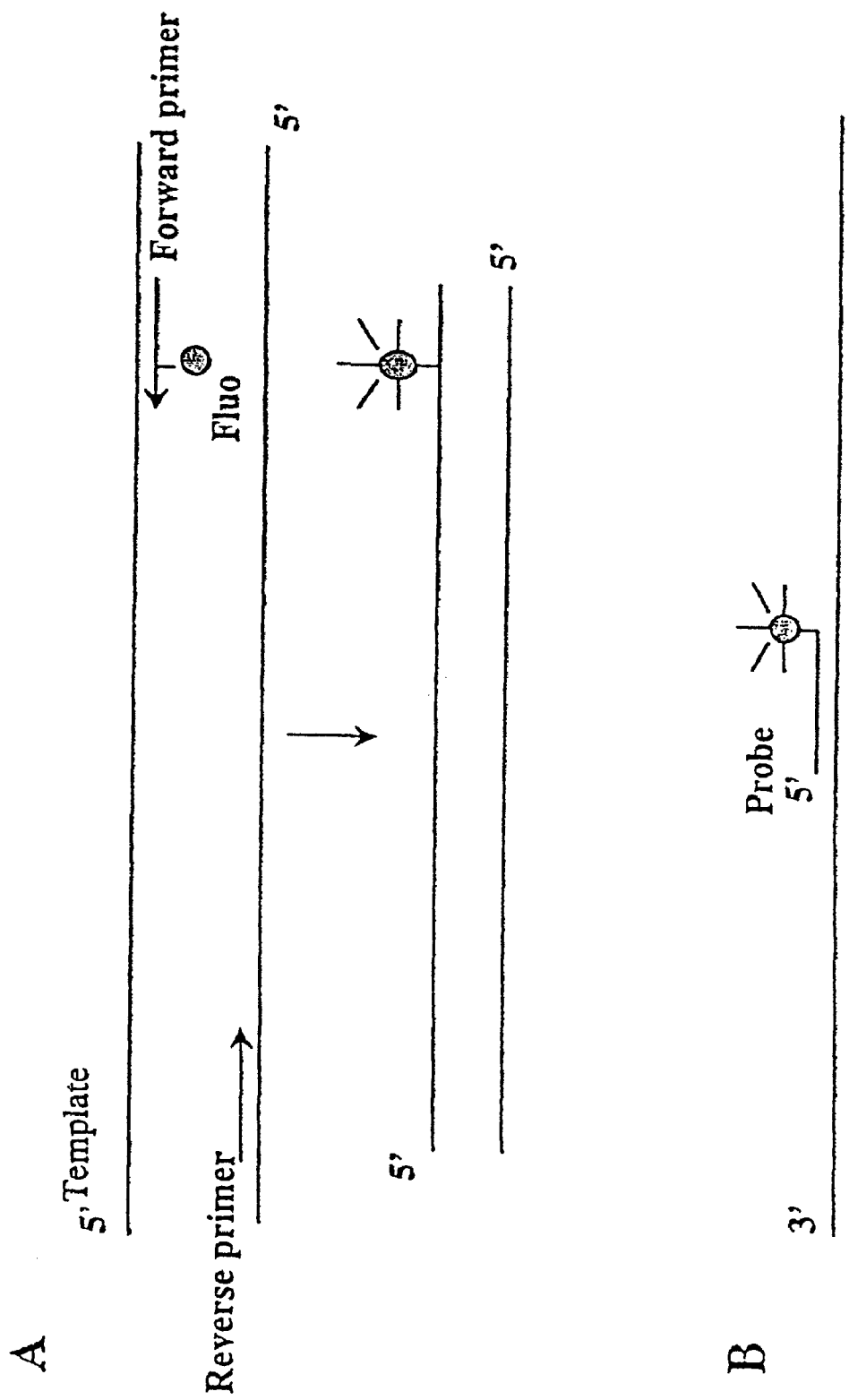
FIG. 1 is a schematic representation of the homogeneous/real-time detection system of the invention. A change in one or more fluorescent or other detectable properties can be detected either through the incorporation of the labeled primer into the double-stranded amplification product (A), or through the direct hybridization of the labeled probe to the nucleic acid target (B). In accordance with the invention, the nucleic acid molecules detected or quantified can be a synthesized or amplified product or a nucleic acid molecule found in nature. Such nucleic acid molecules may be single or double stranded and can be RNA, DNA or RNA/DNA hybrids. In accordance with the invention, any one or more labels (which may be the same or different) may be used.

In the description that follows, a number of terms used in recombinant DNA technology are extensively utilized. As used herein, the following terms shall have the abbreviations indicated:

ASP, allele-specific polymerase chain reaction
bp, base pairs
DAB or DABCYL, 4-(4'-dimethylaminophenylazo) benzoic acid
EDANS, 5-(2'-aminoethyl) aminonapthalene-1-sulfonic acid
FAM or Flu, 5-carboxyfluorescein
JOE, 2'7'-dimethoxy-4'5'-dichloro-6-carboxyfluorescein
HPLC, high-performance liquid chromatography
NASBA, nucleic acid sequence-based amplification
Rhod, rhodamine
ROX, 6-carboxy-X-rhodamine
R6G, 6-carboxyrhodamine
TAMRA, N,N,N',N'-tetramethyl-6-carboxyrhodamine Amplification. As used herein, "amplification" refers to any in vitro method for increasing the number of copies of a nucleotide sequence with the use of a polymerase. Nucleic acid amplification results in the incorporation of nucleotides into a nucleic acid (e.g., DNA) molecule or primer thereby forming a new nucleic acid molecule complementary to the nucleic acid template. The formed nucleic acid molecule and its template can be used as templates to synthesize additional nucleic acid molecules. As used herein, one amplification reaction may consist of many rounds of nucleic acid synthesis. Amplification reactions include, for example, polymerase chain reactions (PCR). One PCR reaction may consist of 5 to 100 "cycles" of denaturation and synthesis of a nucleic acid molecule.

Specificity enhancing group. As used herein "specificity enhancing group" refers to any molecule or group of molecules that causes an oligonucleotide of the present invention to be substantially less extendable when the 3'-most nucleotide of the oligonucleotide is substantially not base paired with a nucleotide on the nucleic acid target/template molecule. Any type of group may be used. Preferred examples include, but are not limited to, fluorescent groups, modified nucleotides, small molecules, haptens and the like. Specificity enhancing groups may be attached at any position of the oligonucleotide so long as they make the oligonucleotide substantially less extendable when the 3'-terminal nucleotide of the oligonucleotide is substantially not base paired with the corresponding nucleotide of the target/template nucleic acid. Such groups are preferably attached to the primer at or near the 3'-end of the primer but may be attached at other positions as well. Preferably, they are attached to one or more of the 25 bases adjacent to the 3'-end of the primer. In some preferred embodiments, such groups may be attached to one or more of the 20 bases adjacent to the 3'-end of the oligonucleotide, or to the 15 bases adjacent to the 3-end or to the 10 base pairs adjacent to the 3'-end or, most preferably to one or more of the five bases adjacent to the 3'-end of the oligonucleotide. In addition, specificity enhancing groups may be attached to the 3'-most nucleotide so long as the presence of the group does not prevent or inhibit the extension of the primer when the 3'-most nucleotide of the primer is complementary to the corresponding nucleotide on the target/template molecule more than the extension is inhibited when the 3'-most nucleotide is substantially not base paired to the target/template. Any group that can decrease the stability of the duplex formed by the primer and template when the 3'-most nucleotide of the primer is not complementary the corresponding nucleotide of the target/template and/or any group that can make a polymerase less efficient at extending the 3'-end of the oligonucleotide when the 3'-most nucleotide is not complementary to the corresponding nucleotide of the template/target may be used to practice the present invention. In some embodiments, the specificity enhancing groups of the invention may be modified nucleotides incorporated into the sequence of the primer. Such modifications may be made at the base, sugar or phosphate portion of the nucleotide and include but are not limited to phophothioate nucleotides, phosphonate nucleotides, peptide nucleic acids and the like.

Polymerase. As used herein "polymerase" refers to any enzyme having a nucleotide polymerizing activity. Polymerases (including DNA polymerases and RNA polymerases) useful in accordance with the present invention include, but are not limited to, *Thermus thermophilus* (Tth) DNA polymerase, *Thermus aquaticus* (Taq) DNA polymerase, *Thermotoga neopolitana* (Tne) DNA polymerase, *Thermotoga maritima* (Tma) DNA polymerase, *Thermococcus litoralis* (Tli or VENT™) DNA polymerase, *Pyrococcus furiosus* (Pfu) DNA polymerase, DEEPVENT™ DNA polymerase, *Pyrococcus woosii* (Pwo) DNA polymerase, *Bacillus sterothermophilus* (Bst) DNA polymerase, *Bacillus caldophilus* (Bca) DNA polymerase, Sulfobus acidocaldarius (Sac) DNA polymerase, *Thermoplasma acidophilum* (Tac) DNA polymerase, *Thermus flavus* (Tfl/Tub) DNA polymerase, *Thermus ruber* (Tru) DNA polymerase, *Thermus brockianus* (DYNAZYME™) DNA polymerase, *Methanobacterium thermoautotrophicum* (Mth) DNA polymerase, mycobacterium DNA polymerase (Mtb, Mlep), and mutants, and variants and derivatives thereof. RNA polymerases such as T3, T5 and SP6 and mutants, variants and derivatives thereof may also be used in accordance with the invention. Generally, any type I DNA polymerase may be used in accordance with the invention although other DNA polymerases may be used including, but not limited to, type III or family A, B, C etc. DNA polymerases.

Polymerases used in accordance with the invention may be any enzyme that can synthesize a nucleic acid molecule from a nucleic acid template, typically in the 5' to 3' direction. The nucleic acid polymerases used in the present invention may be mesophilic or thermophilic, and are preferably thermophilic. Preferred mesophilic DNA polymerases include T7 DNA polymerase, T5 DNA polymerase, Klenow fragment DNA polymerase, DNA polymerase III and the like. Preferred thermostable DNA polymerases that may be used in the methods of the invention include Taq, Tne, Tma, Pfu, Tfl, Tth, Stoffel fragment, VENTT™ and DEEPVENT™ DNA polymerases, and mutants, variants and derivatives thereof (U.S. Pat. No. 5,436,149; U.S. Pat. No. 4,889,818; U.S. Pat. No. 4,965,188; U.S. Pat. No. 5,079,352; U.S. Pat. No. 5,614,365; U.S. Pat. No. 5,374,553; U.S. Pat. No. 5,270,179; U.S. Pat. No. 5,047,342; U.S. Pat. No. 5,512,462; WO 92/06188; WO 92/06200; WO 96/10640; Barnes, W. M., *Gene* 112:29-35 (1992); Lawyer, F. C., et al., *PCR Meth. Appl.* 2:275-287 (1993); Flaman, J.-M, et al., *Nucl. Acids Res.* 22(15):3259-3260 (1994)). For amplification of long nucleic acid molecules (e.g., nucleic acid molecules longer than about 3-5 Kb in length), at least two DNA polymerases (one substantially lacking 3' exonuclease activity and the other having 3' exonuclease activity) are typically used. See U.S. Pat. No. 5,436,149; and U.S. Pat. No. 5,512,462; Barnes, W. M., *Gene* 112: 29-35 (1992), the disclosures of which are incorporated herein in their entireties. Examples of DNA polymerases substantially lacking in 3' exonuclease activity include, but are not limited to, Taq, Tne(exo$^-$), Tma(exo$^-$), Pfu (exo$^-$), Pwo(exo$^-$) and Tth DNA polymerases, and mutants, variants and derivatives thereof.

DNA polymerases for use in the present invention may be obtained commercially, for example, from Life Technologies, Inc. (Rockville, Md.), Pharmacia (Piscataway, N.J.), Sigma (St. Louis, Mo.) and Boehringer Mannheim. Preferred DNA polymerases for use in the present invention include Tsp DNA polymerase from Life Technologies, Inc.

Enzymes for use in the compositions, methods and kits of the invention include any enzyme having reverse transcriptase activity. Such enzymes include, but are not limited to, retroviral reverse transcriptase, retrotransposon reverse transcriptase, hepatitis B reverse transcriptase, cauliflower mosaic virus reverse transcriptase, bacterial reverse transcriptase, Tth DNA polymerase, Taq DNA polymerase (Saiki, R. K., et al., *Science* 239:487-491 (1988); U.S. Pat. Nos. 4,889,818 and 4,965,188), Tne DNA polymerase (WO 96/10640), Tma DNA polymerase (U.S. Pat. No. 5,374,553) and mutants, fragments, variants or derivatives thereof (see, e.g., commonly owned, co-pending U.S. patent application Ser. Nos. 08/706,702 and 08/706,706, both filed Sep. 9, 1996, which are incorporated by reference herein in their entireties). As will be understood by one of ordinary skill in the art, modified reverse transcriptases and DNA polymerase having RT activity may be obtained by recombinant or genetic engineering techniques that are well-known in the art. Mutant reverse transcriptases or polymerases can, for example, be obtained by mutating the gene or genes encoding the reverse transcriptase or polymerase of interest by site-directed or random mutagenesis. Such mutations may include point mutations, deletion mutations and insertional mutations. Preferably, one or more point mutations (e.g., substitution of one or more amino acids with one or more different amino acids) are used to construct mutant reverse transcriptases or polymerases for use in the invention. Fragments of reverse transcriptases or polymerases may also be obtained by deletion mutation by recombinant techniques that are well-known in the art, or by enzymatic digestion of the reverse transcriptase(s) or polymerase(s) of interest using any of a number of well-known proteolytic enzymes.

Preferred enzymes for use in the invention include those that are reduced or substantially reduced in RNase H activity. Such enzymes that are reduced or substantially reduced in RNase H activity may be obtained by mutating the RNase H domain within the reverse transcriptase of interest, preferably by one or more point mutations, one or more deletion mutations, and/or one or more insertion mutations as described above. By an enzyme "substantially reduced in RNase H activity" is meant that the enzyme has less than about 30%, less than about 25%, less than about 20%, more preferably less than about 15%, less than about 10%, less than about 7.5%, or less than about 5%, and most preferably less than about 5% or less than about 2%, of the RNase H activity of the corresponding wildtype or RNase H$^+$ enzyme such as wildtype Moloney Murine Leukemia Virus (M-MLV), Avian Myeloblastosis Virus (AMV) or Rous Sarcoma Virus (RSV) reverse transcriptases. The RNase H activity of any enzyme may be determined by a variety of assays, such as those described, for example, in U.S. Pat. No. 5,244,797, in Kotewicz, M. L., et al., *Nucl. Acids Res.* 16:265 (1988), in Gerard, G. F., et al., *FOCUS* 14(5):91 (1992), and in U.S. Pat. No. 5,668,005, the disclosures of all of which are fully incorporated herein by reference.

Polypeptides having reverse transcriptase activity for use in the invention may be obtained commercially, for example from Life Technologies, Inc. (Rockville, Md.), Pharmacia (Piscataway, N.J.), Sigma (Saint Louis, Mo.) or Boehringer Mannheim Biochemicals (Indianapolis, Ind.). Alternatively, polypeptides having reverse transcriptase activity may be isolated from their natural viral or bacterial sources according to standard procedures for isolating and purifying natural proteins that are well-known to one of ordinary skill in the art (see, e.g., Houts, G. E., et al., *J. Virol.* 29:517 (1979)). In addition, the polypeptides having reverse transcriptase activity may be prepared by recombinant DNA techniques that are familiar to one of ordinary skill in the art (see, e.g., Kotewicz, M. L., et al., *Nucl. Acids Res.* 16:265 (1988); Soltis, D. A., and Skalka, A. M., *Proc. Natl. Acad. Sci. USA* 85:3372-3376 (1988)).

Preferred polypeptides having reverse transcriptase activity for use in the invention include M-MLV reverse transcriptase, RSV reverse transcriptase, AMV reverse transcriptase, Rous Associated Virus (RAV) reverse transcriptase, Myeloblastosis Associated Virus (MAV) reverse transcriptase and Human Immunodeficiency Virus (HIV) reverse transcriptase, and others described in WO 98/47921 and derivatives, variants, fragments or mutants thereof, and combinations thereof. In a further preferred embodiment, the reverse transcriptases are reduced or substantially reduced in RNase H activity, and are most preferably selected from the group consisting of M-MLV H$^-$ reverse transcriptase, RSV H$^-$ reverse transcriptase, AMV H$^-$ reverse transcriptase, RAV H$^-$ reverse transcriptase, MAV H$^-$ reverse transcriptase and HIV H$^-$ reverse transcriptase, and derivatives, variants, fragments or mutants thereof, and combinations thereof. Reverse transcriptases of particular interest include AMV RT and M-MLV RT, and more preferably AMV RT and M-MLV RT having reduced or substantially reduced RNase H activity (preferably AMV RT αH$^-$/BH$^+$ and M-MLV RT H$^-$). The most preferred reverse transcriptases for use in the invention include SuperScript™, SuperScript™ II, ThermoScript™ and ThermoScript™ II available from Life Technologies, Inc. See generally, WO 98/47921, U.S. Pat. Nos. 5,244,797 and 5,668,005, the entire contents of each of which are herein incorporated by reference.

Hairpin. As used herein, the term "hairpin" is used to indicate the structure of an oligonucleotide in which one or more portions of the oligonucleotide form base pairs with one or more other portions of the oligonucleotide. When the two portions are base paired to form a double stranded portion of the oligonucleotide, the double stranded portion may be referred to as a stem. Thus, depending on the number of complementary portions used, a number of stems (preferably 1-10) may be formed. Additionally, formation of the one or more stems preferably allows formation of one or more loop structures in the hairpin molecule. In one aspect, any one or more of the loop structures may be cut or nicked at one or more sites within the loop or loops but preferably at least one loop is not so cut or nicked. The sequence of the oligonucleotide may be selected so as to vary the number of nucleotides which base pair to form the stem from about 3 nucleotides to about 100 or more nucleotides, from about 3 nucleotides to about 50 nucleotides, from about 3 nucleotides to about 25 nucleotides, and from about 3 to about 10 nucleotides. In addition, the sequence of the oligonucleotide may be varied so as to vary the number of nucleotides which do not form base pairs from 0 nucleotides to about 100 or more nucleotides, from 0 nucleotides to about 50 nucleotides, from 0 nucleotides to about 25 nucleotides or from 0 to about 10 nucleotides. The two portions of the oligonucleotide which base pair may be located anywhere or at any number of locations in the sequence of the oligonucleotide. In some embodiments, one base-pairing-portion of the oligonucleotide may include the 3'-terminal of the oligonucleotide. In some embodiments, one base-pairing-portion may include the 5-terminal of the oligonucleotide. In some embodiments, one base-pairing-portion of the oligonucleotide may include the 3'-terminal while the other base-pairing-portion may include the 5'-terminal and, when base paired, the stem of the oligonucleotide is blunt ended. In other embodiments, the location of the base pairing portions of the oligonucleotide may be selected so as to form a 3'-overhang, a 5'-overhang and/or may be selected so that neither the 3'-nor the 5'-most nucleotides are involved in base pairing.

Hybridization. As used herein, the terms "hybridization" and "hybridizing" refer to the pairing of two complementary single-stranded nucleic acid molecules (RNA and/or DNA) to give a double-stranded molecule. As used herein, two nucleic acid molecules may be hybridized, although the base pairing is not completely complementary. Accordingly, mismatched bases do not prevent hybridization of two nucleic acid molecules provided that appropriate conditions, well known in the art, are used.

Incorporating. The term "incorporating" as used herein means becoming a part of a DNA or RNA molecule or primer.

Nucleotide. As used herein "nucleotide" refers to a base-sugar-phosphate combination. Nucleotides are monomeric units of a nucleic acid sequence (DNA and RNA). The term nucleotide includes mono-, di- and triphosphate forms of deoxyribonucleosides and ribonucleosides and their derivatives. The term nucleotide particularly includes deoxyribonucleoside triphosphates such as dATP, dCTP, dITP, dUTP, dGTP, dTTP, or derivatives thereof. Such derivatives include, for example, [αS]dATP, 7-deaza-dGTP and 7-deaza-dATP. The term nucleotide as used herein also refers to dideoxyribonucleoside triphosphates (ddNTPs) and their derivatives. Illustrated examples of dideoxyribonucleoside triphosphates include, but are not limited to, ddATP, ddCTP, ddGTP, ddITP, and ddTTP. According to the present invention, a "nucleotide" may be unlabeled or detectably labeled by well known techniques. Detectable labels include, for example, radioactive isotopes, fluorescent labels, chemiluminescent labels, bioluminescent labels and enzyme labels.

Oligonucleotide. As used herein, "oligonucleotide" refers to a synthetic or biologically produced molecule comprising a covalently linked sequence of nucleotides which may be joined by a phosphodiester bond between the 3' position of the pentose of one nucleotide and the 5' position of the pentose of the adjacent nucleotide. Oligonucleotide as used herein is seen to include natural nucleic acid molecules (i.e., DNA and RNA) as well as non-natural or derivative molecules such as peptide nucleic acids, phophothioate containing nucleic acids, phosphonate containing nucleic acids and the like. In addition, oligonucleotides of the present invention may contain modified or non-naturally occurring sugar residues (i.e., arabainose) and/or modified base residues. Oligonucleotide is seen to encompass derivative molecules such as nucleic acid molecules comprising various natural nucleotides, derivative nucleotides, modified nucleotides or combinations thereof. Thus any oligonucleotide or other molecule useful in the methods of the invention are contemplated by this definition. Oligonucleotides of the present invention may also comprise blocking groups which prevent the interaction of the molecule with particular proteins, enzymes or substrates.

Primer. As used herein, "primer" refers to a synthetic or biologically produced single-stranded oligonucleotide that is extended by covalent bonding of nucleotide monomers during amplification or polymerization of a nucleic acid molecule. Nucleic acid amplification often is based on nucleic acid synthesis by a nucleic acid polymerase or reverse transcriptase. Many such polymerases or reverse transcriptases require the presence of a primer that can be extended to initiate such nucleic acid synthesis. A primer is typically 11 bases or longer; most preferably, a primer is 17 bases or longer, although shorter or longer primers may be used depending on the need. As will be appreciated by those skilled in the art, the oligonucleotides of the invention may be used as one or more primers in various extension, synthesis or amplification reactions.

Probe. As used herein, "probe" refers to synthetic or biologically produced nucleic acids (DNA or RNA) which, by design or selection, contain specific nucleotide sequences that allow them to hybridize, under defined stringencies, specifically (i.e., preferentially) to target nucleic acid sequences. As will be appreciated by those skilled in the art, the oligonucleotides of the present invention may be used as one or more probes and preferably may be used as probes for the detection or quantification of nucleic acid molecules.

Substantially less extendable. As used herein, "substantially less extendable" is used to characterize an oligonucleotide that is inefficiently extended or not extended in an extension and/or amplification reaction when the 3'-most nucleotide of the oligonucleotide is not complementary to the corresponding base of a target/template nucleic acid. Preferably, an oligonucleotide is substantially less extendable as a result of the presence of a specificity enhancing group on the oligonucleotide. In this event, an oligonucleotide is substantially less extendable when the oligonucleotide is not extended or is extended by a lesser amount and/or at a slower rate than an oligonucleotide lacking the specificity enhancing group but having an otherwise identical structure. Those skilled in the art can readily determine if an oligonucleotide is substantially less extendable by conducting an extension reaction using an oligonucleotide containing a specificity enhancing group and comparing the extension to the extension of an oligonucleotide of the same structure but lacking the specificity enhancing group. Under identical extension conditions, (e.g., melting temperature and time, annealing temperature and time, extension temperature and time, reactant concentrations and the like), a substantially less extendable oligonucleotide will produce less extension product when the 3'-most nucleotide of the oligonucleotide is not complementary to the corresponding nucleotide on a target/template nucleic acid than will be produced by an oligonucleotide lacking a specificity enhancing group but having an otherwise identical structure. Alternatively, one skilled in the art can determine if an oligonucleotide is substantially less extendable by conducting allele specific PCR with a first set of oligonucleotides at least one of which comprises one or more specificity enhancing groups and with a second set of oligonucleotides lacking specificity enhancing groups but otherwise of identical structure to those of the first set. Then a determination is separately made for each set of primers of the difference in the amount of product made and/or the rate at which the product is made with the oligonucleotide having the 3'-nucleotide complementary to the corresponding nucleotide on a target/template nucleic acid to the amount of product made and/or the rate at which the product is made with an oligonucleotide having the 3'-nucleotide not complementary to the corresponding nucleotide on a target/template nucleic acid. Substantially less extendable oligonucleotides will produce a larger difference in amount of product made and/or rate at which product is made between 3'-complementary and 3'-not-complementary oligonucleotides. Preferably the difference in the amount of product made and/or rate at which product is made using oligonucleotides containing specificity enhancing groups will be between from about 1.1 fold to about 1000 fold larger than the difference obtained using primers lacking specificity enhancing groups, or from about 1.1 fold to about 500 fold larger, or from about 1.1 fold to about 250 fold larger, or from about 1.1 fold to about 100 fold larger, or from about 1.1 fold to about 50 fold larger, or from about 1.1 to about 25 fold larger, or from about 1.1 to about 10 fold larger, or from about 1.1 fold to about 5 fold or from about 1.1 fold to about 2 fold larger. The amount of product can be determined using any methodology known to those of skill in the art, for example, by running the product on an agarose gel and staining with ethidium bromide and comparing to known amounts of similarly treated nucleic acid standards. The amount of product may be determined at any convenient time point in the allele specific PCR. One convenient way to compare the rate of formation of product is to compare the number of cycles required to form a specified amount of product in a PCR. A determination is separately made for each set of primers of the difference between the number of cycles required to make a given amount of product with the oligonucleotide having the 3'-nucleotide complementary to the corresponding nucleotide on a target/template nucleic acid and the number of cycles required to make the same amount of product with an oligonucleotide having the 3'-nucleotide not complementary to the corresponding nucleotide on a target/template nucleic acid. Substantially less extendable oligonucleotides will produce a larger difference in the number of cycles required to produce a specified amount of product between 3'-complementary and 3'-not-complementary oligonucleotides. The amount of product made can be determined using any means known to those skilled in the art, for example, by determining the fluorescence intensity of a labeled product using a thermocycler adapted to perform real time fluorescence detection. Preferably the difference between the number of cycles required to make a specified amount of product using oligonucleotides containing specificity enhancing groups will be between from about 1.05 fold to about 100 fold larger than the difference obtained using primers lacking specificity enhancing groups, or from about 1.05 fold to about 50 fold larger, or from about 1.05 fold to about 25 fold larger, or from about 1.05 fold to about 10 fold larger, or from about 1.05 fold to about 5 fold larger, or from about 1.05 to about 2.5 fold larger, or from about 1.05 to about 1.5 fold larger, or from about 1.05 fold to about 1.2 fold larger.

Support. As used herein a "support" may be any material or matrix suitable for attaching the oligonucleotides of the present invention or target/template nucleic acid sequences. Such oligonucleotides and/or sequences may be added or bound (covalently or non-covalently) to the supports of the invention by any technique or any combination of techniques well known in the art. Supports of the invention may comprise nitrocellulose, diazocellulose, glass, polystrene (including microtitre plates), polyvinylchloride, polypropylene, polyethylene, dextran, Sepharose, agar, starch and nylon. Supports of the invention may be in any form or configuration including beads, filters, membranes, sheets, frits, plugs, columns and the like. Solid supports may also include multi-well tubes (such as microtitre plates) such as 12-well plates, 24-well plates, 48-well plates, 96-well plates, and 384-well plates. Preferred beads are made of glass, latex or a magnetic material (magnetic, paramagnetic or superparamagnetic beads).

In a preferred aspect, methods of the invention may be used in conjunction with arrays of nucleic acid molecules (RNA or DNA). Arrays of nucleic acid template/target or arrays of oligonucleotides of the invention are both contemplated in the methods of the invention. Such arrays may be formed on microplates, glass slides or standard blotting membranes and may be referred to as microarrays or gene-chips depending on the format and design of the array. Uses for such arrays include gene discovery, gene expression profiling and genotyping (SNP analysis, pharmacogenomics, toxicogenetics).

Synthesis and use of nucleic acid arrays and generally attachment of nucleic acids to supports have been described (see for example, U.S. Pat. No. 5,436,327, U.S. Pat. No. 5,800,992, U.S. Pat. No. 5,445,934, U.S. Pat. No. 5,763,170, U.S. Pat. No. 5,599,695 and U.S. Pat. No. 5,837,832). An automated process for attaching various reagents to positionally defined sites on a substrate is provided in Pirrung et al. U.S. Pat. No. 5,143,854 and Barrett et al. U.S. Pat. No. 5,252,743.

Essentially, any conceivable support may be employed in the invention. The support may be biological, nonbiological, organic, inorganic, or a combination of any of these, existing as particles, strands, precipitates, gels, sheets, tubing, spheres, containers, capillaries, pads, slices, films, plates, slides, etc. The support may have any convenient shape, such as a disc, square, sphere, circle, etc. The support is preferably flat but may take on a variety of alternative surface configurations. For example, the support may contain raised or depressed regions on which one or more methods of the invention may take place. The support and its surface preferably form a rigid support on which to carry out the reactions described herein. The support and its surface is also chosen to provide appropriate light-absorbing characteristics. For instance, the support may be a polymerized Langmuir Blodgett film, functionalized glass, Si, Ge, GaAs, GaP, $SiO_2$, $SIN_4$, modified silicon, or any one of a wide variety of gels or polymers such as (poly)tetrafluoroethylene, (poly)vinylidenedifluoride, polystyrene, polycarbonate, or combinations thereof. Other support materials will be readily apparent to those of skill in the art upon review of this disclosure. In a preferred embodiment the support is flat glass or single-crystal silicon.

Target molecule. As used herein, "target molecule" refers to a nucleic acid molecule to which a particular primer or probe is capable of preferentially hybridizing.

Target sequence. As used herein, "target sequence" refers to a nucleic acid sequence within the target molecules to which a particular primer or probe is capable of preferentially hybridizing.

Template. The term "template" as used herein refers to a double-stranded or single-stranded molecule which is to be amplified, synthesized or sequenced. In the case of a double-stranded DNA molecule, denaturation of its strands to form a first and a second strand is preferably performed to amplify, sequence or synthesize these molecules. A primer, complementary to a portion of a template is hybridized under appropriate conditions and the polymerase (DNA polymerase or reverse transcriptase) may then synthesize a nucleic acid molecule complementary to said template or a portion thereof. The newly synthesized molecule, according to the invention, may be equal or shorter in length than the original template. Mismatch incorporation during the synthesis or extension of the newly synthesized molecule may result in one or a number of mismatched base pairs. Thus, the synthesized molecule need not be exactly complementary to the template. The template can be an RNA molecule, a DNA molecule or an RNA/DNA hybrid molecule. A newly synthesized molecule may serve as a template for subsequent nucleic acid synthesis or amplification.

Thermostable. As used herein "thermostable" refers to a polymerase (RNA, DNA or RT) which is resistant to inactivation by heat. DNA polymerases synthesize the formation of a DNA molecule complementary to a single-stranded DNA template by extending a primer in the 5'-to-3' direction. This activity for mesophilic DNA polymerases may be inactivated by heat treatment. For example, T5 DNA polymerase activity is totally inactivated by exposing the enzyme to a temperature of 90° C. for 30 seconds. As used herein, a thermostable DNA polymerase activity is more resistant to heat inactivation than a mesophilic DNA polymerase. However, a thermostable DNA polymerase does not mean to refer to an enzyme which is totally resistant to heat inactivation and thus heat treatment may reduce the DNA polymerase activity to some extent. A thermostable DNA polymerase typically will also have a higher optimum temperature than mesophilic DNA polymerases.

Other terms used in the fields of recombinant DNA technology and molecular and cell biology as used herein will be generally understood by one of ordinary skill in the applicable arts.

The present invention provides oligonucleotides, which may be labeled internally, and/or, at or near the 3' termini and/or 5' termini or may be unlabeled. In another aspect, the oligonucleotides of the present invention may be provided with a specificity enhancing group. Such a group may be located internally and/or at or near the 3'- and/or the 5'-terminal of the oligonucleotide. In another aspect, the oligonucleotides of the present invention may be in the form of a hairpin. In some preferred embodiments, the oligonucleotides may be provided with more than one of these characteristics, i.e., they may comprise a label and/or a specificity enhancing group and/or may be in the form of a hairpin.

When labeled, oligonucleotides of the invention may contain one or multiple labels (which may be the same or different). The oligonucleotides of the invention may be used as primers and/or probes. In a preferred aspect, the oligonucleotides are labeled and the label is any moiety which undergoes a detectable change in any observable property upon hybridization and/or extension. In a preferred embodiments, the label is a fluorescent moiety and the label undergoes a detectable change in one or more fluorescent properties. Such properties are seen to include, but are not limited to, fluorescent intensity, fluorescent polarization, fluorescent lifetime and quantum yield of fluorescence. The oligonucleotides for use in the invention can be any suitable size, and are preferably in the range of 10-100 or 10-80 nucleotides, more preferably 11-40 nucleotides and most preferably in the range of 17-25 nucleotides although oligonucleotides may be longer or shorter depending upon the need.

The oligonucleotides of the invention can be DNA or RNA or chimeric mixtures or derivatives or modified versions thereof. In addition to being labeled with a detectable moiety, the oligonucleotide can be modified at the base moiety, sugar moiety, or phosphate backbone, and may include other appending groups or labels.

For example, the oligonucleotides of the invention may comprise at least one modified or more base moieties which are selected from the group including but not limited to 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylamino-methyl-2-thiouridine, 5-carboxymethylaminomethyluracil, dihydrouracil, beta-D-galactosylqueosine, inosine, $N^6$-isopentenyladenine, 1-methylguanine, 1-methyl-linosine, 2,2-dimethylguanine, 2-methyladenine, 2-methylguanine, 3-methylcytosine, 5-methylcytosine, $N^6$-adenine, 7-methylguanine, 5-methylaminomethyluracil, 5-methoxyaminomethyl-2-thiouracil, beta-D-mannosylqueosine, 5'-methoxycarboxy-methyluracil, 5-methoxyuracil, 2-methylthio-$N^6$-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine.

In another embodiment, the oligonucleotides of the invention comprises at least one modified sugar moiety selected from the group including but not limited to arabinose, 2-fluoroarabinose, xylulose, and hexose.

In yet another embodiment, the oligonucleotides of the invention comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

The oligonucleotides of the invention have use in nucleic acid amplification or synthesis reactions (e.g., as primers) to detect or measure a nucleic acid product of the amplification or synthesis reaction, thereby detecting or measuring a target nucleic acid in a sample that is complementary to all or a portion of a primer sequence. The oligonucleotides of the invention may be used in any amplification reactions including PCR, 5-RACE, Anchor PCR, "one-sided PCR," LCR, NASBA, SDA, RT-PCR and other amplification systems known in the art.

Thus, the invention generally relates to methods of synthesizing or amplifying one or more nucleic acid molecules comprising:
  (a) mixing one or more templates or target nucleic acid molecules with one or more oligonucleotides of the invention; and
  (b) incubating said mixture under conditions sufficient to synthesize or amplify one or more nucleic acid molecules complementary to all or a portion of said templates or target molecules.

Preferably, the synthesized or amplified nucleic acid molecules comprise one or more oligonucleotides of the invention or portions thereof. In one aspect, the oligonucleotides of the invention are incorporated at or near one or both termini of the synthesized or amplified nucleic acid molecules produced by the methods of the invention. The invention also relates to one or more nucleic acid molecules produced by such amplification or synthesis reactions.

In another aspect, the invention relates to methods of synthesizing one or more nucleic acid molecules, comprising
  (a) mixing one or more nucleic acid templates (which may be DNA molecules such as a cDNA molecules, or RNA molecules such as mRNA molecules, or populations of such molecules) with one or more primers of the invention and one or more polymerases; and
  (b) incubating the mixture under conditions sufficient to synthesize one or more first nucleic acid molecules complementary to all or a portion of the templates.

Such incubation conditions may involve the use of one or more nucleotides and one or more nucleic acid synthesis buffers. Such methods of the invention may optionally comprise one or more additional steps, such as incubating the synthesized first nucleic acid molecules under conditions sufficient to make one or more second nucleic acid molecules complementary to all or a portion of the first nucleic acid molecules. Such additional steps may also be accomplished in the presence of one or more primers of the invention and one or more polymerases as described herein. The invention also relates to nucleic acid molecules synthesized by these methods.

The invention also relates to methods for sequencing nucleic acid molecules comprising
  (a) mixing a nucleic acid molecule to be sequenced with one or more primers of the invention, one or more nucleotides and one or more terminating agents to form a mixture;
  (b) incubating the mixture under conditions sufficient to synthesize the population of molecules complementary to all or a portion of the molecule to be sequence; and
  (c) separating the population to determining the nucleotide sequence of all or a portion of the molecule to be sequenced.

The invention more specifically relates to a method of sequencing a nucleic acid molecule, comprising:
  (a) mixing one or more of the oligonucleotides of the invention, one or more nucleotides, and one or more terminating agents;
  (b) hybridizing said oligonucleotides to a first nucleic acid molecule;
  (c) incubating the mixture of step (b) under conditions sufficient to synthesize a random population of nucleic acid molecules complementary to said first nucleic acid molecule, wherein said synthesized molecule are shorter in length than said first molecule and wherein said synthesized molecules comprise a terminator nucleotide at their 3' termini; and
  separating said synthesized molecules by size so that at least a part of the nucleotide sequence of said first nucleic acid molecule can be determined. Such terminator nucleotides include ddTTP, ddATP, ddGTP, ddITP or ddCTP. Such incubation conditions may include incubation in the presence of one or more polymerases and/or buffering salts.

In a related aspect, the oligonucleotides of the invention are useful in detecting the presence or absence of or quantifying the amount of nucleic acid molecules in a sample without the need for performing amplification or synthesis reactions. In accordance with the invention, an oligonucleotide may be provided with one or more labels which undergo a detectable change in at least one observable property when the oligonucleotide comprising the label is converted to a double stranded molecule (e.g., by hybridizing the oligonucleotide to a target molecule). Thus, a change in an observable property indicates the presence of the target molecule in the sample when compared to a control sample not containing the nucleic acid molecule of interest. Quantification of the nucleic acid target molecule in the sample may also be determined by comparing change in the observable property in an unknown sample to the changes in the observable property in samples containing known amounts of the nucleic acid target molecule of interest. Any samples thought to contain the nucleic acid molecule of interest may be used including, but not limited to, biological samples such as blood, urine, tissue, cells, feces, serum, plasma, or any other samples derived from animals (including humans), plants, bacteria, viruses and the like. Environmental samples such as soil samples, water samples, air samples and the like may also be used in accordance with the invention.

The oligonucleotides of the invention can be used in methods of diagnosis, wherein the oligonucleotide is complementary to a sequence (e.g., genomic or cDNA) of an infectious disease agent or is capable of initiating synthesis or amplification of a sequence of an infectious disease agent, e.g. of human disease including but not limited to viruses (e.g, HIV, HPV etc), bacteria, parasites, and fungi, thereby diagnosing the presence of the infectious agent in a sample from a patient. The type of target nucleic acid can be genomic, cDNA, mRNA, synthetic, or the source may be human, animal, or bacterial. In another embodiment that can be used in the diagnosis or prognosis of a disease or disorder, the target sequence is a wild type human genomic or RNA or cDNA sequence, mutation of which is implicated in the presence of a human disease or disorder, or alternatively, can be the mutated sequence. In such an embodiment, the hybridization, amplification or synthesis reaction of the invention can be repeated for the same sample with different sets of oligonucleotides of the invention (for example, with differently labeled oligonucleotide) which selectively identify the wild type sequence or the mutated version. By way of example, the mutation can be an insertion, substitution, and/or deletion of one or more nucleotides, or a translocation.

In a specific embodiment, the invention provides a method for detecting or measuring a product of a nucleic acid amplification or synthesis reaction comprising (a) contacting a sample comprising one or more target nucleic acid molecules with one or more primers (such primers may comprise one or multiple labels, which may be the same or different and may be labeled internally, and/or, at or near the 3' and/or 5' end), said primers being adapted for use in said amplification or synthesis reaction such that said primers are incorporated into an amplified or synthesized product of said amplification or synthesis reaction when a target sequence or nucleic acid molecule is present in the sample; (b) conducting the amplification or synthesis reaction; and (c) detecting or measuring one or more synthesis or amplification product molecules (preferably by detecting a change in one or more observable properties of one or more labels).

In another specific embodiment, the invention provides for a method of detecting or measuring the presence or absence or the amount of a target nucleic acid molecule within a sample comprising (a) contacting a sample comprising one or more target nucleic acid molecules with one or more oligonucleotides of the invention (such oligonucleotides may comprise one or multiple labels, which may be the same or different and may be labeled internally and/or at or near the 3' and/or 5' end); (b) incubating said mixture under conditions sufficient to allow said oligonucleotides to interact with said target molecules sufficient to form double stranded molecules (preferably through hybridization); and (c) detecting one or more of said target nucleic acid molecules (preferably by detecting a change in one or more observable properties of one or more labels).

The present invention provides a method for detecting a target nucleic acid sequence, comprising the steps of contacting a sample containing a mixture of nucleic acids with at least one oligonucleotide of the present invention, the oligonucleotide capable of hybridizing a target nucleic acid sequence and comprises at least one detectable moiety, wherein the detectable moiety undergoes a change in one or more observable properties upon hybridization to the target nucleic acid sequence and observing the observable property, wherein a change in the observable property indicates the presence of the target nucleic acid sequence. In some embodiments, the target nucleic acid sequence is not separated from the mixture. In some embodiments, the observable property is fluorescence. In some embodiments, the change is an increase in fluorescence. In some embodiments, the change is a decrease in fluorescence. In some embodiments, the oligonucleotide comprises a specificity enhancing group. In some embodiments, the oligonucleotide is in the form of a hairpin.

The present invention provides a method for quantifying a target nucleic acid molecule, comprising the steps contacting a sample containing a mixture of nucleic acids comprising the target nucleic acid molecule with at least one oligonucleotide of the present invention, the oligonucleotide capable of hybridizing to the target nucleic acid molecule and comprises at least one detectable moiety, wherein the detectable moiety undergoes a change in one or more observable properties upon hybridization to the target nucleic acid sequence and observing the observable property, wherein a change in the observable property is proportional to the amount of the target nucleic acid molecule in the sample.

In a further aspect, the invention relates to the use of one or more treatments to lower or decrease the energy emitted by the labels of the oligonucleotides of the invention. Such treatments may be used in accordance with the invention to lower the background in the hybridization, synthesis or amplification methods of the invention. In one aspect, single stranded nucleic acid binding protein (*E. coli*, T4 bacteriophage or Archaea (see Kelly, et al. *Proceedings of the National Academy of Sciences*, USA 95:14634-14639 (1998), Chedin, et al., *TIBS* 23:273-277 (1998), U.S. Pat. Nos. 5,449,603, 5,605,824, 5,646,019, and 5,773,257) may be used to interact with single stranded labeled oligonucleotides of the invention to reduce or quench energy emitted or other detectable properties from the labels. Such single stranded binding proteins may be native or modified. During the detection or quantitation process (hybridization, synthesis or amplification reactions) double stranded nucleic acid molecules formed do not substantially interact with single stranded binding protein or interact minimally with such double stranded molecules. Accordingly, in the unreacted state (single stranded form of the oligonucleotides of the invention), energy emitted or other detectable properties (e.g., fluorescence) is reduced or quenched while in the reactive form (double stranded molecules) energy emitted or other detectable properties is enhanced. In another aspect, blocking oligonucleotides which contain quencher molecules may be used to competitively bind the labeled oligonucleotides in the invention in the unreacted stated thereby reducing energy emitted or other detectable properties of the labeled oligonucleotide. In another aspect, one or more additional fluorescent moieties may be incorporated into the blocking molecule such that the fluorescent moiety on the oligonucleotide of the invention is in proximity to the one or more additional fluorescent moieties when the oligonucleotide of the invention is in the unreacted state. The presence of an additional fluorescent molecule can reduce the background fluorescence level even though there is little or no overlap between the emission spectrum of the fluorescent moiety on the oligonucleotide of the invention and the absorption spectrum of the one or more additional fluorescent moieties on the blocking oligonucleotide. When the oligonucleotide of the invention has the capability of forming a hairpin structure, those skilled in the art will appreciate the one or more additional fluorescent moieties can be brought into proximity with the label on the oligonucleotide of the invention by attaching the one or more additional fluorescent moieties to nucleotides in one strand of the stem structure of the hairpin while attaching one or more labels to nucleotides in the other strand. During detection or quantitation, target nucleic acid molecules interact with labeled oligonucleotides of the invention thereby enhancing energy emitted or other detectable properties by the labels. Such interaction may separate the blocking oligonucleotide (e.g., quencher/additional fluorescent moiety-containing molecule) from the label containing oligonucleotide of the invention.

In another aspect of the present invention, the sequence of the oligonucleotide and/or a blocking oligonucleotide may be selected so as to reduce the background fluorescence of the oligonucleotides of the invention. It has been unexpectedly found that the base sequence in the vicinity of the label can have a dramatic effect on the background fluorescence level. The background fluorescence of a single stranded oligonucleotide of the present invention can be decreased about 5 fold if the sequence of the oligonucleotide is selected so as to form a blunt-end double stranded structure with one or more fluorophores located on one or more base close to the 3'-end and G-C or C-G base pair being the last base pair of the double stranded structure. In some preferred embodiments, the double stranded structure may be a stem of a hairpin structure. In some preferred embodiments, the 3'-end of the oligonucleotides of the invention may be provide with one of the following sequences: 5'- . . . T(Fluo)C-3',5'- . . . T(Fluo)G-3',5'- . . . (Fluo)AG-3',5'- . . . T(Fluo)AC-3',5'- . . . T(Fluo)TC-3',5'- . . . T(Fluo)TG-3' where the attachment of a fluorophore is indicated by (Fluo) and the 3'-sequence is as shown while the blocking oligonucleotide (or 5'-end of a hairpin oligonucleotide) is provided with the complementary sequence (preferably at the 5'end of the blocking oligonucleotide/hairpin molecule). To achieve a quenching effect the labeled base should be within 10 nucleotides distance from the 3'-end, preferably within 6 nucleotides and most preferably within 1-4 nucleotides. A specific example of oligonucleotides of this type is provided by Oligo 10 (SEQ ID NO:22) in Table 2. In a related embodiment, when using an oligonucleotide that does not have G or C for its 3'-most nucleotide and hence cannot form a G-C base pair at the 3'-end, the addition of a 5'-overhanging G residue to the oligonucleotide can reduce the background fluorescence. Also, the presented mode of quenching can be combined with the another mechanism of quenching like fluorescence resonance energy transfer or static quenching. In some embodiments of the present invention, combinations of quenching techniques may be employed to reduce the background fluorescence. For example, an oligonucleotide of the present invention may have a detectable moiety located near the 3'end of the oligonucleotide while the sequence of the oligonucleotide may be selected so as to have a G-C base pair at a blunt end of a hairpin structure and one or more additional fluorescent moieties may be attached to nucleotides at or near the 5'-end of the oligonucleotide. A similar structure could be employed utilizing a blocking oligonucleotide instead of a hairpin.

Other means for quenching or reducing nonreacted labeled oligonucleotides may be used or any combination of such treatments may be used in accordance with the invention.

The present invention provides a composition comprising one or more oligonucleotides of the invention and one or more target or template nucleic acid molecules, wherein at least a portion of the oligonucleotide is capable of hybridizing to at least a portion of the target or template nucleic acid molecule (preferably the oligonucleotide comprises one or more detectable moieties that undergo a change in one or more observable property upon hybridization to the target nucleic acid molecule). In some embodiments, the detectable moiety is a fluorescent moiety and the fluorescent moiety undergoes a change in fluorescence upon hybridizing to the target nucleic acid molecule. In some embodiments, the oligonucleotide is a hairpin when not hybridized to the target nucleic acid molecule.

In some preferred embodiments, the present invention provides a composition comprising at least one nucleic acid molecule and at least one oligonucleotide of the invention, wherein at least a portion of said oligonucleotide is capable of hybridizing with at least a portion of said nucleic acid molecule and wherein said oligonucleotide comprises one or more specificity enhancing groups. In some embodiments, one or more of the specificity enhancing groups may be a fluorescent moiety. A specificity enhancing group may be attached at any position of the oligonucleotide that results in the oligonucleotide being substantially less extendable when the 3'-most nucleotide of the oligonucleotide is not complementary to the corresponding nucleotide of a target/template nucleic acid. In some embodiments, at least one of the one or more groups is attached to a nucleotide at or near the 3'-nucleotide. In some embodiments, at least one of the one or more groups is attached to one of the ten 3'-most nucleotides. In other words, in embodiments of this type, at least one of the one or more specificity enhancing groups may be attached to the 3'-most nucleotide or any of the next nine contiguous nucleotides in the 5'-direction. In some embodiments, at least one of the one or more groups is attached to one of the five 3'-most nucleotides. In some embodiments, the group may be a label, preferably a label which undergoes a detectable change in an observable property upon becoming part of a double stranded molecule, (e.g. by hybridizing to another nucleic acid molecule or by nucleic acid synthesis or amplification). In some embodiments, at least a portion of said oligonucleotide is hybridized to at least a portion of said nucleic acid molecule. In some embodiments, the oligonucleotide is capable of forming a hairpin. In some embodiments, the oligonucleotide is in the form of a hairpin.

The present invention provides a method of making a composition, comprising the steps of providing one or more oligonucleotides and contacting the one or more oligonucleotides with at least one nucleic acid molecule, wherein at least a portion of at least one of said oligonucleotides is capable of hybridizing with at least a portion of said nucleic acid molecule. Preferably, the oligonucleotide comprises one or more specificity enhancing groups and/or at least one detectable label. In some embodiments, the group is a fluorescent moiety. A specificity enhancing group may be attached at any position of the oligonucleotide that results in the oligonucleotide being substantially less extendable when the 3'-most nucleotide of the oligonucleotide is not complementary to the corresponding nucleotide of a target/template nucleic acid. In some embodiments, at least one of the one or more groups is attached to a nucleotide at or near the 3'-nucleotide. In some embodiments, at least one of the one or more groups is attached to one of the ten 3'-most nucleotides. In other words, in embodiments of this type, at least one of the one or more specificity enhancing groups may be attached to the 3'-most nucleotide or any of the next nine contiguous nucleotides in the 5'-direction. In some embodiments, at least one of the one or more groups is attached to one of the five 3'-most nucleotides. In some embodiments, the group may be a label, preferably a label which undergoes a detectable change in an observable property upon becoming part of a double stranded molecule, (e.g. by hybridizing to another nucleic acid molecule). In some embodiments, at least a portion of said oligonucleotide is hybridized to at least a portion of said nucleic acid molecule. In some embodiments, the oligonucleotide is capable of forming a hairpin. In some embodiments, the oligonucleotide is in the form of a hairpin.

The present invention provides a method of determining the presence of a particular nucleotide or nucleotides at a specific position or positions in a target or template nucleic acid molecule, comprising the steps of (a) contacting at least one target or template nucleic acid molecule having a nucleotide or nucleotides at a specific position or positions with one or more oligonucleotides of the invention, wherein at least a portion of the oligonucleotide is capable of forming base pairs (e.g., hybridizing) with at least a portion of the target or template nucleic acid molecule said oligonucleotide preferably comprises at least one specificity enhancing group and/or label; and (b) incubating the oligonucleotide and the nucleic acid molecule mixture under conditions sufficient to cause extension of the oligonucleotide when the 3'-most nucleotide or nucleotides of the oligonucleotide base pair with the nucleotide or nucleotides at the specific position or positions of the nucleic acid target molecule. Under such conditions, the production of an extension product indicates the presence of the particular nucleotide or nucleotides at the specific position or positions. In another aspect, the invention provides a method for determining the absence of at least one particular nucleotide at a specific position or positions in a target or template nucleic acid molecule, comprising (a) contacting at least one target nucleic acid molecule having a nucleotide or nucleotides at a specific position with an oligonucleotide of the invention, wherein at least a portion of the oligonucleotide is capable of forming base pairs (e.g., hybridizing) with at least a portion of the target nucleic acid molecule (said oligonucleotide preferably comprising at least one specificity enhancing group or label); and (b) incubating the oligonucleotide and the nucleic acid molecule mixture under conditions sufficient to prevent or inhibit extension of the oligonucleotide when the 3'-most nucleotide or nucleotides of the oligonucleotide does not base pair (e.g., does not hybridize) with the nucleotide at the specific position or positions of the target nucleic acid molecule. Under such conditions, the lack of production or reduced production of an extension product indicates the absence of the particular nucleotide or nucleotides at the specific position. In a preferred aspect, the results of the extension of the oligonucleotide in the above first method is compared to the lack or reduced level of extension of the oligonucleotide in the above second method. In a preferred aspect, the conditions in the first method are conducted such that all or a portion of the target nucleic acid molecule is amplified, while the conditions in the second method are conducted such that the target nucleic acid molecule is not amplified or amplified at a reduced level or slower rate compared to the amplified target nucleic acid molecule produced by the first method. In some embodiments, the specificity enhancing group is a fluorescent moiety. A specificity enhancing group may be attached at any position of the oligonucleotide that results in the oligonucleotide being substantially less extendable when the 3'-most nucleotide of the oligonucleotide is not complementary to the corresponding nucleotide of a target/template nucleic acid. In some embodiments, at least one of the one or more groups is attached to a nucleotide at or near the 3'-nucleotide. In some embodiments, at least one of the one or more groups is attached to one of the ten 3'-most nucleotides. In other words, in embodiments of this type, at least one of the one or more specificity enhancing groups may be attached to the 3'-most nucleotide or any of the next nine contiguous nucleotides in the 5'-direction. In some embodiments, at least one of the one or more groups is attached to one of the five 3'-most nucleotides. In some embodiments, the group may be a label, preferably a label which undergoes a detectable change in an observable property upon becoming part of a double stranded molecule, (e.g. by hybridizing to another nucleic acid molecule). In some embodiments, at least a portion of said oligonucleotide is hybridized to at least a portion of said nucleic acid molecule. In some embodiments, the oligonucleotide is capable of forming a hairpin. In some embodiments, the oligonucleotide is in the form of a hairpin. The conditions of incubation preferably include one or more polymerase enzymes such as Tsp DNA polymerase (available from Life Technologies, Inc. Rockville Md.).

The present invention provides a method of synthesizing one or more nucleic acid molecules, comprising (a) contacting at least one target or template nucleic acid molecule with at least one oligonucleotide of the invention, wherein at least a portion of said oligonucleotide is capable of hybridizing with at least a portion of said target/template nucleic acid molecule (said oligonucleotide preferably comprises at least one specificity enhancing group and/or label); and (b) incubating the target nucleic acid and oligonucleotide mixture under conditions sufficient to cause the extension of the oligonucleotide when the 3'-most nucleotide or nucleotides of the oligonucleotide are base paired (e.g. hybridized) to said target nucleic acid molecule. In another aspect, the invention provides a method for reduced synthesis of one or more nucleic acid molecules, comprising (a) contacting at least one target or template nucleic acid molecule with at least one oligonucleotide of the invention, wherein at least a portion of said oligonucleotide is capable of hybridizing with at least a portion of said target/template nucleic acid molecule (said oligonucleotide preferably comprises at least one specificity enhancing group and/or label), and (b) incubating the target/template nucleic acid molecule and oligonucleotide mixture under conditions sufficient to prevent or inhibit extension of the oligonucleotide when the 3'-most nucleotide or nucleotides of the oligonucleotide does not base pair (e.g., does not hybridize) with the nucleotide at the specific position or positions of the target/template nucleic acid molecule. In a preferred aspect, the results of the synthesis of the above first method is compared to the lack or reduced level of synthesis in the above second method. In a preferred aspect, the conditions of the first method are conducted such that all or a portion of the target nucleic acid molecule is amplified, while the conditions in the second method are conducted such that a target nucleic acid molecule is not amplified or amplified at a reduced level and/or a slower rate compared to the amplified target nucleic acid molecule produced by the first method. In some embodiments, the specificity enhancing group is a fluorescent moiety. In some embodiments, the group is attached to a nucleotide at or near the 3'-nucleotide. In some embodiments, the group is attached to one of the ten 3'-most nucleotides. In other words, in embodiments of this type, the group may be attached to the 3'-most nucleotide or any of the next nine contiguous nucleotides in the 5'-direction. In some embodiments, the group may be a label, preferably a label which undergoes a detectable change in an observable property upon becoming part of a double stranded molecule, (e.g. by hybridizing to another nucleic acid molecule). In some embodiments, at least a portion of said oligonucleotide is hybridized to at least a portion of said nucleic acid molecule. In some embodiments, the oligonucleotide is capable of forming a hairpin. In some embodiments, the oligonucleotide is in the form of a hairpin. The incubation conditions preferably include one or more polymerase enzymes such as Tsp DNA polymerase available from Life Technologies, Rockville, Md.

The present invention provides a method of quenching fluorescence from a fluorescent moiety, comprising the step of attaching the fluorescent moiety to an oligonucleotide, wherein the oligonucleotide is capable of assuming a conformation in which the oligonucleotide quenches the fluorescence of the fluorescent moiety. In some embodiments, the conformation is a hairpin.

The present invention also relates to kits for the detection or measurement of nucleic acid molecules or for polymerase activity in a sample. Such kits may also be designed to detect/quantitate nucleic acid molecules of interest during or after nucleic acid synthesis or amplification reactions. Such kits may be diagnostic kits where the presence of the nucleic acid is correlated with the presence or absence of a disease or disorder. The invention also relates to kits for carrying out extension, synthesis and/or amplification reactions of the invention and to kits for making the compositions of the invention.

In specific embodiments, the kits comprise one or more oligonucleotides of the invention (including primers and/or probes). The kit can further comprise additional components for carrying out the detection/quantification assays or other methods of the invention. Such kits may comprise one or more additional components selected from the group consisting of one or more polymerases (e.g., DNA polymerases and reverse transcriptases), one or more nucleotides, one or more buffering salts (including nucleic acid synthesis or amplification buffers), one or more control nucleic acid target molecules (to act as positive controls to test assay or assist in quantification of the amount of nucleic acid molecules in unknown samples), one or more quenchers (single stranded binding proteins, blocking oligonucleotides etc.), instructions for carry one out the methods of the invention and the like. Control nucleic acid molecules are preferably provided in the kits of the invention at known concentrations to establish control samples of known amounts of target molecules to assist one in establishing the amount of nucleic acid molecule of interest in an unknown sample. Thus, the measurement of activity of the labeled oligonucleotide for a known sample may be compared to such measurement for an unknown sample to quantify the amount of the target nucleic acid molecule in the unknown sample. The kits of the invention preferably comprise a container (a box, a carton, or other packaging) having in close confinement therein one and preferably more containers (tubes, vials and the like) which comprise various reagents for carrying out the methods of the invention. The reagents may be in separate containers or may be combined in different combinations in a single container. Such kits of the invention may further comprise instructions or protocols for carrying out the methods of the invention and optionally may comprise an apparatus or other equipment for detecting the detectable labels associated with the oligonucleotides of the invention.

It will be readily apparent to one of ordinary skill in the relevant arts that other suitable modifications and adaptations to the methods and applications described herein are obvious and may be made without departing from the scope of the invention or any embodiment thereof. Having now described the present invention in detail, the same will be more clearly understood by reference to the following examples, which are included herewith for purposes of illustration only and are not intended to be limiting of the invention.

EXAMPLE 1

Preparation of Oligonucleotides

Oligonucleotides may be prepared using any known methodology. In some preferred embodiments, oligonucleotides may be synthesized on solid supports using commercially available technology. Oligodeoxynucleotides were synthesized using DNA synthesizer-8700 (Milligen/Biosearch). Fluorescent moieties may be incorporated into the oligonucleotides of the present invention using any conventional technology. For example, fluorescent labels may be incorporated into nucleoside phosphoramidites and directly incorporated into the oligodeoxynucleotides during automated chemical synthesis. In some preferred embodiments, the modified nucleotide may be a fluorescein-dT phosphoramidite (Glen Research Cat #10-1056) which may be inserted into designated position during chemical synthesis of oligonucleotide. 5'-fluorescein phosphoramidite (FAM) (Glen Research cat# 10-5901) and 3'-TAMRA-CPG 500 (Glen Research cat #20-5910) were used to add the indicated labels to the 5' and 3'-end respectively of the oligodeoxynucleotide during chemical synthesis. Alternatively, a nucleotide containing a reactive functional moiety may be incorporated into the oligonucleotide during synthesis. After the completion of the synthesis and removal of the oligonucleotide from the solid support, the reactive functional moiety may by used to couple a fluorescent moiety containing molecule to the oligonucleotide. In some preferred embodiments, the reactive functional moiety may be an amino-modified C6-dT (Glen Research Catalog #10-1039) which may be inserted into designated position during chemical synthesis of oligonucleotide and used for further modification. The further modification may include the incorporation of a fluorescently labeled molecule. In some preferred embodiments, the fluorescently labeled molecule may be a 6-carboxyfluorescein succinimidyl ester (6-FAM, SE, cat# C6164 Molecular Probes), Fluorescein-5-isothiocyanate (FITC) (Molecular probe cat# F-1907), 5-(6-)-carboxytetramethylrhodamine (TAMRA) succinimidyl ester (Molecular Probes), or BODIPY 530/550 succinimidyl ester (Molecular Probes).

All labeled oligonucleotides may be purified using reverse-phase HPLC, for example, on a C-18 column using a gradient of acetonitrile in 0.2 M triethyl ammonium acetate.

Oligonucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. *Nucl Acids Res.* 16:3209 (1988), methylphosphonate oligonucleotides can be prepared by use of controlled pore glass polymer supports (Sarin et al., *Proc. Natl. Acad. Sci. USA* 85:7448-7451 (1988)). Oligonucleotides may also be prepared by standard phosphoramidite chemistry; or by cleavage of a larger nucleic acid fragment using non-specific nucleic acid cleaving chemicals or enzymes or site-specific restriction endonucleases. Labeled oligonucleotides of the invention may also be obtained commercially from Life Technologies, Inc. or other oligonucleotide manufactures.

A preferable method for synthesizing oligonucleotides is by using an automated DNA synthesizer using methods known in the art. Once the desired oligonucleotide is synthesized, it is cleaved from the solid support on which it was synthesized and treated, by methods known in the art, to remove any protecting groups present. The oligonucleotide may then be purified by any method known in the art, including extraction and gel purification. The concentration and purity of the oligonucleotide may be determined by examining the oligonucleotide that has been separated on an acrylamide gel, or by measuring the optical density at 260 nm in a spectrophotometer.

Oligonucleotides of the invention may be labeled during chemical synthesis or the label may be attached after synthesis by methods known in the art. In a specific embodiment, the label moiety is a fluorophore. Suitable moieties that can be selected as fluorophores or quenchers are set forth in Table 1.

TABLE 1

4-acetamido-4'-isothiocyanatostilbene-2,2'disulfonic acid
acridine and derivatives:

acridine
acridine isothiocyanate
5-(2'-aminoethyl)aminonaphthalene-1-sulfonic acid (EDANS)
4-amino-N-3-vinylsulfonyl)phenylnaphthalimide-3,5 disulfonate (Lucifer Yellow VS)
N-(4-anilino-1-naphthyl)maleimide
anthranilamide
Brilliant Yellow
coumarin and derivatives:

7-amino-4-methylcoumarin (AMC, Coumarin 120)
7-amino-4-trifluoromethylcouluarin (Coumaran 151)
cyanosine
4',6-diaminidino-2-phenylindole (DAPI)
5',5''-dibromopyrogallol-sulfonephthalein (Bromopyrogallol Red)
7-diethylamino-3-(4'-isothiocyanatophenyl)-4-methylcoumarin
diethylenetriamine pentaacetate
4,4'-diisothiocyanatodihydro-stilbene-2,2'-disulfonic acid
4,4'-diisothiocyanatostilbene-2,2'-disulfonic acid
5-dimethylaminonaphthalene-1-sulfonyl chloride (DNS, dansyl chloride)
4-(4'-dimethylaminophenylazo)benzoic acid (DABCYL)
4-dimethylaminophenylazophenyl-4'-isothiocyanate (DABITC)
eosin and derivatives:

eosin
eosin isothiocyanate
erythrosin and derivatives:

erythrosin B
erythrosin isothiocyanate
ethidium
fluorescein and derivatives:

5-carboxyfluorescein (FAM)
5-(4,6-dichlorotriazin-2-yl)aminofluorescein (DTAF)
2'7'-dimethoxy-4'5'-dichloro-6-carboxyfluorescein (JOE)
fluorescein
fluorescein isothiocyanate
QFITC (XRITC)
fluorescamine
IR144

TABLE 1-continued

IR1446
Malachite Green isothiocyanate
4-methylumbelliferone
ortho cresolphthalein
nitrotyrosine
pararosaniline
Phenol Red
B-phycoerythrin
o-phthaldialdehyde
pyrene and derivatives:

pyrene
pyrene butyrate
succinimidyl 1-pyrene butyrate
Reactive Red 4 (Cibacron ™ Brilliant Red 3B-A)
rhodamine and derivatives:

6-carboxy-X-rhodamine (ROX)
6-carboxyrhodamine (R6G)
lissamine rhodamine B sulfonyl chloride
rhodamine (Rhod)
rhodamine B
rhodamine 123
rhodamine X isothiocyanate
sulforhodamine B
sulforhodamine 101
sulfonyl chloride derivative of sulforhodamine 101 (Texas Red)
N,N,N',N'-tetramethyl-6-carboxyrhodamine (TAMRA)
tetramethyl rhodamine
tetramethyl rhodamine isothiocyanate (TRITC)
riboflavin
rosolic acid
terbium chelate derivative One of ordinary skill in the art can easily determine, using art-known techniques of spectrophotometry, which of the above identified fluorophores or combinations thereof can be used in accordance with the invention. Oligonucleotides are preferably modified during synthesis, such that a modified T-base is introduced into a designated position by the use of Amino-Modifier C6 dT (Glen Research), and a primary amino group is incorporated on the modified T-base, as described by Ju et al. (*Proc. Natl. Acad. Sci*., USA 92:4347-4351 (1995)). These modifications may be used for subsequent incorporation of fluorescent dyes into designated positions of the labeled oligonucleotides.

In yet another embodiment, the labeled oligonucleotides may be further labeled with any other art-known detectable marker, including radioactive labels such as $^{32}P$, $^{35}S$, $^{3}H$, and the like, or with enzymatic markers that produce detectable signals when a particular chemical reaction is conducted, such as alkaline phosphatase or horseradish peroxidase. Such enzymatic markers are preferably heat stable, so as to survive the denaturing steps of the amplification or synthesis process.

Oligonucleotides may also be indirectly labeled by incorporating a nucleotide linked covalently to a hapten or to a molecule such as biotin, to which a labeled avidin molecule may be bound, or digoxygenin, to which a labeled anti-digoxygenin antibody may be bound. Oligonucleotides may be supplementally labeled during chemical synthesis or the supplemental label may be attached after synthesis by methods known in the art.

The sequences of the primers used in the following specific examples are provided in Table 2.

TABLE 2

| | |
|---|---|
| Oligo A internally labeled with fluorescein | 5'-cct tct cat ggt ggc tgT aga ac (SEQ ID NO:1) |
| Oligo B 5'-labeled with fluoresecin | 5'-Cct tct cat ggt ggc tgt aga ac (SEQ ID NO:2) |
| Oligo C complement to oligo A and B | 5'-gtt cta cag cca cca tga gaa gg (SEQ ID NO:3) |
| Oligo D. 3'-labeled with TAMRA | 5'-ggg gct gcg act gtg ctc cgg cA (SEQ ID NO:4) |
| Oligo E. complement to oligo D | 5'-tgc cgg agc aca gtc gca gcc cc (SEQ ID NO:5) |
| Oligo F. 5'-labeled with fluorescein | 5'-Aat aat agg atg agg cag ga (SEQ ID NO:6) |
| Oligo G. 5'-labeled with BODIPY 530/550 | 5'-Aat aat agg atg agg cag ga (SEQ ID NO:7) |
| Oligo H complement to Oligo F and Oligo G | 5'-tcc tgc ctc atc cta tta tt (SEQ ID NO:8) |
| Oligo I forward primer for IL4 | 5'-gag ttg acc gta aca gac atc tt (SEQ ID NO:9) |
| Oligo J. forward primer for b-actin internally Labeled with fluorescein | 5'-ggc att gcc gac agg aTg tag aag (SEQ ID NO:10) |
| Oligo K. reverse primer for b-actin | 5'-ggg ccg gac tcg tca tac (SEQ ID NO:11) |
| Oligo L. forward primer for b-actin labeled with Fluorescein through the tail- | 5'-ggt tgT aga gca ctc agc aca atg aag a (SEQ ID NO:12) |
| Oligo 1 IL 4 forward primer | 5'-gag ttg acc gta aca gac atc tt (SEQ ID NO:13) |
| Oligo 2 IL 4 reverse primer, 297WT | 5'-cct tct cat ggt ggc tgt aga ac (SEQ ID NO:14) |
| Oligo 3 IL 4 reverse primer, 297MUT | 5'-cct tct cat ggt ggc tgt aga at (SEQ ID NO:15) |
| Oligo 4 IL 4 reverse primer, 300WT | 5'-gtg tcc ttc tca tgg tgg ctg tag (SEQ ID NO:16) |
| Oligo 5 IL 4 reverse primer, 300MUT | 5'-gtg tcc ttc tca tgg tgg ctg tat (SEQ ID NO:17) |
| Oligo 6 IL 4 reverse primer, 297WT -Fluo | 5'-cct tct cat ggt ggc tgT aga ac (SEQ ID NO:18) |
| Oligo 7 IL 4 reverse primer, 297MUT-Fluo | 5'-cct tct cat ggt ggc tgT aga at (SEQ ID NO:19) |
| Oligo 8 IL 4 reverse primer, 300WT -Fluo | 5'-gtg tcc ttc tca tgg tgg ctg Tag (SEQ ID NO:20) |
| Oligo 9 IL 4 reverse primer, 300MUT-Fluo | 5'-gtg tcc ttc tca tgg tgg ctg Tat (SEQ ID NO:21) |
| Oligo 10 RDS reverse primer- Fluo | 5'-cta ccg ggt gtc tgt gtc tcg gTa g (SEQ ID NO:22) |
| Oligo 11 RDS forward primer, C-allele | 5'-cgt acc tgg cta tct gtg tc (SEQ ID NO:23) |
| Oligo 12 RDS forward primer, T-allele | 5'-cgt acc tgg cta tct gtg tt (SEQ ID NO:24) |
| Oligo 13 RDS forward primer, C-allele/hairpin | 5'-gac acc tgg cta tct gtg tc (SEQ ID NO:25) |

TABLE 2-continued

| | | |
|---|---|---|
| Oligo 14 RDS forward primer, T-allele/hairpin | 5'-aac aca cct ggc tat ctg tgt t<br>(SEQ ID NO:26) | |
| Oligo 15 IL 4 reverse primer/hairpin | 5'-cta cag tcc ttc tca tgg tgg ctg tag<br>(SEQ ID NO:27) | |
| Oligo 16 b-globin forward primer/linear-A | 5'-ctt cct gag agc cga act gta gtg a<br>(SEQ ID NO:28) | |
| Oligo 17 b-globin reverse primer/linear-A | 5'-aca tgt att tgc atg gaa aac aac tc<br>(SEQ ID NO:29) | |
| Oligo 18 b-globin forward primer/hairpin-A | 5'-tca cta ctt cct gag agc cga act gta gtg a<br>(SEQ ID NO:30) | |
| Oligo 19 b-globin reverse primer/hairpin-A | 5'-gag ttg tac atg tat ttg cat gga aaa caa ctc<br>(SEQ ID NO:31) | |
| Oligo 20 b-globin forward primer/linear-B | 5'-gct cag aat gat gtt tcc acc ttc<br>(SEQ ID NO:32) | |
| Oligo 21 b-globin reverse primer/linear-B | 5'-aaa tca tac tag ctc acc agc aat g<br>(SEQ ID NO:33) | |
| Oligo 22 b-globin forward primer/hairpin-B | 5'-gaa ggt gct cag aat gat gtt tcc acc ttc<br>(SEQ ID NO:34) | |
| Oligo 23 b-globin reverse primer/hairpin-B | 5'-cat tgc aaa tca tac tag ctc acc agc aat g<br>(SEQ ID NO:35) | |
| Oligo 24 NF 1355 forward primer/linear | 5'-tgg cag ttg aat gcc aag taa t<br>(SEQ ID NO:36) | |
| Oligo 25 NF 1355 reverse primer/linear | 5'-aca gcc act gtg ccc agg tc<br>(SEQ ID NO:37) | |
| Oligo 26 NF 1355 forward primer/hairpin | 5'-att act tgg cag ttg aat gcc aag taa t<br>(SEQ ID NO:38) | |
| Oligo 27 NF 1355 reverse primer/hairpin | 5'-gac ctg aca gcc act gtg ccc agg tc<br>(SEQ ID NO:39) | |
| Oligo 28 NF 1616 forward primer/linear | 5'-att tca tgg ggg aaa caa aga tg<br>(SEQ ID NO:40) | |
| Oligo 29 NF 1616 reverse primer/linear | 5'-ata cct gcg ctc acc aca gg<br>(SEQ ID NO:41) | |
| Oligo 30 NF 1616 forward primer/hairpin | 5'-cat ctt tat ttc atg ggg gaa aca aag atg<br>(SEQ ID NO:42) | |
| Oligo 31 NF 1616 reverse primer/hairpin | 5'-cct gtg ata cct gcg ctc ac<u>c aca gg</u><br>(SEQ ID NO:43) | |

The nucleotide to which the fluorescent moiety is attached is indicated by a Bold capital letter.

EXAMPLE 2

PCR Targets and Conditions

Those skilled in the art will appreciate that any nucleic acid that can be amplified by PCR may be used in the practice of the present invention. Examples of suitable nucleic acids include, but are not limited to, genomic DNAs, cDNAs and cloned PCR products. The practice of the present invention is not limited to use with DNA molecules. For example, mRNA molecules may be used as templates for an amplification reaction by first conducting a first strand synthesis reaction using techniques well known in the art. The present invention has been exemplified using cDNAs for IL4 and b-actin synthesized using total mRNA from the corresponding cells and SuperScript™ System for the First Strand cDNA Synthesis (Gibco BRL, cat #18089-011) according to the manufacturer's manual. IL4 and b-actin cDNAs were amplified and cloned into pTEPA plasmid according to Gibco BRL manual (cat #10156-016).

The selection of suitable PCR conditions is within the purview of ordinary skill in the art. Those skilled in the art will appreciate that it may be necessary to adjust the concentrations of the nucleic acid target, primers and temperatures of the various steps in order to optimize the PCR reaction for a given target and primer. Such optimization does not entail undue experimentation. In the specific examples provided herein, PCR was performed in 25 µl of PLATINUM® Taq Reaction Buffer with 0.5 un of PLATINUM® Taq, 0.2 mM dNTPs, 0.2 µM forward and reverse primers, and 1.75 mM $MgCl_2$ using $10^4$-$10^6$ copies of target. PLATINUM® Tsp was used under the same conditions. Thermal cycling was performed on 9600 or ABI PRIZM™ 7700 Sequence Detector (Perkin Elmer) with 4 min denaturation at 94° C., followed by 35-40 cycles: 15 sec at 94° C., 30 sec at 55° C. and 40 sec at 72° C. In two-step PCR cycling conditions were 15 sec at 94° C. and 30 sec at 65° C.

EXAMPLE 3

Detection of Nucleic Acids

Nucleic acids may be detected by any conventional technology. In some preferred embodiments, the nucleic acid to be detected may be a PCR product and may be detected either by agarose gel electrophoresis or by homogeneous fluorescence detection method as described in U.S. provisional patent application Ser. No. 60/139,890, filed Jun. 22, 1999. In this method fluorescent signal is generated upon the incorporation of the specifically labeled primer into the PCR product. The method does not require the presence of any specific quenching moiety or detection oligonucleotide. In some preferred embodiments, the detection oligonucleotides are capable of forming a hairpin structure and are labeled with fluorescein attached close to the 3'-end.

The fluorescent measurements were performed in the PCR reaction buffer using on ABI PRIZM™ 7700 Sequence Detector, fluorescent plate reader (TECAN) or Kodak EDAS Digital Camera. Excitation/emission wavelengths were 490 nm/520 nm for fluorescein and 555 nm/580 nm for TAMRA.

EXAMPLE 4

Fluorescence Signal of Oligonucleotide Internally Labeled with Fluorescein Increases Upon its Hybridization to the Complementary Oligonucleotide Two oligonucleotides of the same sequence were labeled with fluorescein either internally on T-base (oligo A (SEQ ID NO:1)), or at the 5'-end (oligo B (SEQ ID NO:2)) as described above. 10 pmoles of each oligonucleotide was hybridized to the complementary oligo C (SEQ ID NO:3) (50 pmoles) in 0.05 ml of the PCR buffer, heated at 70° C. for 2 min and cooled to 25° C. Melting curves between 25 and 95° C. were determined on ABI PRIZM™ 7700 Sequence Detector.

Figure 2:
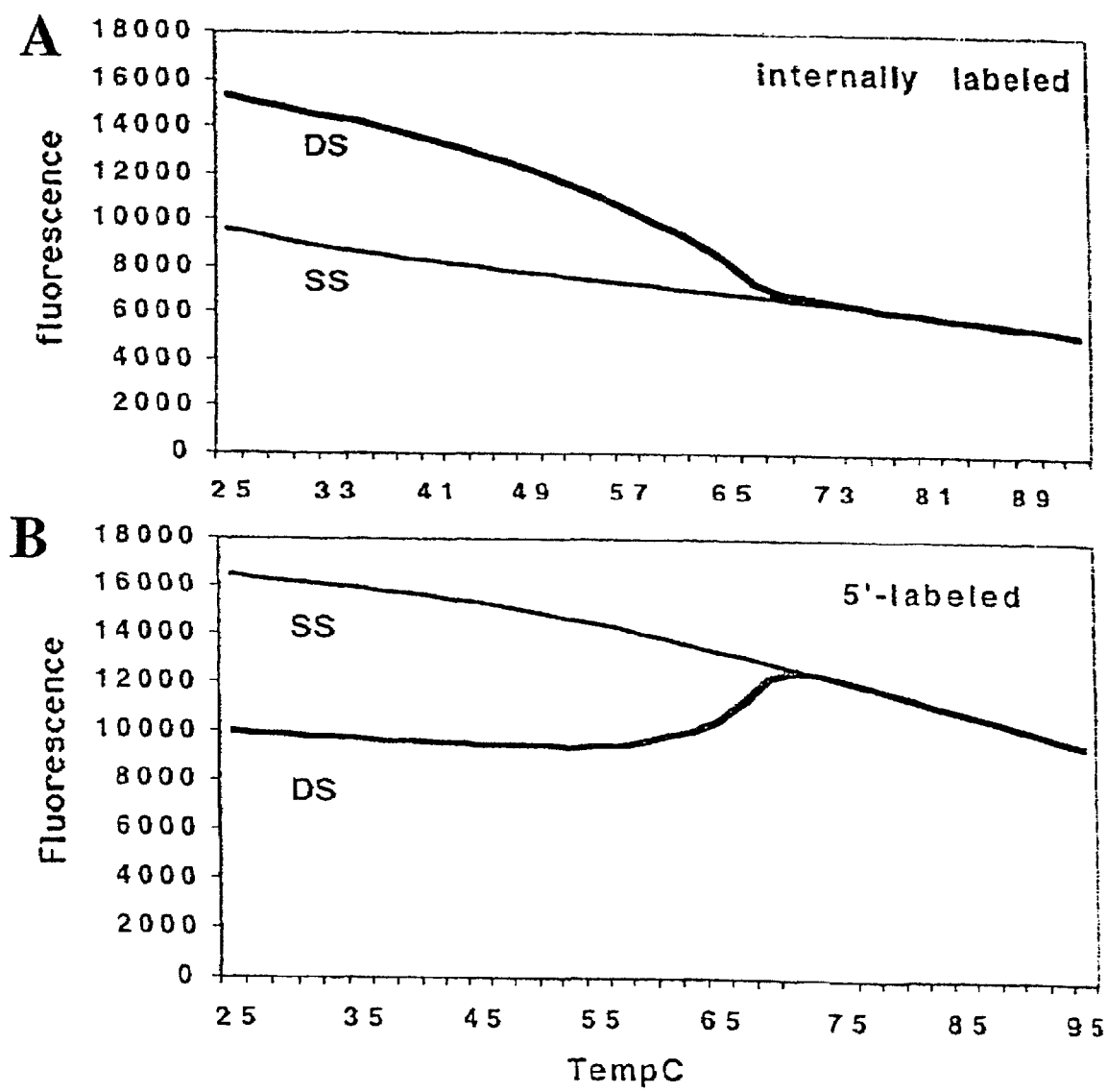
FIG. 2 is a graph of fluorescent intensity as a function of temperature which shows the effect of hybridization on the fluorescence of internally (Panel A) and 5'-fluorescein labeled (Panel B) oligonucleotides. Labeled oligonucleotides were tested for fluorescence under different temperatures. Single-stranded (SS) or double-stranded (DS) oligonucleotides were melted as described in Example 4. For 5'-labeled oligonucleotides, conversion from SS oligonucleotides to DS oligonucleotides caused a decrease in fluorescence, while for internally labeled oligonucleotides, conversion from SS oligonucleotides to DS caused an increase in fluorescence.

As shown in FIG. 2, in case of internally labeled Oligo A (SEQ ID NO:1), a fluorescence signal increases as a result of presence of the non-labeled complementary oligonucleotide. That means the signal increase was caused by the formation of the double-stranded structure. In contrast, when the fluorescein was present on the 5'-end of the same sequence (Oligo B (SEQ ID NO:2)), fluorescence signal decreased upon hybridization.

EXAMPLE 5

Oligodeoxynucleotide Labeled with TAMRA on its 3'-end, Increases the Fluorescence Signal Upon Hybridization 20 pmoles of Oligo D (SEQ ID NO:4) 3'-labeled with TAMRA as described above was annealed to 100 pmoles of complementary non-labeled oligodeoxynucleotide (Oligo E (SEQ ID NO:5)) in 0.5 ml of the PCR Buffer. Fluorescence emission spectrum was detected on spectrofluorimeter with 555 nm excitation.

Figure 3:
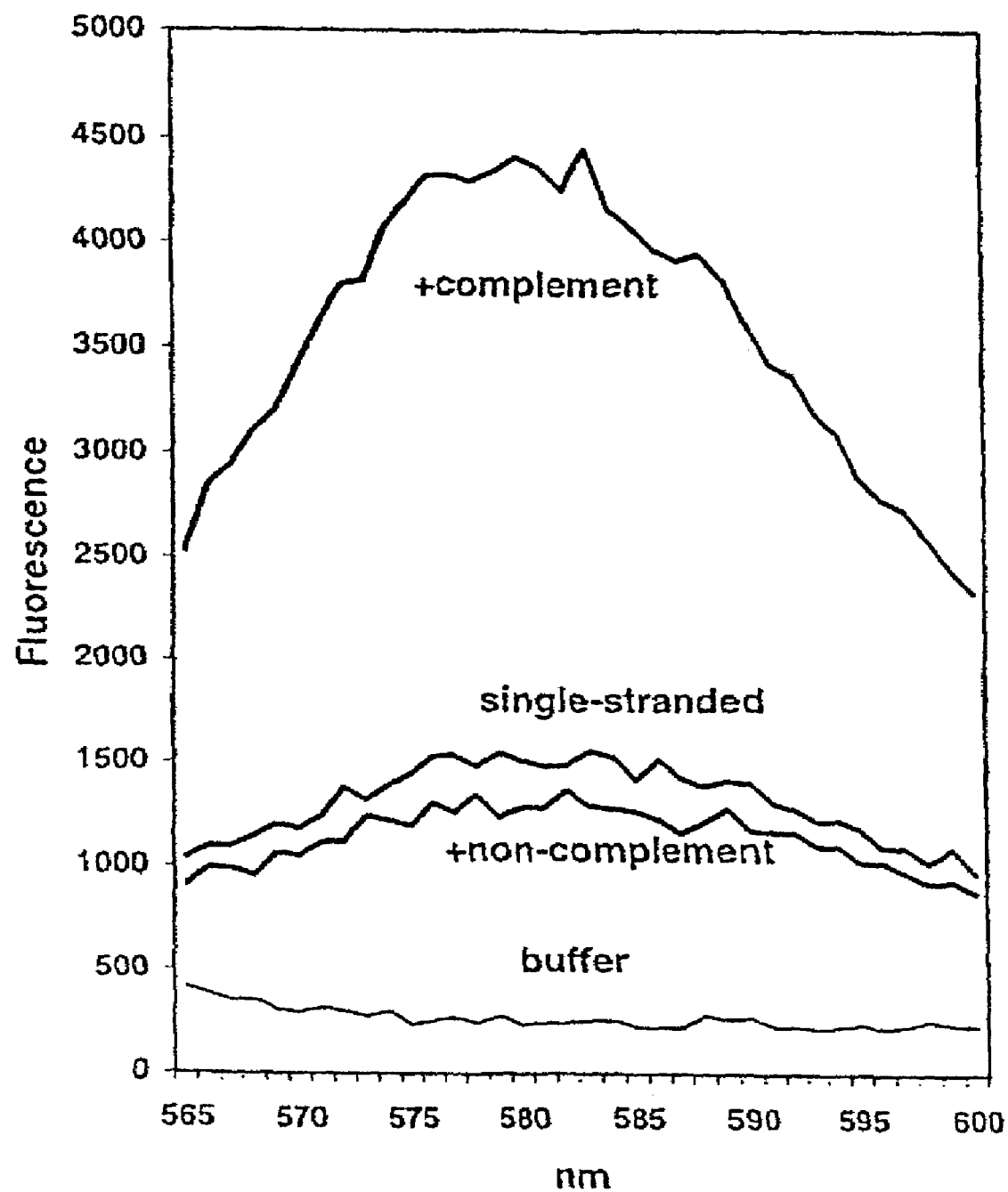
FIG. 3 is a graph of fluorescent intensity as a function of wavelength which shows fluorescence of 3'-TAMRA oligonucleotide in the presence of complementary and non-complementary oligonucleotides. In presence of complement (to create a double stranded molecule), the fluorescence increased compared to the single stranded form (see Example 5).

As shown in FIG. 3, a significant increase of the signal was observed upon hybridization, indicating that the proposed method can be applied to different fluorophores. The curve labeled buffer shows the fluorescence as a function of wavelength of the buffering solution. The curve labeled single-stranded shows the results obtained with the single-stranded version of oligo D (SEQ ID NO:4) alone. When a non-complementary oligonucleotide was added to oligo D (SEQ ID NO:4) a slight decrease in signal was observed (+non-complement). When complementary oligonucleotide oligo E (SEQ ID NO:5) was added, a large increase in fluorescence was observed (+complement).

EXAMPLE 6

Oligodeoxynucleotide 5'-Labeled with BODIPY 530/550 Increases the Fluorescence Signal Upon Hybridization In examples 4 and 5 oligonucleotides internally labeled with fluorescein and 3' labeled with TAMRA were shown to increase the fluorescence intensity upon hybridization to the complementary oligonucleotide. In contrast, oligonucleotides 5'-labeled with fluorescein demonstrated fluorescence quenching upon hybridization (see example 4 and [Cardullo et al., 1988, PNAS 85, 8790-8794; Wu et al. 1998, U.S. Pat. No. 5,846,729]).

However, there are some dyes that can show an enhancement of the fluorescence intensity upon hybridization even though they are located at the 5' position of an oligonucleotide. For example, an oligodeoxynucleotide labeled at the 5' end with BODIPY 530/550 shows an increase fluorescence intensity upon hybridization.

The same oligodeoxynucleotide sequence was 5'-labeled with fluorescein (Oligo F (SEQ ID NO:6)) or BODIPY 530/550 (Oligo G (SEQ ID NO:7)). 20 pmoles of each labeled oligonucleotide was annealed to 100 pmoles of complementary non-labeled oligodeoxynucleotide (Oligo H (SEQ ID NO:8)) in 0.5 ml of the PCR Buffer. Fluorescence emission spectrum was detected on spectrofluorimeter with 490 nm excitation in case of fluorescein and 538 nm excitation in case of BODIPY.

Figure 4:
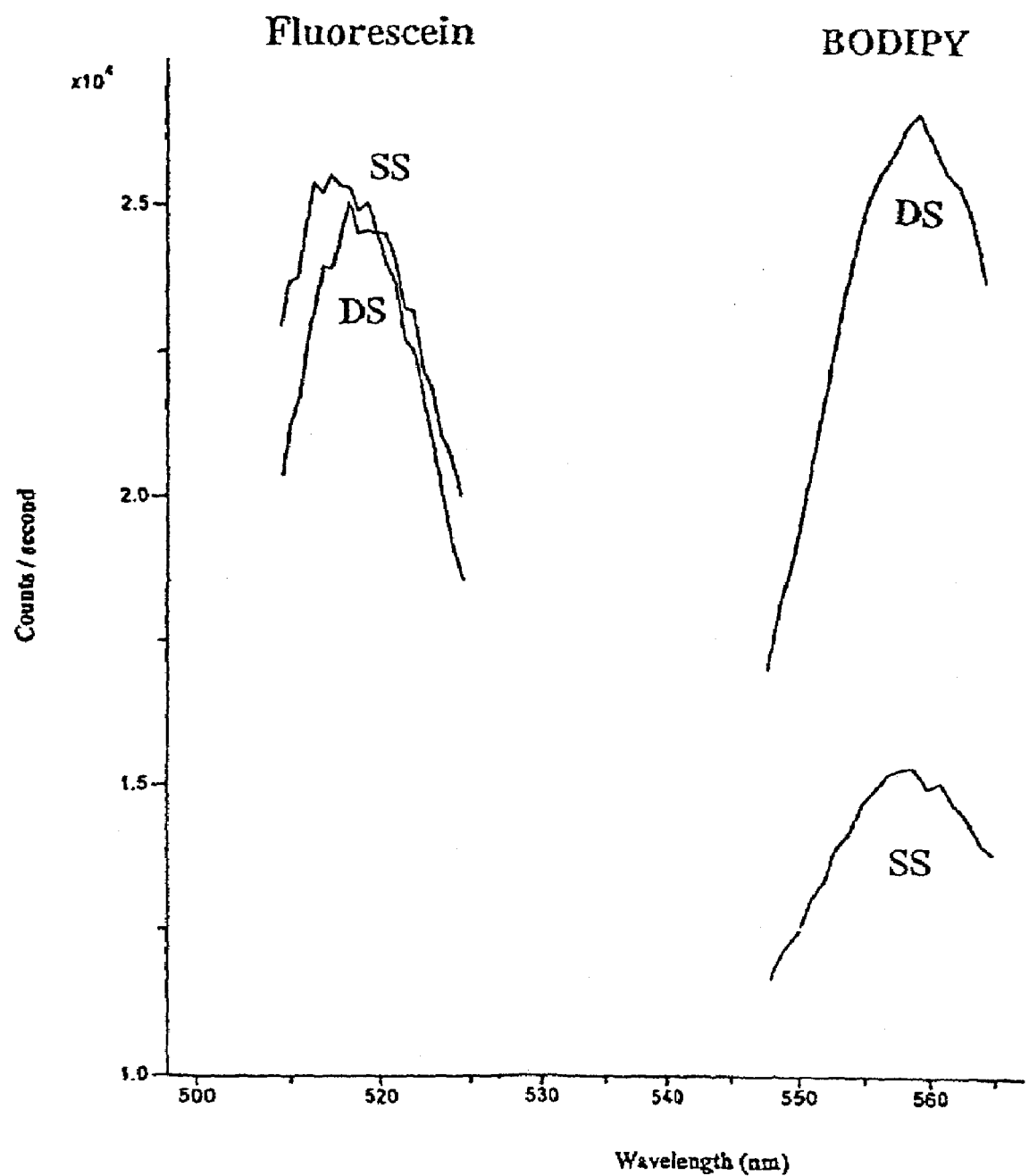
FIG. 4 is a graph of fluorescence as a function of wavelength which shows the effect of hybridization on the fluorescence of oligonucleotides 5'-labeled with fluorescein and BODIPY 530/550. In the presence of the complement oligonucleotide (to create a double stranded molecule), the fluorescence increased in case of BODIPY dye and decreased in case of fluorescein.

As shown in FIG. 4, a significant increase of the signal upon hybridization in case of BODIPY dye was observed, in contrast, a decrease in the signal was observed upon hybridization of a fluorescein containing oligonucleotide.

The results shown in Examples 4, 5 and 6 demonstrate that the fluorescent properties of a given fluorophore, in particular the fluorescent intensity, can be affected upon hybridization without significant shift of the emission spectrum as a result of the point of attachment of the fluorophore to a given oligonucleotide, i.e., internal, 3' and 5'.

EXAMPLE 7

Quantitative PCR of IL4 cDNA Using Primer Internally Labeled with Fluorescein

Figure 5A:
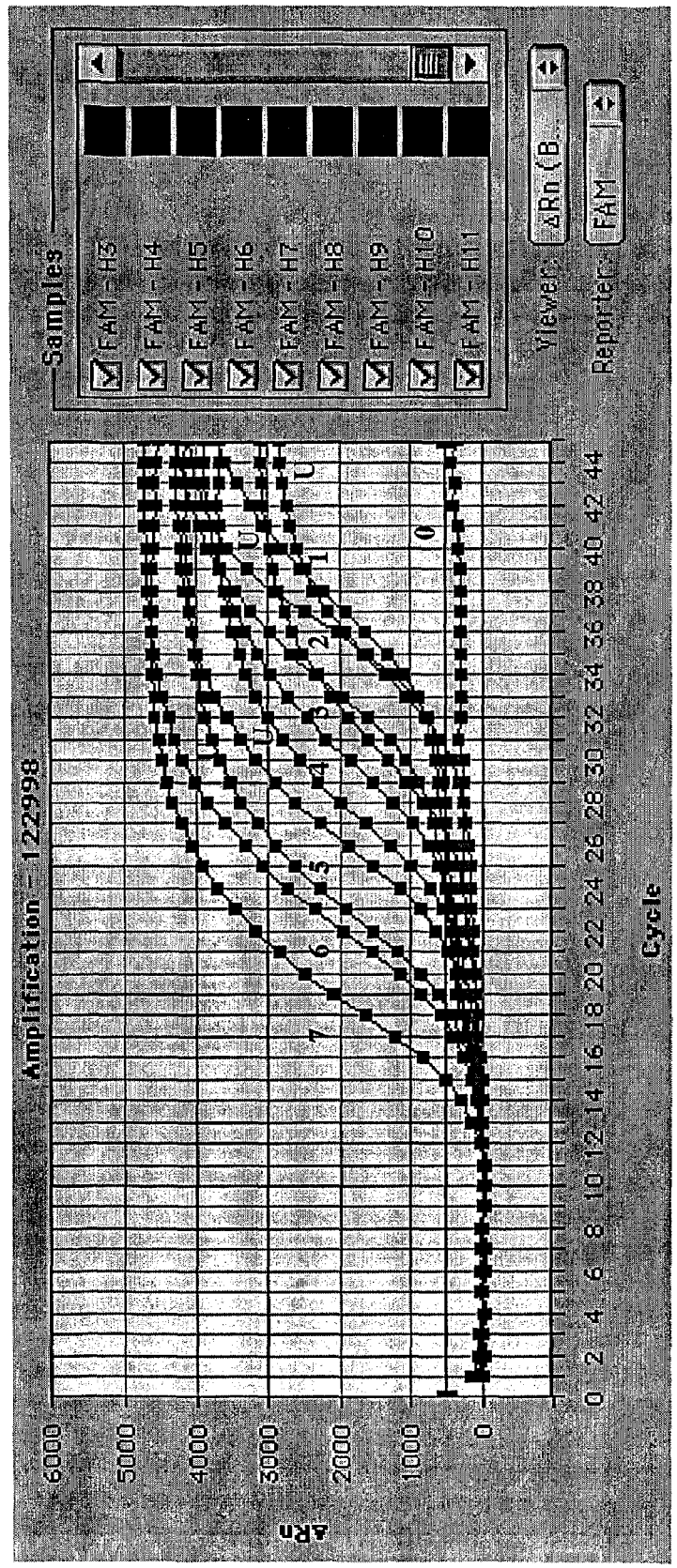
FIG. 5 is a graph of fluorescent intensity as a function of the number of cycles of amplification performed which shows quantitative PCR of IL4 cDNA with an internally labeled primer (Panel A). PCR was performed as described in Example 7. Data from ABI PRIZM™ 7700 Sequence Detector were treated according to the manufacture's instructions with minor modifications. Panel B is a standard curve plotting the number of cycles of amplification against the starting quantity of template DNA.
Figure 5B:
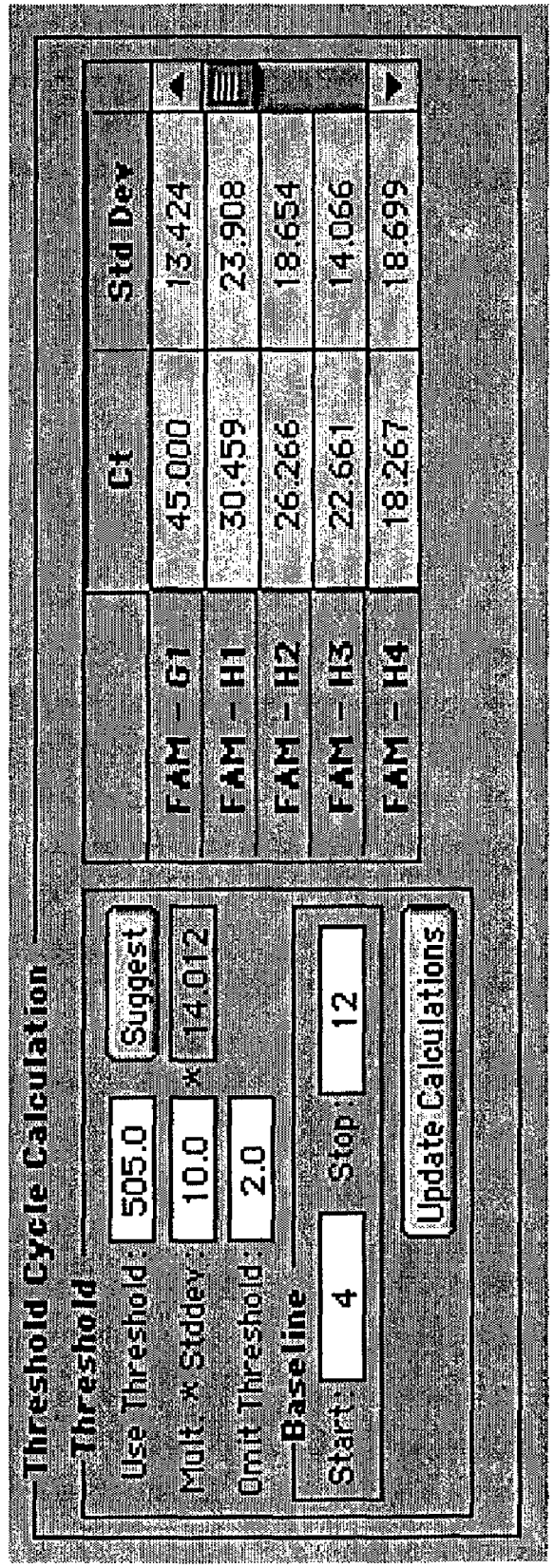
Figure 5C:
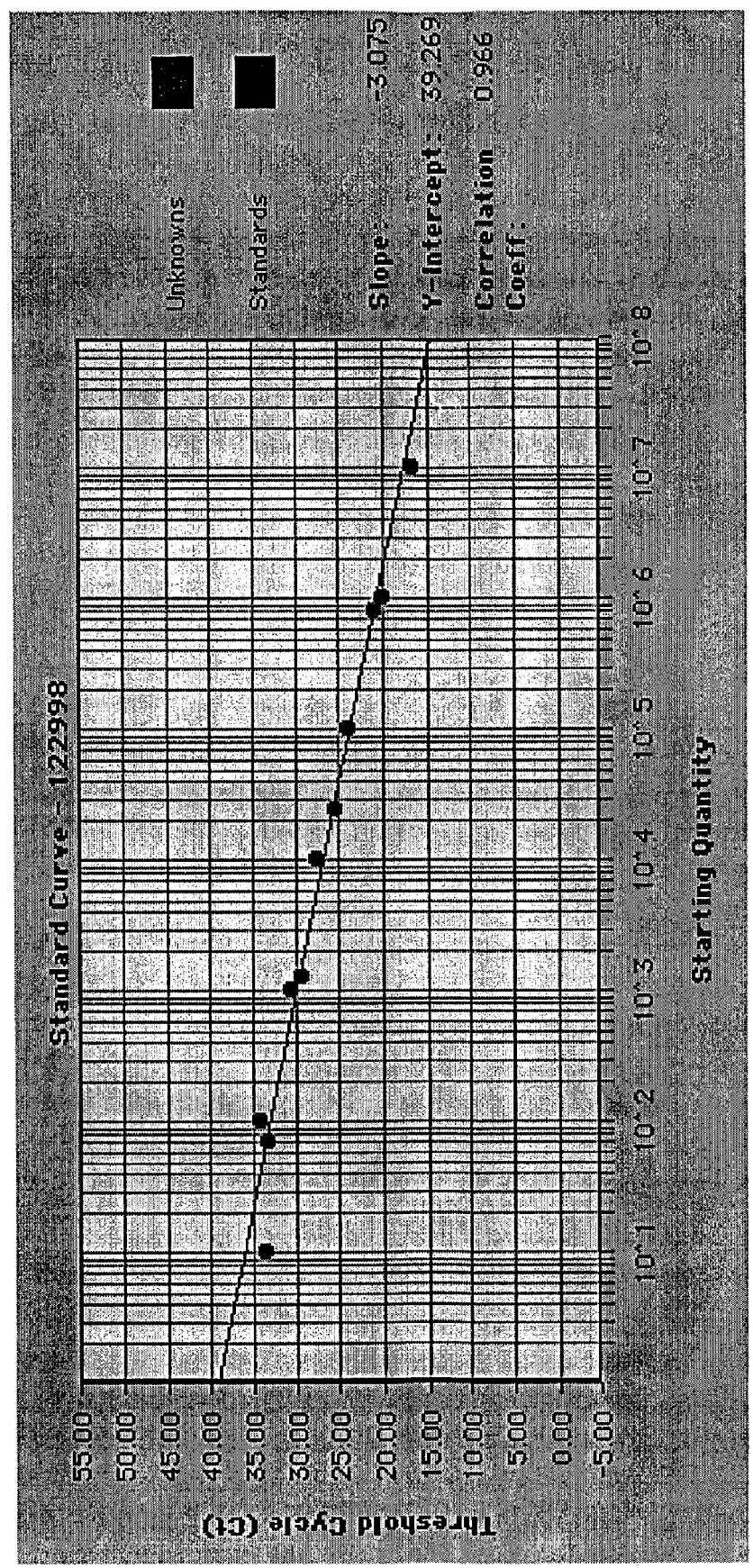

Fluorescein-dT was directly incorporated into the sequence of IL-4 primer during chemical synthesis using the methods described above. The resulting oligonucleotide (Oligo A (SEQ ID NO:1)) was used as a reverse primer for IL4 cDNA amplification. Quantitative PCR using reverse primer (Oligo A (SEQ ID NO:1)) and forward primer (Oligo I (SEQ ID NO:9)) was performed as described above in the presence of varying amounts of the template DNA. $10^7$, $10^6$, $10^5$, $10^4$, $10^3$, $10^2$, 10 and 0 copies of the cloned IL4 target were used per reaction along with four samples of unknown concentration of the target. As shown in FIG. 5, all dilutions of the DNA target can be detected with extremely high accuracy.

The results of this experiment demonstrate that although no quencher is present in the structure of labeled oligonucleotide, it can be successfully used in quantitative PCR.

EXAMPLE 8

Figure 6:
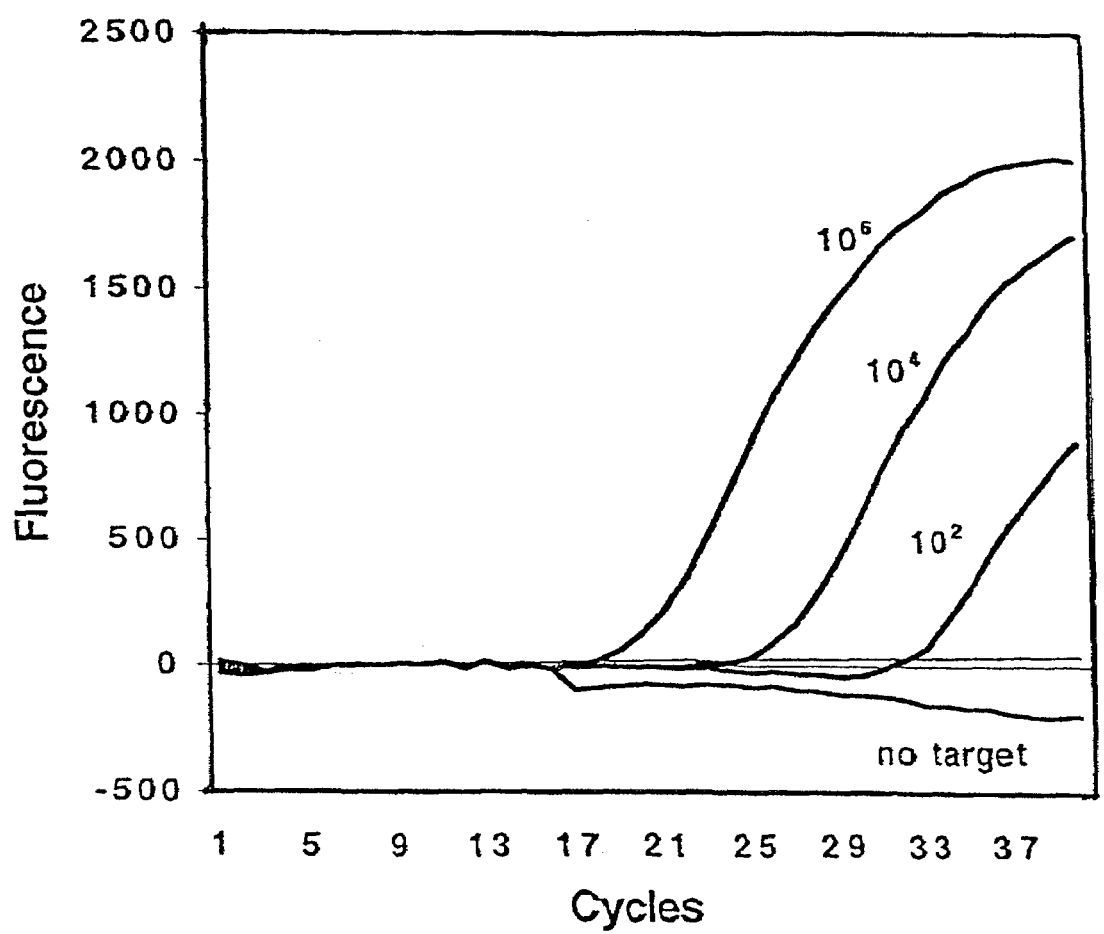
FIG. 6 is a graph of fluorescent intensity as a function of the number of cycles of amplification performed which shows IL4 cDNA PCR with a primer post-synthetically labeled with fluorescein. PCR was performed as described in Example 8. Real-time amplification data were exported from ABI PRIZM™ 7700 Sequence Detector in Excel.

Real-Time PCR of IL4 cDNA Using Primer Post-Synthetically Labeled with FITC Reverse primer for IL4 (Oligo A (SEQ ID NO:1)) was synthesized and labeled post-synthetically as described above. Amplification was performed with $10^6$, $10^4$, $10^2$ and 0 copies of nucleic acid target as described in the previous example. As shown in FIG. 6, all dilutions of the DNA target can be detected.

The experimental results in preceding examples demonstrate that different methods of the labeling of oligonucleotides can be used for achieving the same result. Also, since two methods of synthesis provide different structures of the linker arm between oligonucleotide and fluorophore, different linker arms can be used to attach fluorophore in the proposed method.

EXAMPLE 9

Figure 7:
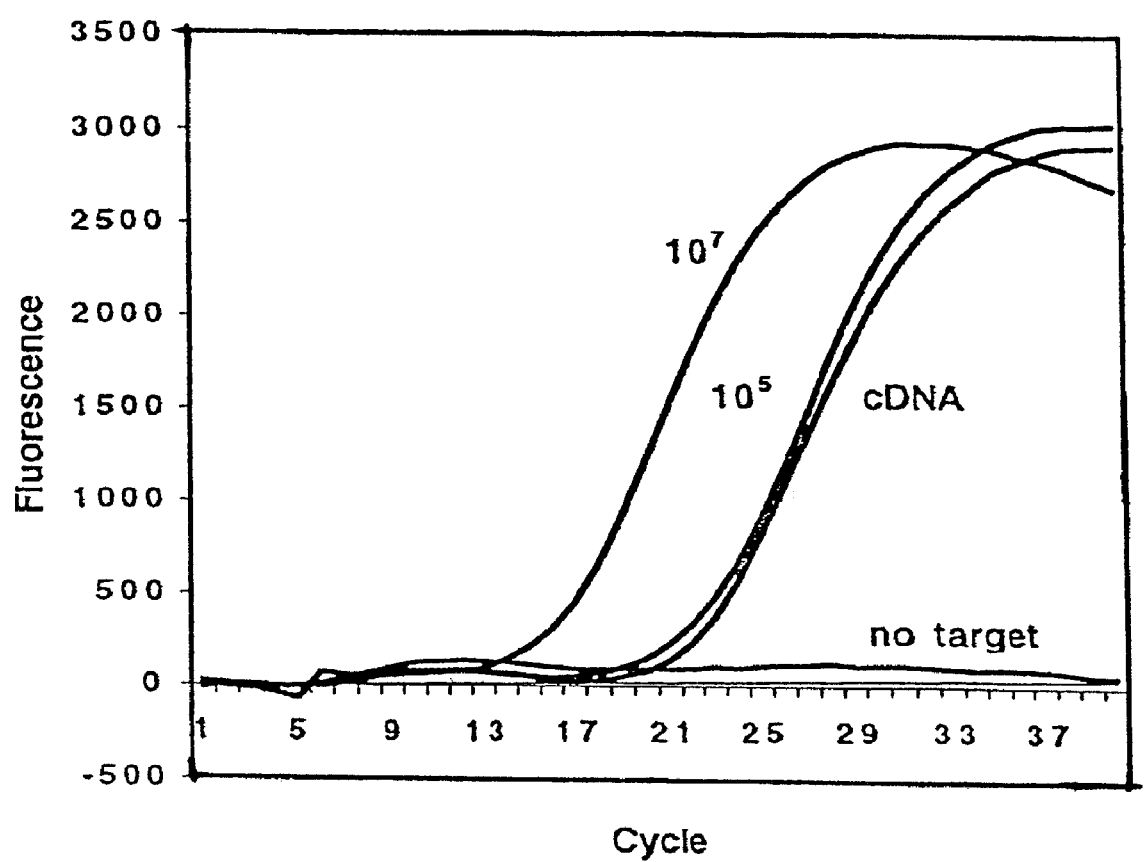
FIG. 7 is a graph of fluorescent intensity as a function of the number of cycles of amplification performed which shows detection of b-actin cDNA by PCR with a primer internally labeled with fluorescein. PCR was performed as described in Example 9.

Real-Time PCR of B-Actin cDNA with a Primer Internally Labeled with Fluorescein Fluorescein-dT was directly incorporated into the sequence of the forward primer for human b-actin cDNA (Oligo J (SEQ ID NO:10)) during chemical synthesis. This oligonucleotide and unlabeled reverse primer (Oligo K (SEQ ID NO:11)) were used for the amplification of b-actin cDNA. cDNA target was obtained by reverse transcription of HeLa cell mRNA and also a cloned cDNA fragment ($10^7$, $10^5$ and 0 copies per reaction). Quantitative PCR was performed as described above. As shown in FIG. 7, all dilutions of the DNA target can be detected.

The results of this experiment demonstrate that different targets can be detected using the proposed method.

EXAMPLE 10

Realtime PCR of b-Actin cDNA with a Primer Internally Labeled Through a "Tag" Sequence Non-Complementary to the Target All the above experiments showed that the label could be incorporated into the sequence of oligonucleotide complementary to the target nucleic acid. However, the same result can be obtained if the label is present on a non-complementary tag sequence attached to the 5'-end of a PCR primer. In this case a signal will be generated after this tailed primer is copied and incorporated into the double-stranded PCR product. This approach was demonstrated in the b-actin PCR.

Figure 8:
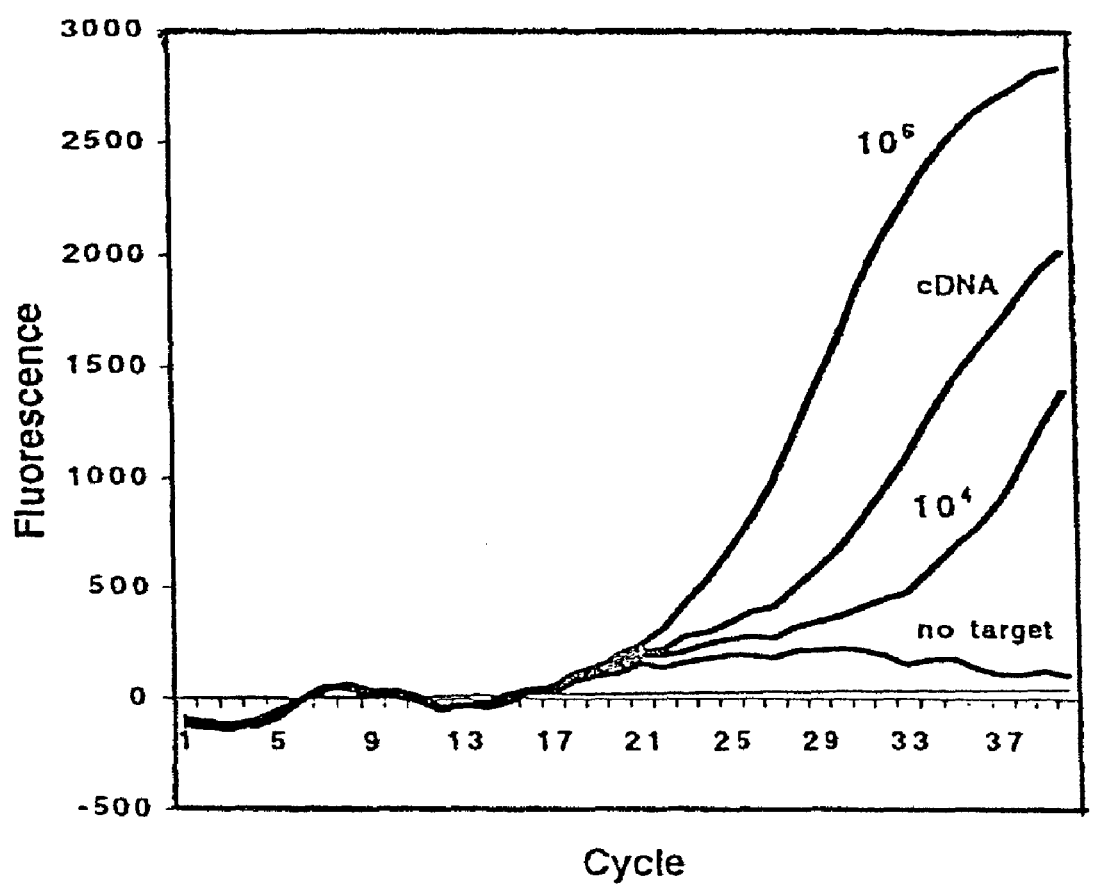
FIG. 8 is a graph of fluorescent intensity as a function of the number of cycles of amplification performed which shows b-Actin cDNA PCR with a primer internally labeled through a 5'-detection tail. PCR was performed as described in Example 10.

Oligodeoxynucleotide (Oligo L (SEQ ID NO:12)) was synthesized with Fluorescein-dT directly incorporated into the structure of 9-nucleotide tail, non-complementary to the target. This tail was added to the 5'-end of the b-actin forward primer. Oligo L (SEQ ID NO:12) and unlabeled reverse primer (Oligo K (SEQ ID NO:11)) were used to amplify b-actin cDNA and $10^6$, $10^4$, and 0 copies of cloned target. As shown in FIG. 8, both cloned target and cDNA in total cDNA population can be detected.

EXAMPLE 11

Allele Specific PCR with Modified Oligonucleotide Primers

Figure 9:
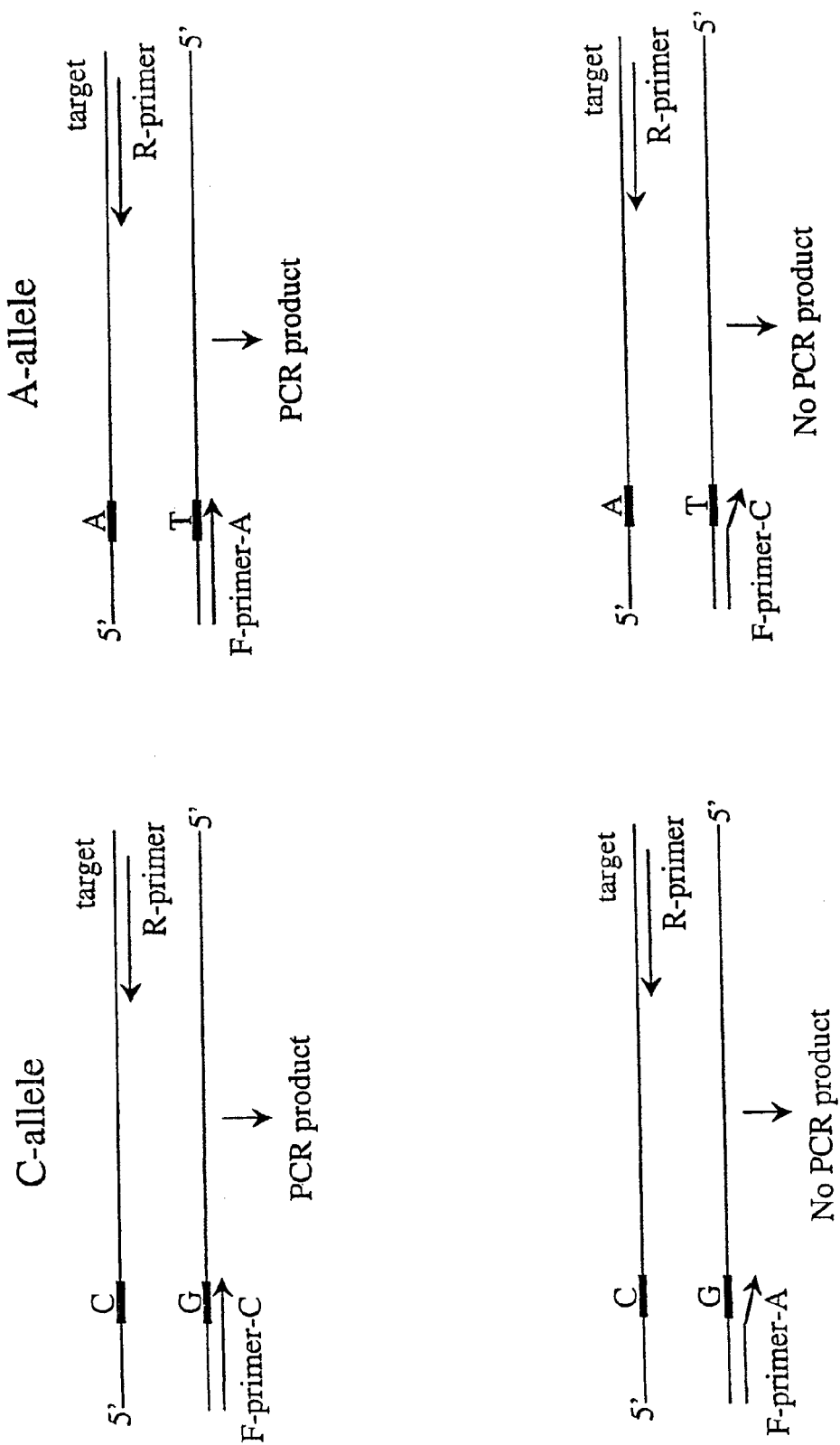
FIG. 9 is a schematic representation of allele specific PCR.

The principle of allele specific PCR is presented in FIG. 9. The method operates on the basis of the specific amplification of a target allele by the PCR with primers designed such that their 3' ends are placed at the mutation site (i.e., the 3'-most nucleotide of the primer corresponds to the mutated nucleotide in the target/template nucleic acid). When this base is complementary to that of the corresponding nucleotide of the specific allele, the target is amplified; when it is not complementary PCR will proceed with a significant delay. The longer the delay, the more efficiently the system can discriminate between alleles. In some preferred embodiments, the present invention provides oligonucleotides useful for allele specific PCR which oligonucleotides comprise a specificity enhancing group that improves discrimination between alleles.

Allele specific PCR was performed using regular PCR primers and the primers labeled with fluorescein at a base close to the 3'-end. Two positions of the IL4 cDNA were chosen for detection, C297 and G300. For each position two PCRs were performed using the same forward primer (Oligo 1 (SEQ ID NO:13)) and different reverse primers: wild type (WT), complementary to the target, or mutant (MUT) with a mismatch at the 3'-end. The sequences of the primers used are provided in Table 2. Each of these allele specific primers was synthesized with and without chemical modification on a T-base close to the 3'-end. The primers used were 297 WT-primer complementary to the C-allele at position 297 (Oligo 2 (SEQ ID NO:14)), 297 MUT-same primer with C-T mutation at the 3'-end (Oligo 3 (SEQ ID NO:15)), 300 WT-primer complementary to the C-allele at position 300 (Oligo 4 (SEQ ID NO:16)) and 300 MUT-same primer with G-T mutation at the 3'-end (Oligo 5 (SEQ ID NO:17)). Oligonucleotides 6, 7, 8, 9 (SEQ ID NOs:18, 19, 20, 21, respectively) correspond to oligonucleotides 2, 3, 4, 5 (SEQ ID NOs:14, 15, 16, 17, respectively) with fluorescein attached to the designated T-base.

Figure 10:
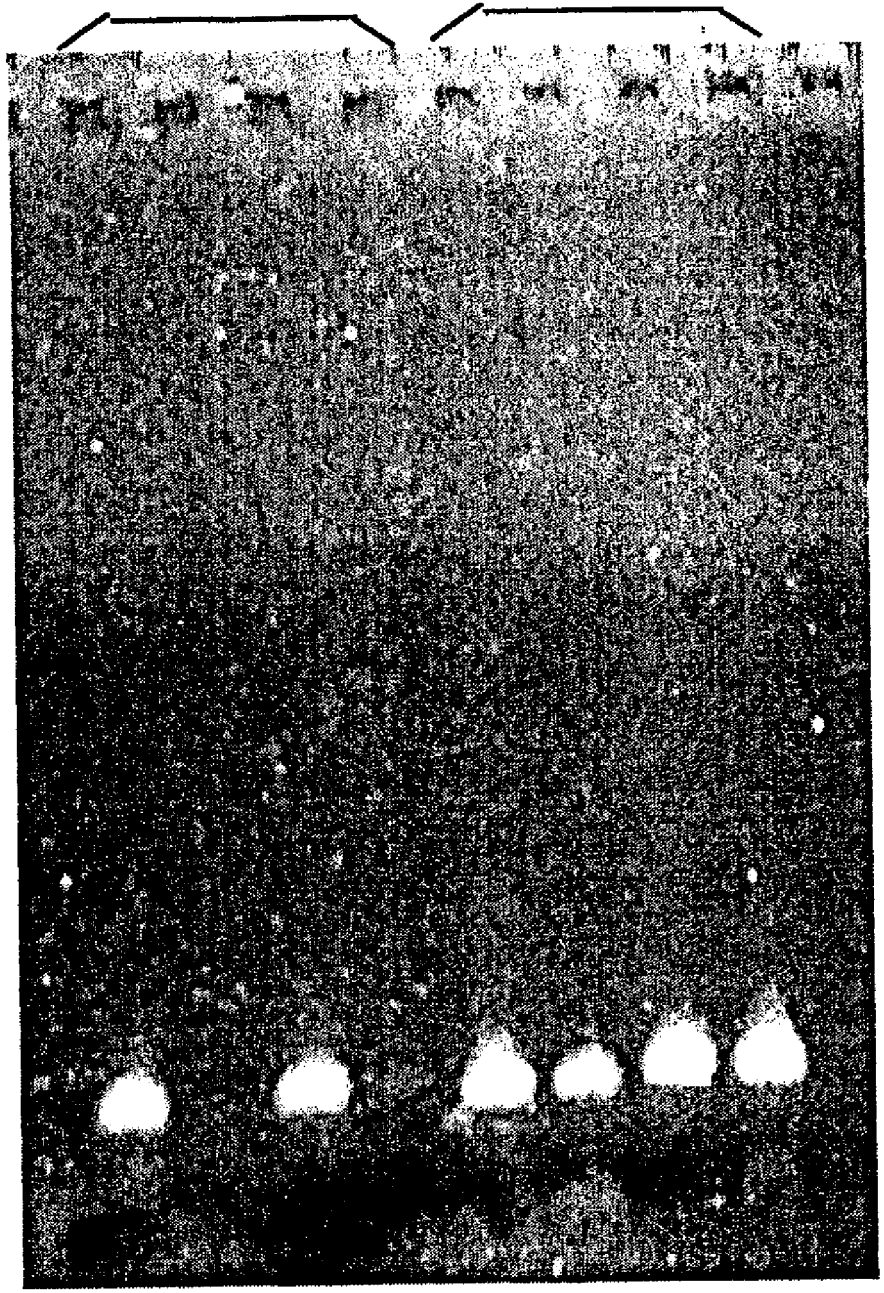
FIG. 10 is a photograph of an agarose gel showing the results of an allele specific PCR reaction comparing the primers of the present invention to standard primers.

Three step PCR was performed for 40 cycles with Platinum Taq™ as described above and the results are shown in FIG. 10. Reverse primers with their 3'-end at positions 297 or 300 were either complementary to the target (WT) or had a 3' mutation (MUT). Lanes 1 through 4 show the results obtained with primers modified with fluorescein as a specificity enhancing group; lanes 5 through 8 show the results obtained with unmodified primers. Lanes 1 and 5 show the results using the primer 297 WT; lanes 2 and 6 show the results using the primer 297 MUT; lanes 3 and 7 show the results using primer 300WT; lanes 4 and 8 show the results using primer 300 MUT. A comparison of lanes 2 and 6 and a comparison of lanes 4 and 8 show that the presence of a modification allows discrimination that is almost complete after 40 cycles. The practice of the present invention is not limited to the use of fluorescein, similar results were obtained with TAMRA as a specificity enhancing group (data not shown).

EXAMPLE 12

Allele Specific PCR with Hairpin Oligonucleotide Primers

In some preferred embodiments, the primers of the present invention may be modified such that they assume a hairpin structure. This may be accomplished by adding one or more bases to the 5'-terminal of the oligonucleotide which bases are selected to be complementary to the bases at the 3'-terminal of the oligonucleotide. In some preferred embodiments, at least one to about 20 contiguous nucleotides are added to the 5'end of the oligonucleotide that are complementary to the at least one to 20 contiguous nucleotides present in the 3'-end of the oligonucleotide. In a preferred embodiment, from one to about 10 nucleotides are added to the 5'-end of the oligonucleotide, the nucleotides selected such that they are complementary to the at least one to about 10 contiguous nucleotides present in the 3'-end of the oligonucleotide. In another preferred embodiment, from one to about 5 nucleotides are added to the 5'-end of the oligonucleotide, the nucleotides selected such that they are complementary to the at least one to about 5 contiguous nucleotides present in the 3'-end of the oligonucleotide.

Figure 11:
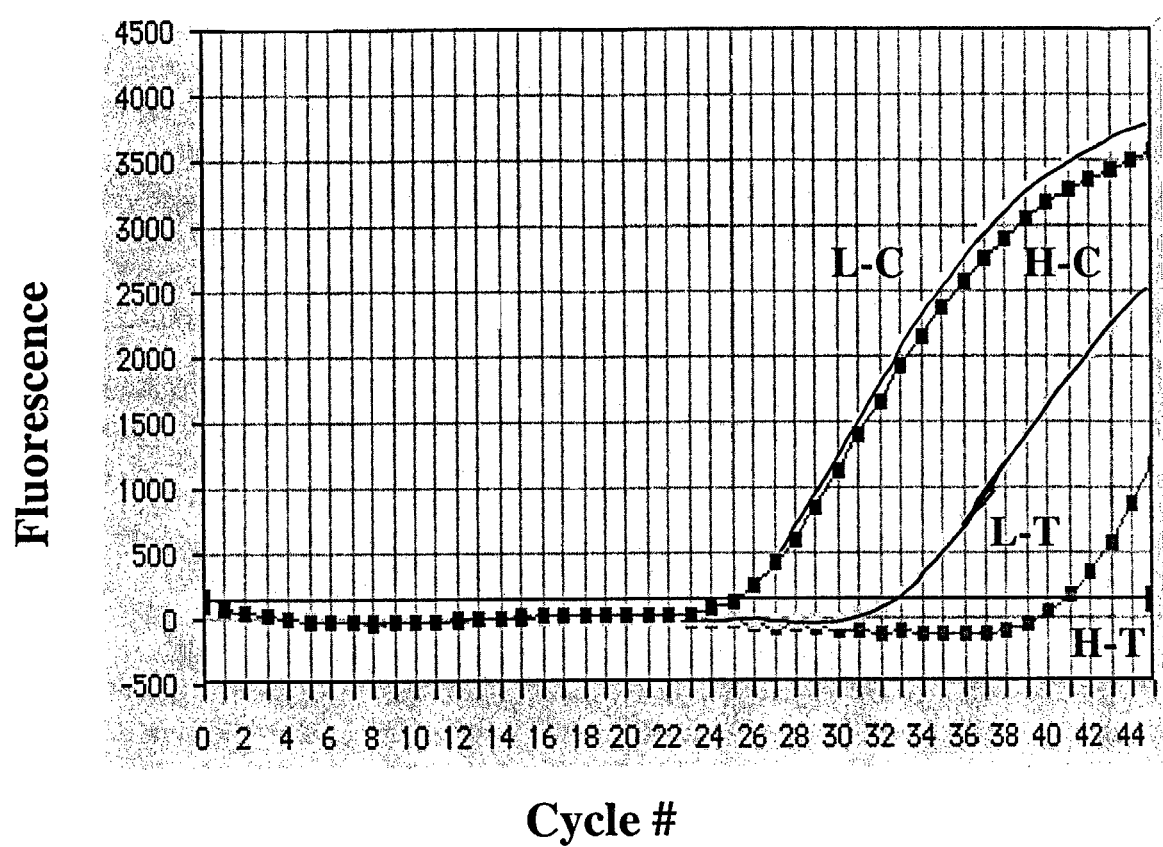
FIG. 11 is a plot of fluorescence as a function of the number of cycles of PCR performed in an allele specific PCR reaction comparing the hairpin primers of the present invention to standard linear primers.
Figure 12:
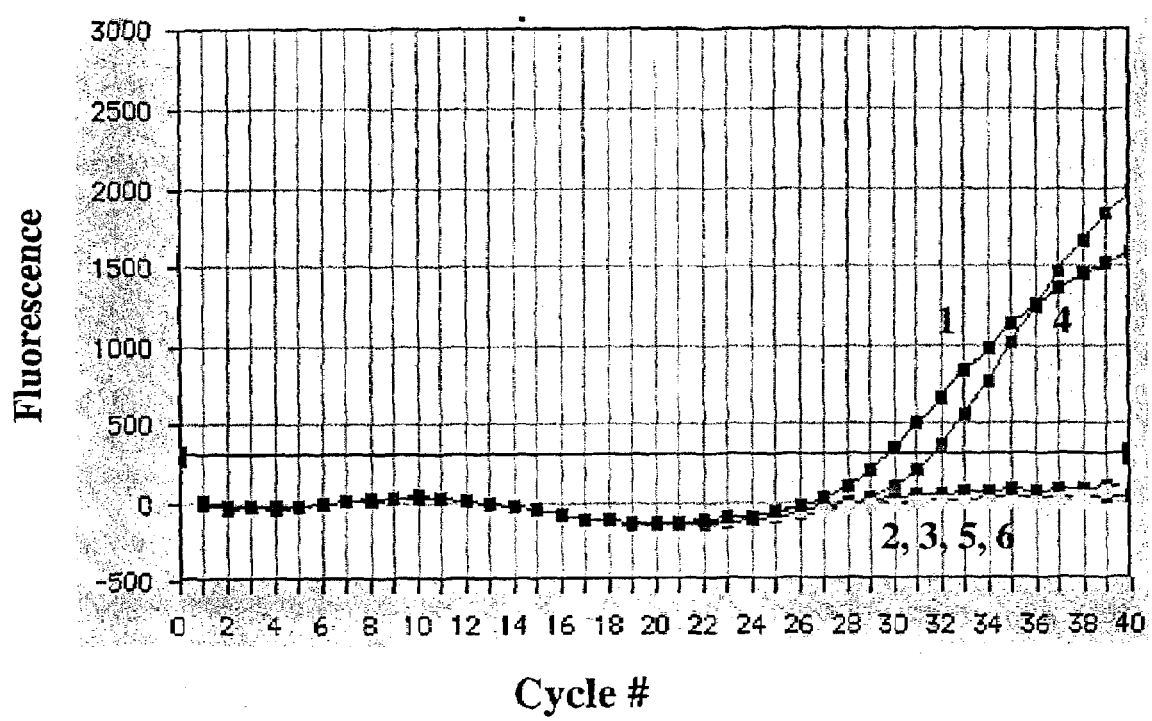
FIG. 12 is a plot of fluorescence as a function of the number of cycles of PCR performed in an allele specific PCR reaction comparing the hairpin primers of the present invention to standard linear primers using a two step PCR reaction format.

The present invention is based upon the surprising result that the mutation discrimination can be improved through the secondary structure of the allele specific primers. This feature is exemplified using primers specific for the RDS gene. Forward primers for the RDS gene had their 3' ends located at position 558, the site of a C/T polymorphism. The DNA target contained the C-allele. The reverse primer was the same for both alleles and contained the label that permitted homogeneous detection of amplification in real time (Oligo 10 (SEQ ID NO:22)). Forward allele specific primers were either of the conventional linear structure (Oligo 11, 12 (SEQ ID NOs:23, 24, respectively)) or had the hairpin structure (Oligo 13, 14 (SEQ ID NOs:25, 26, respectively)). Hairpin primers consisted of the target-specific sequence and a short tail complementary to the 3'-fragment of the primer. Three step PCR was performed with Platinum Taq™ DNA polymerase on PRIZM 7700 as described above. The results in FIG. 11 show that the blunt-end hairpin structure of the primer significantly improves mutation discrimination. The primers of the invention were used to descriminate between the C and the T allele of human RDS gene by allele-specific PCR with Platinum Taq™ DNA polymerase using the same fluorescent reverse primer (Oligo 10 (SEQ ID NO:22)) and different allele specific forward primers. The primers used were designated L-C for the linear primer specific for C-allele (Oligo 11 (SEQ ID NO:23)), L-T for the linear primer specific for T-allele (Oligo 12 (SEQ ID NO:24)), H-C for the hairpin primer specific for C-allele (Oligo 13 (SEQ ID NO:25)) and H-T for the hairpin primer specific for T-allele (Oligo 14 (SEQ ID NO:26)). A comparison of the real time fluorescence of the reactions is plotted as a function of the cycle number. The linear T mismatched primer generated a signal that was detectable well before the hairpin T mismatched primer signal. This demonstrates that the discrimination between the alleles was improved by incorporating the 3'-terminal of the primer into a hairpin Another example of allele specific PCR using hairpin primers is shown in FIG. 12. Here two genomic DNA samples were tested by two step PCR. One of the samples was known to have a 558C-allele of RDS gene, another the 558T allele. All forward primers were hairpin primers and fluorescent reverse primer was used for the detection. Curve 1 was obtained with the C-primer with C-target DNA; curve 2 was obtained using the C-primer with T-target DNA; curve 3 was obtained using C-primer with no target DNA (negative control); curve 4 was obtained using the T-primer with T-target DNA; curve 5 was obtained using T-primer with C- target DNA; curve 6 was obtained using T-primer with no target (negative control).

Figure 13:
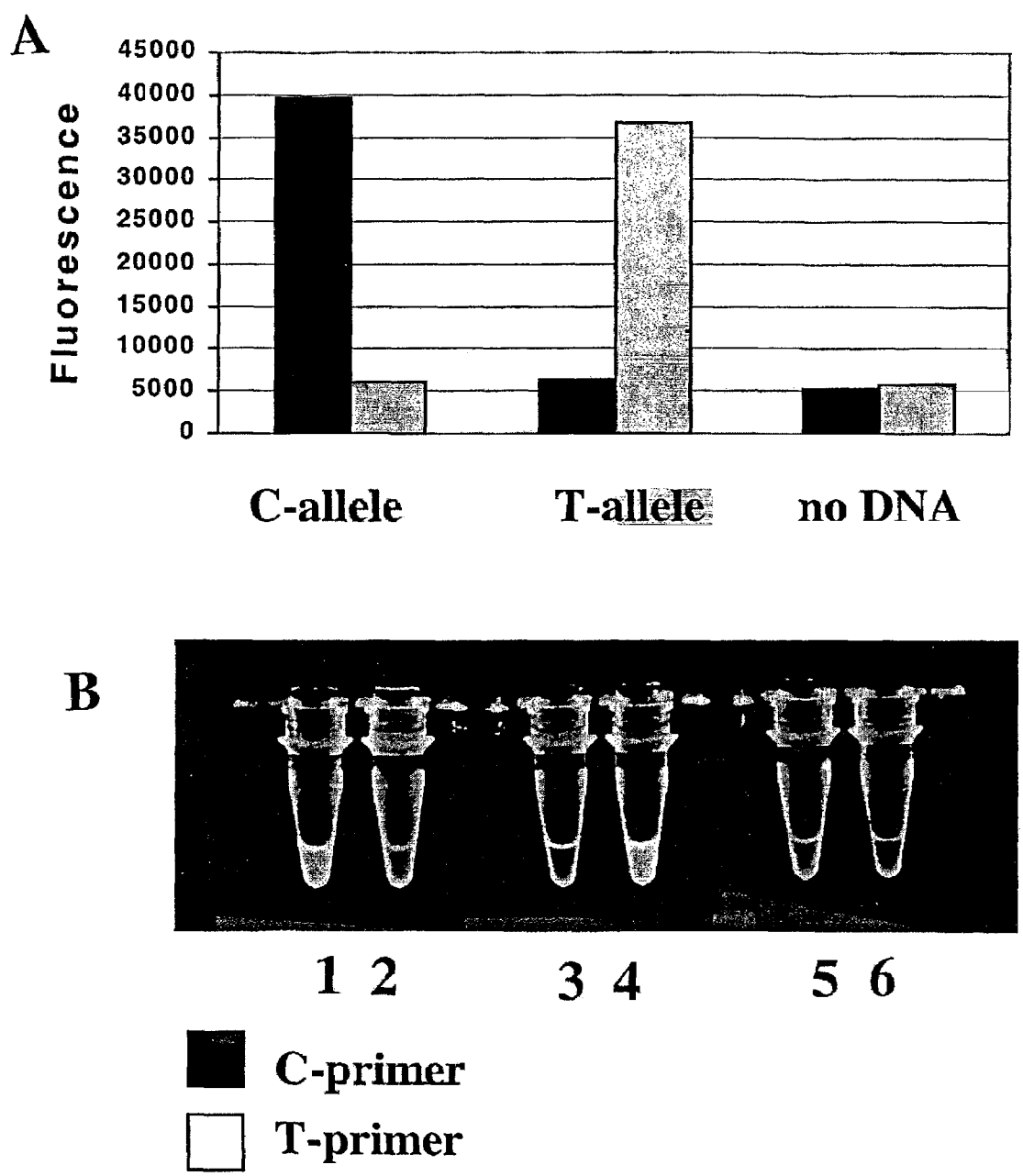
FIG. 13 Panel A shows a bar graph of the fluorescence intensity obtained at the end point of an allele specific PCR reaction using the primers of the present invention. Panel B is a photograph of the PCR tubes in which the allele specific reaction was conducted illuminated with ultraviolet light.

The results demonstrate that only C-allele with C-specific primers and T-allele with T-specific primers gave a positive signal when hairpin primers were used. No increase of fluorescence was detected when the primer had a 3'-mismatch. No signal was generated in the absence of target. As shown in FIG. 13, the alleles can be detected with the same high level of specificity not only in real time but also at the end point. Fluorescent reverse primer was used for the detection. 1, 3, 5 C-specific primers, 2, 4, 6 T-specific primers, 1 and 2 C allele target DNA, 3 and 4 T allele target DNA, 5 and 6 no DNA (negative controls). Panel A shows a bar graph of the fluorescence obtained while Panel B shows a photograph of the reaction mixture after the amplification reactions. End point detection is permitted by high signal/noise ratio of the detection system and can be performed using fluorescent plate reader or UV transilluminator and digital camera.

Figure 14:
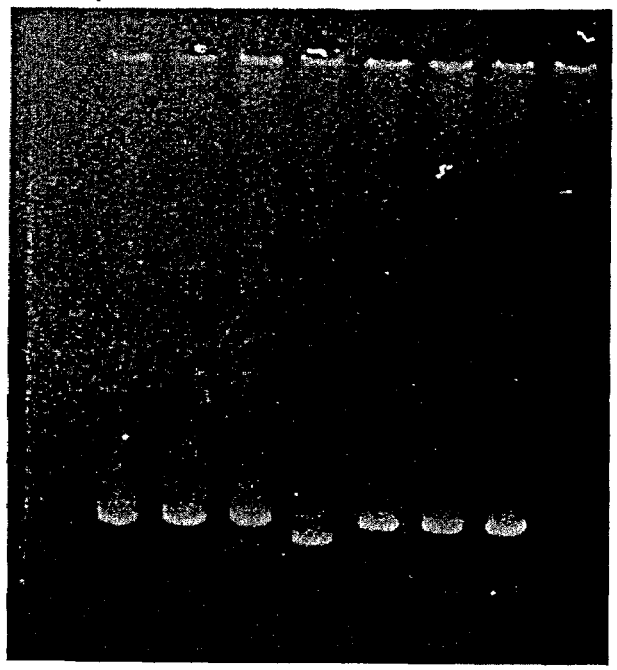
FIG. 14 is a photograph of an agarose gel showing the effects of target DNA concentration on an allele specific PCR reaction using the primers of the present invention.

Another surprising result of the use of the primers of the present invention is the elimination of primer dimers from the PCR reaction. As shown in FIG. 14, the use of a hairpin oligonucleotide in the PCR reaction eliminates the formation of primer dimers. IL4 cDNA was used as a PCR target. Oligo 1 (SEQ ID NO:13) was used as a forward primer, oligo 2 (SEQ ID NO:14) as a linear reverse primer and Oligo 15 (SEQ ID NO:27) as a hairpin reverse primer. PCR was performed with platinum Taq™ for 50 cycles. Lanes 1, 5 contained $10^6$ copies of target; lanes 2, 6 contained $10^4$ copies of target; lanes 3, 7 contained $10^2$ copies of target; and lanes 4, 8 contained no target. Comparison of the lanes 4 and 8 shows that primer-dimer was formed with linear reverse primer but not with the hairpin.

EXAMPLE 13

Use of Mismatch Discriminating Polymerases in Allele Specific PCR

The ability to discriminate between alleles by allele specific PCR may be improved by using DNA polymerases modified to be substantially unable to extend an oligonucleotide when the 3'-most nucleotide of the oligonucleotide is not base paired with the target nucleic acid sequence. The preparation of such modified DNA polymerases is disclosed in WO 99/10366 and WO 98/35060. These publications disclose the cloning and mutagenesis of thermostable polymerases, in particular, the thermostable DNA polymerase isolated from *Thermatoga* spp. In some preferred embodiments of the present invention, allele specific PCR is performed using a mutant DNA polymerase derived from the DNA polymerase of *Thermotoga neopolitana* (Tne). Suitable mutations include deletion of one or more amino acids, frame shift mutations, point mutations that result in one or more amino acid substitutions at one or more sites in the enzyme, insertion mutations and combinations thereof. In a preferred embodiment, the mutations may include a deletion of the first 283 amino acids of the wild type enzyme leaving a fragment that begins with methionine 284 (Δ283), a point mutation changing amino acid 323 from aspartic acid to alanine (D323A) and a point mutation changing amino acid 722 from arginine to lysine (R722K). In some preferred embodiments, the mutant Tne DNA polymerase will have at least all three mutations, i.e. will be Δ283, D323A and R722K.

Figure 15:
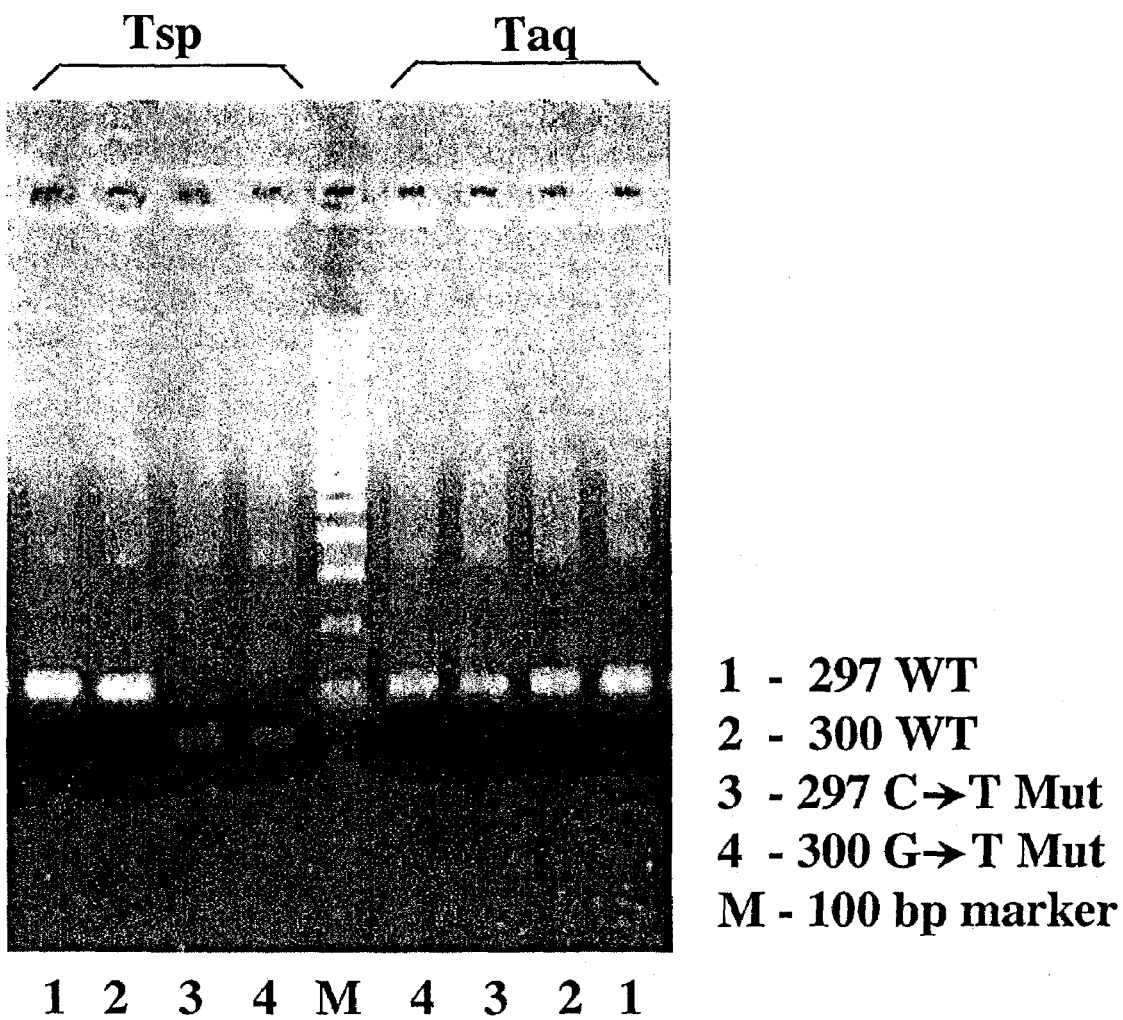
FIG. 15 is a photograph of an agarose gel showing the results of an allele specific reaction comparing the results obtained using Tsp DNA polymerase to Taq DNA polymerase using standard primers.

Platinum Tsp™ DNA polymerase is a proprietary enzyme of LifeTechnologies that can be activated by temperature thus providing a hot start for PCR (U.S. Pat. Nos. 5,338,671 and 5,587,287). Here we describe a new property of this enzyme, increased specificity towards the base-paired 3'-end of the primer. PCR was performed for 45 cycles with Platinum Tsp™ or Platinum Taq™ DNA polymerase using IL4 cDNA as a target. Two positions of the IL4 cDNA were chosen for detection, C297 and G300. For each position two PCR reactions were performed using the same forward primer (Oligo 1 (SEQ ID NO:13)) and different reverse primers. Primer sequences are described in Table 1 (Oligos 1-5 (SEQ ID NOs:13-17)). The oligonucleotides are designated wild type (WT), when the 3'-nucleotide is complementary to the target, or mutant (MUT) with a mismatch at the 3'-end. The oligonucleotides used were the 297 WT primer which is complementary to the C-allele at position 297 (Oligo 2 (SEQ ID NO:14), lane 1), the 297 MUT primer which has the same sequence as the 297 WT primer except for a C-T mutation at the 3'-end (Oligo 3 (SEQ ID NO:15), lane 3), the 300 WT primer which is complementary to the C-allele at position 300 (Oligo 4 (SEQ ID NO:16), lane 2) and the 300 MUT primer which has the same sequence as the 300WT primer except for a G-T mutation at the 3'-end (Oligo 5 (SEQ ID NO:17), lane 4). As seen in FIG. 15, a comparison of the results obtained with Tsp™ DNA polymerase to those obtained with Taq™ DNA polymerase show that Platinum Tsp™ has better discriminatory properties than platinum Taq™.

EXAMPLE 14

Use of Hairpin Primers to Enhance Specificity of PCR

It has been unexpectedly found that the hairpin primers of the present invention may be used to enhance the specificity of PCR reactions. Without wishing to be bound by theory, it is believed that the ability of the primers to form hairpin structures at temperatures around the annealing temperature of the PCR reaction makes the primers less capable of mis-priming to the target nucleic acid molecule. This increase in specificity is not dependent upon the particular target nucleic acid template and has been observed with a variety of templates. The increase in specificity will be particularly important for the amplification of templates that are difficult to amplify and that produce low amounts or none of the desired amplification product in PCR reactions.

In addition to hairpin structures, any structure that sequesters the 3'-end of the oligonucleotide primer may be used to practice the present invention. For example, the 5'-portion of the primers of the present invention may be provided with sequence that is capable of forming a duplex such that the 3'-end interacts with the duplex to form a triplex. In general, any primer sequence that reversibly involves the 3'-portion of the primer in a stable structure that is not capable annealing to the template DNA while in that structure may be used to practice the present invention. In some embodiments, an oligonucleotide complementary to the primer may be provided so as to sequester the 3'-end of the primer. Complementary oligonucleotides may be provided with a 5'-overhanging region which may be designed to include self complementary regions capable of forming hairpins. It is not necessary that the entire 3'-portion of the primer be sequestered, so long as the portion not sequestered is not capable of mis-priming the nucleic acid template, it is sufficient to practice the present invention.

Figure 16:
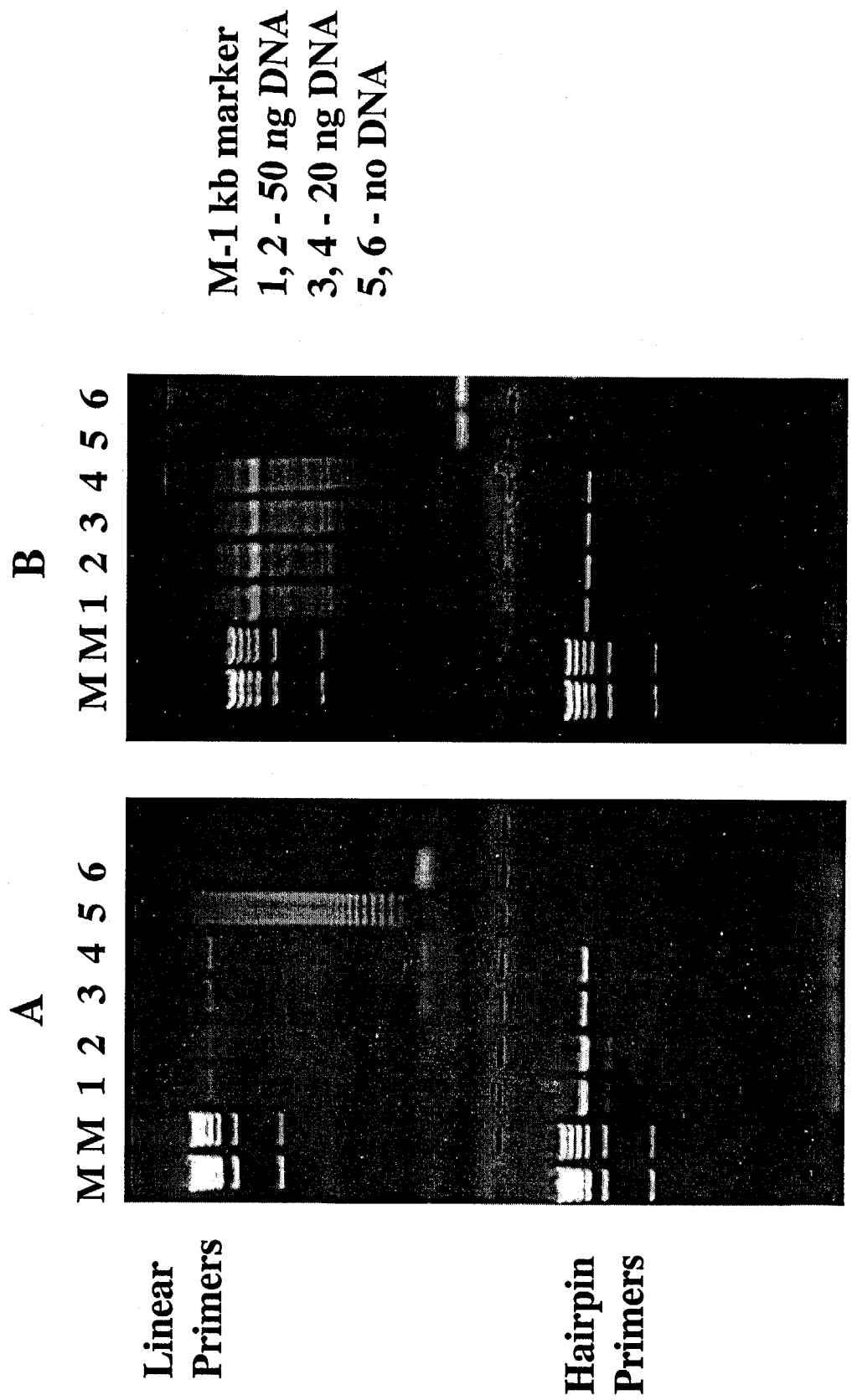
FIG. 16 is a photograph of an ethidium bromide stained agarose gel showing the results of comparison of the hairpin oligonucleotides of the present invention to linear oligonucleotides in an amplification reaction using varying amounts of template DNA. Panel A shows the amplification of a 3.6 kb fragment of the human beta-globin gene using a first primer set. Panel B shows the amplification of a 3.6 kb fragment of the human beta-globin gene using a second primer set.

In the first experiment, a 3.6 kb fragment of the human beta-globin was amplified from human genomic DNA using Platinum Pfx thermostable polymerase in Pfx buffer (LifeTechnologies). Two different sets of primers were used. Each set of primers consisted of two primer pairs, one pair of linear primers and another pair of primers having a hairpin version of the same gene specific primer sequence. The hairpin version of each pair of oligonucleotides was constructed by adding bases to the 5'-end of the primer sequence that are complementary to the 3'-end of the oligonucleotide. Typically, the number of bases added to the 5'-end is selected such that the oligonucleotide forms a hairpin at temperatures below the annealing temperature and assumes a linear form at or near the annealing temperature. Those skilled in the art can readily determine the number of nucleotides to be added to the 5'-end of the primer so as to control the temperature at which the primer assumes a linear form. It is not necessary that the oligonucleotides of the invention be entirely converted to linear form at the annealing temperature; those skilled in the art will appreciate that the oligonucleotides of the present invention may be capable of reversibly melting and self reannealing (i.e., breathing). So long as the sequences of the oligonucleotides of the invention are selected such that a sufficient number of oligonucleotides are available to prime the extension/amplification at the annealing temperature, the sequence is suitable for use in the present invention whether or not some of the oligonucleotides remain in a hairpin form at the annealing temperature. The number of nucleotides that may be added may be from about 3 nucleotides to about 25 nucleotides, or from about 3 nucleotides to about 20 nucleotides, or from about 3 nucleotides to about 15 nucleotides, or from about 3 nucleotides to about 10 nucleotides, or from about 3 nucleotides to about 7 nucleotides. In some preferred embodiments, from about 5 to about 8 nucleotides may be added to the 5'-end of the primer oligonucleotide in order to form the hairpin oligonucleotides of the present invention. For the amplification of the beta globin gene, two sets of primers were used. Set A oligos 16 (SEQ ID NO:28) and 17 (SEQ ID NO:29) (linear) or 18 (SEQ ID NO:30) and 19 (SEQ ID NO:31) (hairpin) and Set B-oligos 20 (SEQ ID NO:32) and 21 (SEQ ID NO:33) (linear) or 22 (SEQ ID NO:34) and 23 (SEQ ID NO:35) (hairpin). PCR was performed as follows: 2 minutes at 94° C. followed by 35 cycles of: 15 seconds at 94° C. then 30 seconds at 60° C. followed by 4 minutes at 68° C. using varying amounts of template DNA. The results are shown in FIG. 16. The lanes labeled M contain molecular weight markers. Lanes 1 and 2 show the results obtained using 50 ng of template DNA, lanes 3 and 4 show the results obtained using 20 ng of template and lanes 5 and 6 show the no DNA controls. It is clear that both linear sets of primers generated various mis-priming products and primer-dimers, while amplification with the corresponding hairpin primers produced the expected size amplification product with very little incorrect product.

Figure 17:
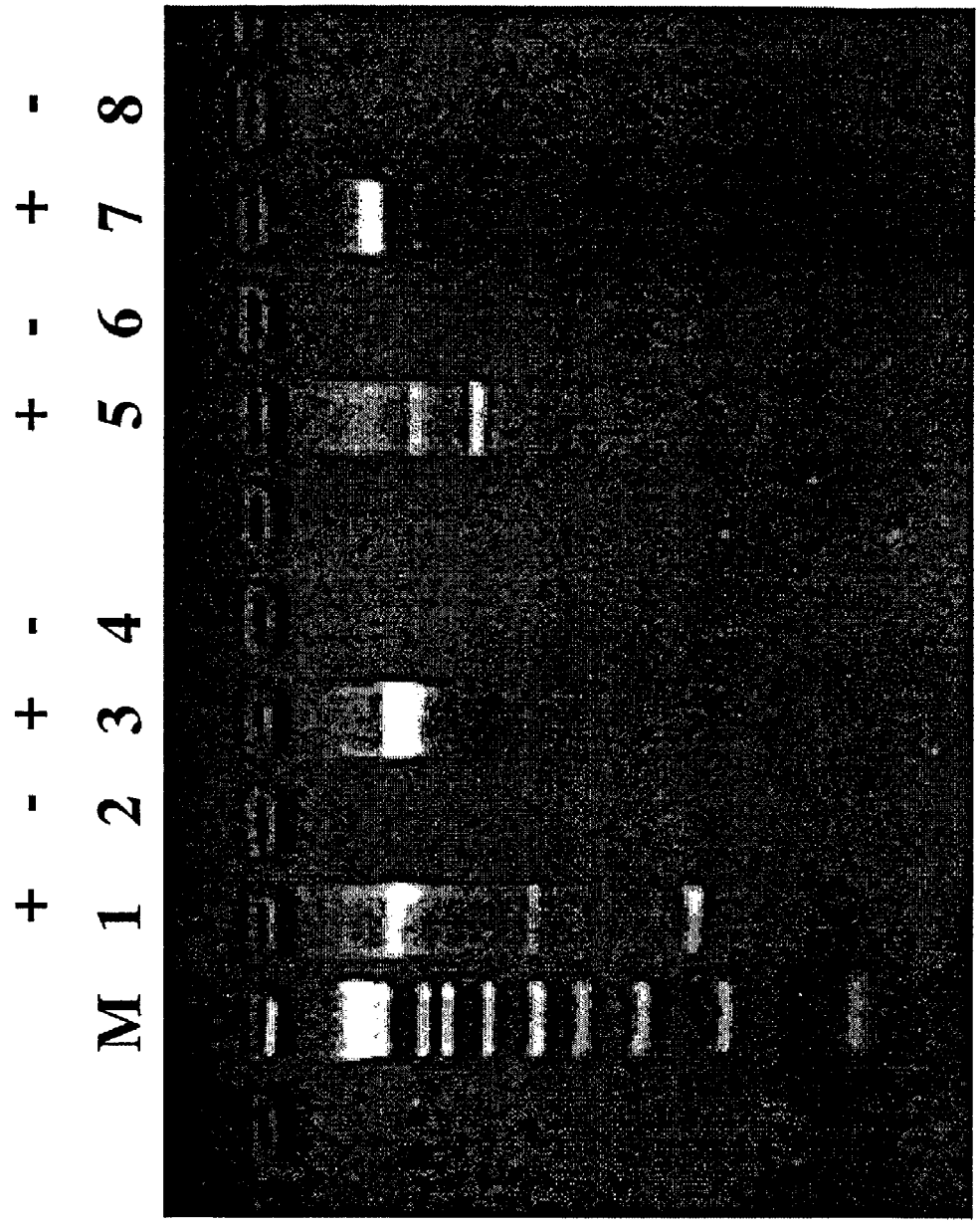
FIG. 17 is a photograph of an ethidium bromide stained agarose gel showing the results of comparison of the hairpin oligonucleotides of the present invention to linear oligonucleotides in an amplification reaction to produce varying sized amplification products. Panel A shows the amplification of a 1.3 kb fragment of the NF2 gene. Panel B shows the amplification of a 1.6 kb fragment of the NF2 gene.

Similar results were obtained during the amplification of another human gene Necrosis Factor 2(NF2). 1.3 and 1.6 kb fragments were amplified using Platinum Taq DNA polymerase in PCR SuperMix (LifeTechnologies). For the amplification of the 1.3 kb fragment oligos 24 (SEQ ID NO:36) and 25 (SEQ ID NO:37) (linear) or 26 (SEQ ID NO:38) and 27 (SEQ ID NO:39) (hairpin) were used as primers. For the amplification of the 1.6 kb fragment oligos 28 (SEQ ID NO:40) and 29 (SEQ ID NO:41) (linear) or 30 (SEQ ID NO:42) and 31 (SEQ ID NO:43) (hairpin) were used as primers. PCR was performed on 50 ng of human genomic DNA as follows: 2 minutes at 94° C. followed by 35 cycles of: 30 seconds at 94° C., 30 seconds at 62° C. and 4 minutes at 68° C. The results are shown in FIG. 17. Lane M contains molecular weight markers. + indicates the presence of template DNA and − indicates the no DNA control. Lane 1 shows the results using linear primers for the 1.3 kb fragment in the presence of template DNA. Lane 2 shows the no DNA control for lane 1. Lane 3 shows the results obtained using the hairpin primer for the 1.3 kb fragment while lane 4 is the no DNA control for lane 3. Lane 5 shows the results obtained using the linear primers for the 1.6 kb fragment while lane 6 is the no DNA control for lane 5. Lane 7 shows the results obtained using the hairpin primers for the 1.6 kb fragment while lane 8 is the no DNA control for lane 7. In both instances the hairpin primers gave more and cleaner amplification products of the appropriate size than linear primers of the same gene specific sequence.

Having now fully described the present invention in some detail by way of illustration and example for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

What is claimed is:

1. A method for the quantitation or detection of one or more target nucleic acid molecules in a sample during nucleic acid synthesis comprising:

mixing one or more a target nucleic acid molecules with one or more fluorescently labeled oligonucleotides, wherein said one or more oligonucleotides are labeled with only a single type of fluorescent label and said oligonucleotide undergoes a detectable change in fluorescence upon hybridization of said one or more oligonucleotides to said one or more target nucleic acid molecules;

incubating said mixture under conditions sufficient to synthesize one or more nucleic acid molecules complementary to all or a portion of said one or more target nucleic acid molecules, said one or more synthesized nucleic acid molecules comprising said one or more oligonucleotides; and detecting the presence or absence or quantifying the amount of said one or more synthesized nucleic acid molecules by measuring said fluorescent label; wherein said fluorescent label is selected from the group consisting of JOE (2'7'-dimethoxy-4'5'-dichloro-6-carboxyfluorescein), FAM (5-carboxyfluorescein), TAMRA (N,N,N',N'-tetramethyl-6-carboxyrhodamine), or ROX (6-carboxy-X-rhodamine).

2. A method for quantitation or detection of one or more target nucleic acid molecules in a sample during nucleic acid amplification comprising:

mixing one or more target nucleic acid molecules with one or more fluorescently labeled oligonucleotides under conditions sufficient to amplify one or more nucleic acid molecules complementary to all or a portion of said one or more target nucleic acid molecules, said one or more amplified nucleic acid molecules comprising said one or more oligonucleotides, wherein said one or more oligonucleotides are labeled with only a single type of fluorescent label and said oligonucleotide undergoes a detectable change in fluorescence upon hybridization of said one or more oligonucleotides to said one or more target nucleic acid molecules; and detecting the presence or absence or quantifying the amount of said one or more target nucleic acid molecules by measuring said fluorescent label; wherein said fluorescent label is selected from the group consisting of (2'7'-dimethoxy-4'5'-dichloro-6-carboxyfluorescein), FAM (5-carboxyfluorescein), TAMRA (N,N,N',N'-tetramethyl-6-carboxyrhodamine), or ROX (6-carboxy-X-rhodamine).

3. The method of claims 1 or 2, wherein said detection step comprises detecting or measuring the level of activity of the fluorescent label during said synthesis or amplification compared to the level of activity of the fluorescent label in the absence of said synthesis or amplification.

4. The method of claim 2, wherein said amplification is accomplished by at least one method selected from the group consisting of PCR, 5-RACE, RT PCR, Allele-specific PCR, Anchor PCR, "one-sided PCR," LCR, NASBA, and SDA.

5. The method of any one of claims 1 or 2, wherein said one or more oligonucleotides comprise one or more hairpin structures.

6. A method for amplifying a double stranded nucleic acid molecule, comprising:

providing a first and second primer, wherein said first primer is complementary to a sequence within or at or near the 3"-termini of the first strand of said nucleic acid molecule and said second primer is complementary to a sequence within or at or near the 3"-termini of the second strand of said nucleic acid molecule;

hybridizing said first primer to said first strand and said second primer to said second strand in the presence of one or more polymerases, under conditions such that said primers are extended to result in the synthesis of a third nucleic acid molecule complementary to all or a portion of said first strand and a fourth nucleic acid molecule complementary to all or a portion said second strand;

denaturing said first and third strands, and said second and fourth strands; and repeating the above steps one or more times, wherein one or both of said first and second primers are labeled with only a single type of fluorescent label, wherein said fluorescent label is selected from the group consisting of (2'7'-dimethoxy-4'5'-dichloro-6-carboxyfluorescein), FAM (5-carboxyfluorescein), TAMRA (N N,N',N'-tetramethyl-6-carboxyrhodamine), or ROX (6-carboxy-X-rhodamine);

and wherein said primer undergoes a detectable change in fluorescence upon hybridization of said one or more labeled primers to said nucleic acid molecule.

7. The method of claim 6, wherein at least one of said primers comprises at least one hairpin structure.

8. The method of claim 6, wherein said primers further comprise one or more hairpin structures.

9. The method of any one of claims 1, 2, or 6, wherein said detectable label is at the fourth base from the 3' termini.

10. The method of any one of claims 1, 2, or 6, wherein said detectable label is at the fifth base from the 3' termini.

11. The method of any one of claims 1, 2, or 6, wherein said detectable label is at the sixth base from the 3' termini.

12. The method of any one of claims 1, 2, or 6, wherein said detectable label is attached to one of the ten 3'-most terminal nucleotides.

13. The method of any one of claims 1, 2, or 6, wherein said detectable label is attached to one of the twenty 3'-most terminal nucleotides.

* * * * *